United States Patent [19]

Murata et al.

[11] Patent Number: 4,925,838

[45] Date of Patent: May 15, 1990

[54] 3-PYRROLIDINYLTHIO-1-AZABICY-CLO[3.2.0]-HEPT-2-ENE-2-CARBOXYLIC ACID COMPOUNDS

[75] Inventors: Masayoshi Murata, Osaka; Hideo Tsutsumi, Toyonaka; Keiji Matsuda, Takatsuki; Kohji Hattori, Sakai; Takashi Nakajima, Toyonoka, all of Japan

[73] Assignee: Fujisawa Pharmaceutical Company, Ltd., Osaka, Japan

[21] Appl. No.: 323,404

[22] Filed: Mar. 14, 1989

[30] Foreign Application Priority Data

Mar. 18, 1988 [GB] United Kingdom ............... 8806428
May 23, 1988 [GB] United Kingdom ............... 8812159
Sep. 16, 1988 [GB] United Kingdom ............... 8821760

[51] Int. Cl.$^5$ .................... C27D 487/04; A61K 31/40
[52] U.S. Cl. ..................................... 514/210; 540/350
[58] Field of Search ......................... 540/350; 514/210

[56] References Cited

FOREIGN PATENT DOCUMENTS

| 0072710 | 2/1983 | European Pat. Off. ............ 514/210 |
| 0102239 | 3/1984 | European Pat. Off. ............ 514/210 |
| 0126587 | 11/1984 | European Pat. Off. ............ 514/210 |
| 0160391 | 11/1985 | European Pat. Off. ............ 514/210 |
| 0182213 | 5/1986 | European Pat. Off. ............ 514/210 |
| 0243686 | 11/1987 | European Pat. Off. ............ 514/210 |
| 59-16892 | 1/1984 | Japan .................... 514/210 |

*Primary Examiner*—Robert Gerstl
*Attorney, Agent, or Firm*—Oblon, Spivak, McClelland, Maier & Neustadt

[57] ABSTRACT

3-Pyrrolidinythio-1-azabicyclo [3.2.0]hept-2-ene-2-carboxylic acid compounds which have antimicrobial activity have been prepared.

9 Claims, No Drawings

3-PYRROLIDINYLTHIO-1-AZABICYCLO[3.2.0]-HEPT-2-ENE-2-CARBOXYLIC ACID COMPOUNDS

The present invention relates to novel 3-pyrrolidinylthio-1-azabicyclo[3.2.0]hept-2-ene-2-carboxylic acid compounds and pharmaceutically acceptable salts thereof.

More particularly, it relates to novel 3-pyrrolidinylthio-1-azabicyclo[3.2.0]hept-2-ene-2-carboxylic acid compounds and pharmaceutically acceptable salts thereof, which have antimicrobial activity, to processes for the preparation thereof, to a pharmaceutical composition comprising the same, and to a use of the same as a medicament and in the treatment of infectious diseases in human being or animal.

Accordingly, one object of the present invention is to provide novel 3-pyrrolidinylthio-1-azabicyclo[3.2.0]hept-2-ene-2-carboxylic acid compounds and pharmaceutically acceptable salts thereof, which are highly active against a number of pathogenic microorganisms and are useful as antimicrobial agents.

Another object of the present invention is to provide processes for the preparation of novel 3-pyrrolidinylthio-1-azabicyclo[3.2.0]hept-2-ene-2-carboxylic acid compounds and salts thereof.

A further object of the present invention is to provide a pharmaceutical composition comprising, as an active ingredient, said 3-pyrrolidinylthio-1-azabicyclo[3.2.0]hept-2-ene-2-carboxylic acid compounds and pharmaceutically acceptable salts thereof.

Still further object of the present invention is to provide a use of said 3-pyrrolidinylthio-1-azabicyclo[3.2.0]hept-2-ene-2-carboxylic acid compounds and pharmaceutically acceptable salts thereof as a medicament and in the treatment of infectious diseases by pathogenic microorganisms in human being or animal.

The object 3-pyrrolidinylthio-1-azabicyclo[3.2.0]hept-2-ene-2-carboxylic acid compounds are novel and can be represented by the following general formula:

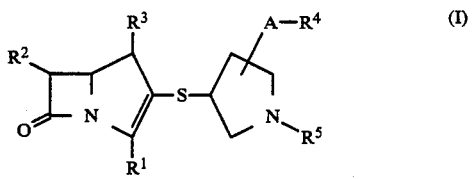

in which
$R^1$ is carboxy or protected carboxy,
$R^2$ is hydroxy(lower)alkyl or protected hydroxy(lower)alkyl,
$R^3$ is hydrogen or lower alkyl,
$T^4$ is aliphatic heterocyclic group which may be substituted by suitable substituent(s),
$R^5$ is hydrogen, lower alkyl or imino-protective group, and
A is lower alkylene,
and pharmaceutically acceptable salts thereof.

Suitable pharmaceutically acceptable salts of the object compounds (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, etc.; a salt with a basic or acidic amino acid (e.g. arginine, aspartic acid, glutamic acid, etc.); an intermolecular or intramolecular quarternary salt; and the like.

The said intermolecular quarternary salt can be formed when $R^5$ is lower alkyl or the aliphatic heterocyclic group in $R^4$ in the compound (I) contains tertiary nitrogen atom(s) (e.g. pyrrolidin-1-yl, piperazin-1-yl, etc.), and suitable intermolecular quaternary salt may include 1-(lower)alkylpyrrolidinio (lower)alkylsulfate (e.g. 1-methylpyrrolidinio methylsulfate, 1-ethylpyrrolidinio ethylsulfate, etc.), 1-(lower)alkylpyrrolidinio halide (e.g. 1-methylpyrrolidinio iodide, etc.), 1-carbamoyl(lower)alkylpyrrolidinio (lower)alkylsulfate (e.g. 1-carbamoylmethylpyrrolidinio methylsulfate, 1-carbamoylethylpyrrolidinio ethylsulfate, etc.), 1-carbamoyl(lower)alkylpyrrolidinio halide (e.g. 1-carbaomylmethylpyrrolidinio iodide, 1-carbamoylethylpyrrolidinio iodide, etc.), 1-(lower)alkylpiperazinio (lower)alkylsulfate (e.g. 1-methylpiperazinio methylsulfate, 1-ethylpiperazinio ethylsulfate, etc.), 1-(lower)alkylpiperazinio halide (e.g. 1-methylpiperazinio iodide, 1-ethylpiperazinio iodide, etc.), and the like.

The said intramolecular salt can be formed when the aliphatic heterocyclic group in $R^4$ in the compound (I) contains tertiary nitrogen atom(s) (e.g. pyrrolidin-1-yl, piperazin-1-yl, etc.) and $R^2$ is carboxy, and suitable intramolecular salt may include 1-(lower)alkylpyrrolidinio carboxylate (e.g. 1-methylpyrrolidinio carboxylate, 1-ethylpyrrolidinio carboxylate, 1-propylpyrrolidinio carboxylate, 1-isopropylpyrrolidinio carboxylate, 1-butylpyrrolidinio carboxylate, etc.), 1-[carbamoyl(lower)alkyl]pyrrolidinio carboxlate (e.g. 1-[carbamoylmethyl]pyrrolidinio carboxylate, 1-[carbamoylethyl]pyrrolidinio carboxylate, 1-[carbamoylpropyl]pyrrolidinio carboxylate, 1-[carbamoylisopropyl]pyrrolidinio carboxylate, 1-[carbamoylbutyl]pyrrolidinio carboxylate, etc.), 1-(lower)alkylpiperazinio carboxylate (e.g. 1-methylpiperazinio carboxylate, 1-ethylpiperazinio carboxylate, 1-propylpiperazinio carboxylate, 1-isopropylpiperazinio carboxylate, 1-butylpiperazinio carboxylate, etc.), and the like.

Further, said intramolecular salt can be formed when the nitrogen atom in the pyrrolidine moiety

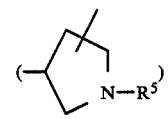

of the compound (I) has an additional substituent and $R^2$ is carboxy, and suitable example of such pyrrolidine moiety may include 1,1-di(lower)alkyl-4-pyrrolidinio (e.g. 1,1-dimethyl-4-pyrrolidinio, etc.), 1-(lower)alkyl-1-carbamoyl(lower)alkyl-4-pyrrolidinio [e.g. 1-(lower)alkyl-1-carbamoylmethyl-4-pyrrolidinio, etc.] and the like.

In the object compound (I) and the intermediary compounds mentioned below, it is to be understood that there may be one or more stereo-isomeric pair(s) such as optical isomers due to asymmetric carbon atom(s), and such isomers are also included within the scope of the present invention.
According to the present invention, the object compound (I) or pharmaceutically acceptable salts thereof can be prepared by the processes as illustrated by the following reaction schemes.
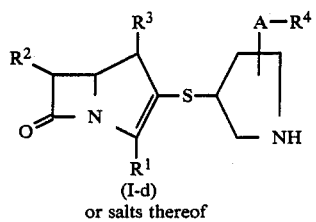

-continued

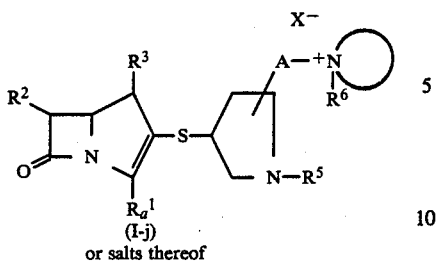
(I-j)
or salts thereof

Process 7:

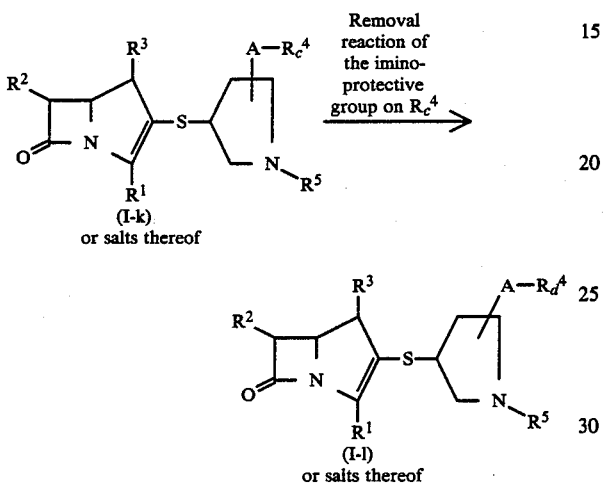

Process 8:

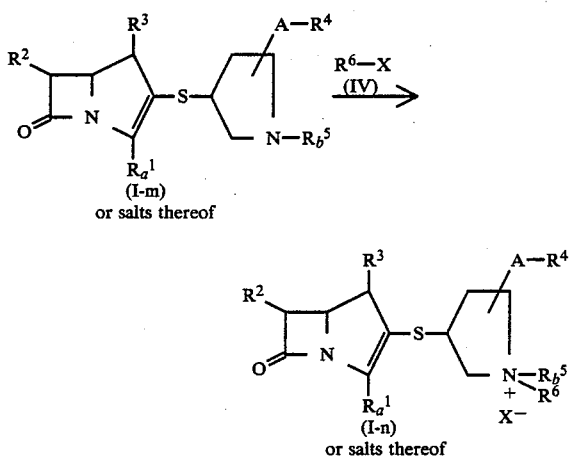

in which
R¹, R², R³, R⁴, R⁵ and A are each as defined above,
$R_a^1$ is protected carboxy,
$R_a^2$ is protected hydroxy(lower)alkyl,
$R_b^2$ is hydroxy(lower)alkyl,
$R_a^4$ is aliphatic heterocyclic group substituted by protected amino,
$R_b^4$ is aliphatic heterocyclic group substituted by amino,
$R_c^4$ is protected piperazinyl whose ring carbon atom(s) may be substituted by suitable substituent(s),
$R_d^4$ is piperazinyl whose ring carbon atom(s) may be substituted by suitable substituent(s),
$R_a^5$ is imino-protective group,
$R_b^5$ is lower alkyl, $R^6$ is lower alkyl or carbamoyl(lower)alkyl,
X is an acid residue, and
a group of the formula:

is N-containing aliphatic heterocyclic group which may be substituted by suitable substituent(s).

The compound (III) used in the process 1 is new and can be prepared, for example, by the following method or a conventional manner.

Method A:

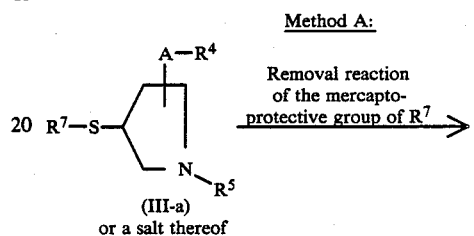

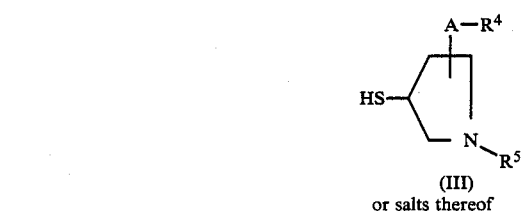

in which
R⁴, R⁵ and A are each as defined above, and
R⁷ is mercapto-protective group.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy (lower) alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.; lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-) isopropoxycarbonyloxyethyl ester, etc.], phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

Preferable example of the protected carboxy thus defined may be lower alkenyloxycarbonyl and phenyl(or nitrophenyl)(lower)alkoxycarbonyl, more preferable one may be $C_2$–$C_4$ alkenyloxycarbonyl and phenyl(or nitrophenyl)-($C_1$–$C_4$)alkoxycarbonyl, and the most preferable one may be 4-nitrobenzyloxycarbonyl and allyloxycarbonyl.

Suitable "hydroxy(lower)alkyl" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy($C_1$–$C_4$)alkyl and the most preferable one may be 1-hydroxyethyl.

Suitable "protected hydroxy(lower)alkyl" means aforementioned hydroxy(lower)alkyl, in which the hydroxy group is protected by a conventional hydroxy-protective group such as those mentioned in the explanation of imino-protective group as mentioned below, preferably lower alkenyloxycarbonyl and phenyl(or nitrophenyl)(lower)alkoxycarbonyl; ($C_6$–$C_{10}$)ar(lower)alkyl such as mono- or di- or triphenyl(lower)alkyl (e.g. benzyl, benzhydryl, trityl, etc.), etc.; trisubstituted silyl such as tri(lower)alkylsilyl (e.g. trimethylsilyl, triethylsilyl, isopropyldimethylsilyl, t-butyldimethylsilyl, diisopropylmethylsilyl, etc.), tri($C_6$–$C_{10}$)arylsilyl (e.g. triphenylsilyl, etc.), tris[($C_6$–$C_{10}$)ar(lower)alkyl]silyl, for example, tris[phenyl(lower)alkyl]silyl (e.g. tribenzylsilyl, etc.), etc.; and the like.

Preferable example of "protected hydroxy(lower)alkyl thus defined may be [phenyl(or nitrophenyl)(lower)alkoxy]cabonyloxy(lower)alkyl and [tri(lower)alkylsilyl]oxy(lower)alkyl, more preferable one may be [phenyl(or nitrophenyl)($C_1$–$C_4$)alkoxy]carbonyloxy($C_1$–$C_4$)alkyl [tri($C_1$–$C_4$)alkylsilyl]oxy($C_1$–$C_4$)alkyl, and the most preferable one may be 4-nitrobenzyloxycarbonyl.

Suitable "lower alkyl" may include straight or branched one such as methyl, ethyl, propyl, isopropyl, butyl, t-butyl, pentyl, hexyl, and the like, in which more preferable example may be $C_1$–$C_4$ alkyl and the most preferable one may be methyl and ethyl.

Suitable aliphatic heterocyclic group moiety of "aliphatic heterocyclic group which may be substituted by suitable substituent(s)", "aliphatic heterocyclic group substituted by protected amino" or "aliphatic heterocyclic group substituted by amino" may include saturated monocyclic or polycyclic heterocyclic group containing at least one hetero-atom such as oxygen, sulfur or nitrogen atom.

Preferable aliphatic heterocyclic group moiety may be saturated, 3 to 8-membered, more preferably 5 or 6-membered heteromonocyclic group containing 1 to 4 nitrogen atom(s) and optionally 1 to 2 oxygen atom(s), for example, pyrrolidinyl, imidazolidinyl, pyrozolidinyl, piperidyl, piperidino, piperazinyl, morpholinyl, morpholino, etc., wherein said aliphatic heterocyclic group may be substituted by one or more, preferably one or two suitable substituent(s) such as amino; protected amino in which the amino-protective group may be the same as those for the imino-protective group as mentioned below; carbamoyl; lower alkyl as mentioned above; oxo; lower alkylsulfonyl (e.g. methylsulfonyl, ethylsulfonyl, propylsulfonyl, isopropylsulfonyl, butylsulfonyl, pentylsulfonyl, hexylsulfonyl, etc.); hydroxy(lower)alkyl as mentioned above, in which the most preferable one may be hydroxymethyl and 2-hydroxyethyl; carbamoyl(lower)alkyl as mentioned below; and the like. And further, the imino-moiety thereof may be protected by a conventional imino-protective group as mentioned below.

Preferable example of "aliphatic heterocyclic group which may be substituted by suitable substituent(s)" may be:

imidazolidinyl (e.g. imidazolidin-1-yl, etc.); p0 oxoimidazolidinyl (e.g. 2-oxoimidazolidin-1-yl, etc.);

dioxoimidazolidinyl (e.g. 2,4-dioxoimidazolidin-1-yl, 2,5-dioxoimidazolidin-1-yl, etc.);

[(lower)alkylsulfonyl]oxoimidazolidinyl, more preferably [($C_1$–$C_4$)alkylsulfonyl]oxoimidazolidinyl (e.g. 3-methylsulfonyl-2-oxoimidazolidin-1-yl, etc.);

piperazinyl (e.g. piperazin-1-yl, etc.);

N-protected piperazinyl such as N-acylpiperazinyl, more preferably N-phenyl(or nitrophenyl)($C_1$–$C_4$)alkoxycarbonylpiperazinyl [e.g. 4-(4-nitrobenzyloxycarbonyl)piperazin-1-yl, etc.];

(lower)alkylpiperazinyl, more preferably ($C_1$–$C_4$)alkylpiperazinyl (e.g. 3-methylpiperazin-1-yl, 4-methylpiperazin-1-yl, etc.);

N-protected (lower)alkylpiperazinyl such as N-acyl(lower)alkylpiperazinyl, more preferably N-phenyl(or nitrophenyl)($C_1$–$C_4$)alkoxycarbonyl($C_1$–$C_4$)alkylpiperazinyl [e.g. 3-methyl-4-(4-nitrobenzyloxycarbonyl)piperazin-1-yl, etc.];

pyrrolidinyl (e.g. pyrrolidin-1-yl, etc.);

aminopyrrolidinyl (e.g. 3-aminopyrrolidin-1-yl, etc.);

protected aminopyrrolidinyl such as acylaminopyrrolidinyl, more preferably phenyl(or nitrophenyl)($C_1$–$C_4$)alkoxycarbonylaminopyrrolidinyl [e.g. 3-(4-nitrobenzyloxycarbonylamino)pyrrolidin-1-yl, etc.];

carbamoylpyrrolidinyl (e.g. 2-carbamoylpyrrolidin1-yl, etc.);

piperidinyl (e.g. piperidin-1-yl, etc.);

aminopiperidinyl (e.g. 4-aminopiperidin-1-yl, etc.);

protected aminopiperidinyl such as acylaminopiperidinyl, more preferably phenyl(or nitrophenyl)($C_1$–$C_4$)alkoxycarbonylaminopiperidinyl [e.g. 4-(4-nitrobenzyloxycarbonylamino)piperidin1-yl, etc.];

hydroxy(lower)alkylpyrrolidinyl, more preferably hydroxy($C_1$–$C_4$)alkylpyrrolidinyl (e.g. 2-hydroxymethylpyrrolidin-1-yl, etc.);

(lower)alkylpiperazinyl, more preferably ($C_1$–$C_4$)alkylpiperazinyl (e.g. 4-methylpiperazin-1-yl, etc.);

carbamoylpiperazinyl (e.g. 4-carbamoylpiperazin-1yl, etc.);
oxopiperazinyl (e.g. 3-oxopiperazin-1-yl, etc.);
morpholinyl (e.g. morpholino, etc.);
[(lower)alkyl]oxoimidazolidinyl, more preferably [($C_1$-$C_4$)alkyl]oxoimidazolidinyl [e.g. 3(or 4)-methyl-2-oxoimidazolidin-1-yl, 3-ethyl-2-oxoimidazolidin-1-yl, etc.];
[hydroxy(lower)alkyl]oxoimidazolidinyl, more preferably [hydroxy($C_1$-$C_4$)alkyl]oxoimidazolidinyl [e.g. 3-(2-hydroxyethyl)-2-oxoimidazolidin-1-yl, etc.].

Preferable example of "aliphatic heterocyclic group substituted by protected amino" may be:
protected aminopyrrolidinyl such as acylaminopyrrolidinyl, more preferably phenyl(or nitrophenyl)($C_1$-$C_4$)alkoxycarbonylaminopyrrolidinyl e.g. 3-(4-nitrobenzyloxycarbonylamino)pyrrolidin-1-yl, etc.];
protected aminopiperidinyl such as acylaminopiperidinyl, more preferably phenyl(or nitrophenyl)aminopiperidinyl [e.g. 4-(4-nitrobenzyloxycarbonylamino)piperidin-1-yl, etc.].

Preferable example of "aliphatic heterocyclic group substituted by amino" may be:
aminopyrrolidinyl (e.g. 3-aminopyrrolidin-1-yl, etc.);
aminopiperidinyl (e.g. 4-aminopiperidin-1-yl, etc.).

Suitable "protected piperazinyl whose ring carbon atom(s) may be substituted by suitable substituent(s)" may include N-protected piperazinyl such as N-acylpiperazinyl, whose ring carbon atom(s) may be substituted by one or more, more preferably, one or two suitable substituent(s) such as amino, protected amino as mentioned above, carbamoyl, lower alkyl as mentioned above, oxo, lower alkylsulfonyl as mentioned above, hydroxy(lower)alkyl as mentioned above, carbamoyl(lower)alkyl as mentioned above, and the like.

More preferable example of "protected piperazinyl whose ring carbon atom(s) may be substituted by suitable substituent(s)" may be N-phenyl(or nitrophenyl)($C_1$-$C_4$)alkoxycarbonyl($C_1$-$C_4$)alkylpiperazinyl [e.g. 3-methyl-4-(4-nitrobenzyloxycarbonyl)piperazin-1-yl, etc.].

Suitable "piperazinyl whose ring carbon atom(s) may be substituted by suitable substituent(s)" may include piperazinyl whose ring carbon atom(s) may be substituted by one or more, more preferably, one or two suitable substituent(s) such as amino, protected amino as mentioned above, carbamoyl, lower alkyl as mentioned above, oxo, lower alkylsulfonyl as mentioned above, hydroxy(lower)alkyl as mentioned above, carbamoyl(lower)alkyl as mentioned above, and the like.

More preferable example of "piperazinyl whose ring carbon atom(s) may be substituted by suitable substituent(s)" may be ($C_1$-$C_4$)alkylpiperazinyl [e.g. 3-methylpiperazin-1-yl, etc.].

Suitable "imino-protective group" may include acyl such as aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethyl carbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aromatic acyl may include $C_6$-$C_{10}$ aroyl (e.g. benzoyl, toluoyl, xyloyl, etc.), N-($C_6$-$C_{10}$)alkylcarbamoyl (e.g. N-phenylcarbamoyl, N-tolylcarbamoyl, N-naphthylcarbamoyl, etc.), $C_6$-$C_{10}$ arenesulfonyl (e.g. benzenesulfonyl, tosyl, etc.), and the like.

The aliphatic acyl substituted with aromatic group(s) may include aralkoxycarbonyl such as phenyl(lower)alkoxycarbonyl (e.g. benzyloxycarbonyl, phenethyloxycarbonyl, etc.), and the like.

These acyl groups may be further substituted with one or more suitable substituent(s) such as nitro, and the like, and preferable acyl having such substituent(s) may be nitroaralkoxycarbonyl (e.g. nitrobenzyloxycarbonyl, etc.), and the like.

Preferable example of "imino-protective group" thus defined may be lower alkenyloxycarbonyl and phenyl(or nitrophenyl)(lower)alkoxycarbonyl, more preferable one may be $C_2$-$C_4$ alkenyloxycarbonyl and phenyl(or nitrophenyl)($C_1$-$C_4$)alkoxycarbonyl, and the most preferable one may be 4-nitrobenzyloxycarbonyl.

Suitable "carbamoyl(lower)alkyl" may include straight or branched lower alkyl having carbamoyl group such as carbamoylmethyl, carbamoylethyl, carbamoylpropyl, 1-(carbamoylmethyl)ethyl, 1-carbamoyl-1-methylethyl, carbamoylbutyl, carbamoylpentyl, carbamoylhexyl, and the like, in which more preferable example may be carbamoyl($C_1$-$C_4$)alkyl and the most preferable one may be carbamoylmethyl.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$-$C_4$ alkylene and the most preferable one may be methylene.

Suitable "acid residue" may include an inorganic acid residue such as azido, halogen (e.g. chlorine, bromine, fluorine or iodine), and the like, an organic acid residue such as acyloxy (e.g. benzenesulfonyloxy, tosyloxy, methanesulfonyloxy, etc.), and the like, in which more preferable example may be halogen and the most preferable one may be iodine.

Suitable "mercapto-protective group" may include acyl as mentioned above, ($C_6$-$C_{10}$)ar(lower)alkyl such as mono or di- or triphenyl(lower)alkyl (e.g. benzyl, phenethyl, benzhydryl, trityl, etc.), and the like, in which preferable example may be lower alkanoyl, $C_6$-$C_{10}$ aroyl and triphenyl(lower)alkyl, more preferable one may be $C_1$-$C_4$ alkanoyl, $C_6$-$C_{10}$ aroyl and triphenyl($C_1$-$C_4$)alkyl, and the most preferable one may be benzoyl, acetyl and trityl.

In the definition of a group of the formula:

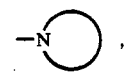

suitable "N-containing aliphatic heterocyclic group which may be substituted by suitable substituent(s)"

may include saturated 3 to 8 membered, more preferably 5 or 6 membered, heteromonocyclic group containing 1 to 4 nitrogen atom(s) and optionally 1 or 2 oxygen atom(s), for example, pyrrolidin-1-yl, imidazolidin-1-yl, pyrazolidin-1-yl, piperidino, piperazin-1-yl, morpholino, etc., wherein said aliphatic heterocyclic group may be substituted by one or more, preferably one or two, suitable substituent(s) such as amino, protected amino as mentioned above, carbamoyl, lower alkyl as mentioned above, oxo, lower alkylsulfonyl as mentioned above, hydroxy(lower)alkyl as mentioned above, carbamoyl(-lower)alkyl as mentioned above, and the like. And further, in case that said aliphatic heterocyclic group is imidazolidin-1-yl, pyrazolidin-1-yl or piperazin-1-yl, the imino-moiety thereof may be protected by a conventional imino-protective group as mentioned above.

Preferable example of "N-containing aliphatic heterocyclic group which may be substituted by suitable substituent(s)" thus defined may be:
imidazolidin-1-yl;
oxoimidazolidin-1-yl (e.g. 2-oxoimidazolidin-1-yl, etc.);
dioxoimidazolidin-1-yl (e.g. 2,4-dioxoimidazolidin-1-yl, etc.);
[(lower)alkylsulfonyl]oxoimidazolidin-1-yl, more preferably [(C₁-C₄)alkylsulfonyl]oxoimidazolidin. 1-yl (e.g. 3-methylsulfonyl-2-oxoimidazolidin-1-yl, etc.)
piperazin-1-yl;
N-protected piperazin-1-yl such as N-acylpiperazin-1-yl, more preferably N-phenyl(or nitrophenyl)(-C₁-C₄)alkoxycarbonylpiperazin-1-yl [e.g. 4-(4-nitrobenzyloxycarbonyl)piperazin-1-yl,
(lower)alkylpiperazin-1-yl, more preferably (C₁-C₄)alkylpiperazin-1-yl (e.g. 3-methylpiperazin-1-yl, 4-methylpiperazin-1-yl, etc.);
N-protected (lower)alkylpiperazin-1-yl such as N-acyl(-lower)alkylpiperazin-1-yl, more preferably N-phenyl(or nitrophenyl)(C₁-C₄)alkoxycarbonyl(C₁-C₄)alkylpiperazin-1-yl [e.g. 3-methyl-4-(4-nitrobenzyloxycarbonyl)piperazin-1-yl, etc.];
pyrrolidin-1-yl;
aminopyrrolidin-1-yl (e.g. 3-aminopyrrolidin-1-yl, etc.);
protected aminopyrrolidin-1-yl such as acylaminopyrrolidin-1-yl, more preferably phenyl(or nitrophenyl)(C₁-C₄)alkoxycarbonylaminopyrrolidin-1-yl [e.g. 3-(4-nitrobenzyloxycarbonylamino)pyrrolidin-1-yl, etc.];
carbamoylpyrrolidin-1-yl (e.g. 2-carbamoylpyrrolidin-1-yl, etc.);
piperidin-1-yl;
aminopiperidin-1-yl (e.g. 4-aminopiperidin-1-yl, etc.);
protected aminopiperidin-1-yl such as acylaminopiperidin-1-yl, more preferably phenyl(or nitrophenyl)(-C₁-C₄)alkoxycabonylaminopiperidin-1-yl [e.g. 4-(4-nitrobenzyloxycarbonylamino)piperidin-1-yl, etc.];
hydroxy(lower)alkylpyrrolidin-1-yl, more preferably hydroxy(C₁-C₄)alkylpyrrolidin-1-yl (e.g. 2-hydroxymethylpyrrolidin-1-yl, etc.);
(lower)alkylpiperazin-1-yl, more preferably (C₁-C₄)alkylpiperazin-1-yl (e.g. 4-methylpiperazin-1-yl, etc.);
carbamoylpiperadin-1-yl (e.g. 4-carbamoylpiperazin-1-yl, etc.);
oxopiperazin-1-yl (e.g. 3-oxopiperazin-1-yl, etc.);
morpholino;
[(lower)alkyl]oxoimidazolidin-1-yl, more preferably [(C₁-C₄)alkyl]oxoimidazolidin-1-yl [e.g. 3(or 4)-methyl-2-oxoimidazolidin-1-yl, 3-ethyl-2-oxoimidazolidin-1-yl, etc.];

[hydroxy(lower)alkyl]oxoimidazolidin-1-yl, more preferably [hydroxy(C₁-C₄)alkyl]oxoimidazolidin-1-yl [e.g. 3-(2-hydroxyethyl)-2-oxoimidazolidin-1-yl, etc.].

The processes for the preparation of the object compound (I) of the present invention are explained in detail in the following.

(1) Process 1

The compound (I) or salts thereof can be prepared by reacting the compound (II) or a reactive derivative at the oxo group thereof or salts thereof with the compound (III) or salts thereof.

Suitable salts of the compound (II) may be salts with bases such as those given for the compound (I).

The reactive derivative at the oxo group of the compound (II) can be represented by the following formula (II'), which is preferably used in this reaction and can be prepared by reacting the compound (II) or salts thereof with an acylating agent.

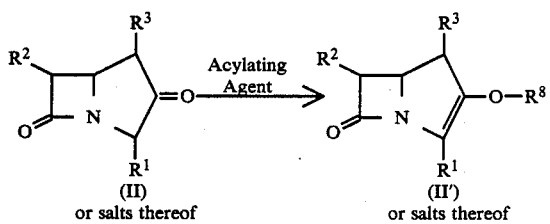

in which
R¹, R² and R³ are each as defined above, and
R⁸ is acyl as exemplified for the imino-protective group and further O,O-substituted phosphono derived from, for example, organic phosphoric acid mentioned hereinbelow.

Suitable acylating agents may include conventional ones which can introduce the acyl group as mentioned above into the compound (II), and preferable acylating agents may be organic sulfonic or phosphoric acid or its reactive derivative such as acid halide, acid anhydride, and the like, for example, arenesulfonyl halide (e.g. benzenesulfonyl chloride, p-toluenesulfonyl chloride, p-nitrobenzenesulfonyl chloride, p-bromobenzenesulfonyl chloride, etc.), arenesulfonic anhydride (e.g. benzenesulfonic anhydride, p-toluenesulfonic anhydride, p-nitrobenzenesulfonic anhydride, etc.), lower alkanesulfonyl halide which may have additional halogen (e.g. methanesulfonyl chloride, ethanesulfonyl chloride, trifluoromethanesulfonyl chloride, etc.), lower alkanesulfonic anhydride which may have halogen (e.g. methanesulfonic anhydride, ethanesulfonic anhydride, trifluoromethanesulfonic anhydride, etc.), di(lower)alkyl phosphorohaloridate (e.g. diethyl phosphorochloridate, etc.), diaryl phosphorohaloridate (e.g. diphenyl phosphorochloridate, etc.), and the like.

This acylation reaction is usually carried out in a conventional solvent which does not adversely influence the reaction such as acetone, dioxane, acetonitrile, chloroform, dichloromethane, hexamethylphosphoramide, dichloroethane, tetrahydrofuran, ethyl acetate, dimethylsulfoxide, N,N-dimethylformamide, pyridine, etc., or a mixture thereof.

When the acylating agent is used in a free acid form or its salt form in this reaction, the reaction is preferably carried out in the presence of a conventional condensing agent such as carbodiimide compound [e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.]; N,N'-carbonyldiimidazole, N,N'-carbonylbis(2-methylimidazole); keteneimine compound (e.g. pentamethyleneketene-N-cyclohexylimine, diphenylketene-N-cyclohexylimine, etc.); ethoxyacetylene; 1-alkoxy-1-chloroethylene; ethyl polyphosphate; isopropylpolyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; and the like.

This acylation reaction may be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compound [e.g. pyridine, picoline, lutidine, N,N-di(lower)alkylaminopyridine such as N,N-dimethylaminopyridine, etc.], quinoline, N-lower alkylmorpholine (e.g. N-methylmorpholine, etc.), N,N-di(lower)alkylbenzylamine (e.g. N,N-dimethylbenzylamine, etc.), alkali metal alkoxide (e.g. sodium methoxide, sodium ethoxide, potassium butoxide, etc.), and the like.

The reaction temperature of this acylation reaction is not critical and the reaction is usually carried out under from cooling to warming.

With regard to the compound (II), it is to be noted that the 3,7-dioxo-1-azabicyclo[3.2.0]heptane ring system of the following formula (IIA) is well known to lie to tautomeric relation with the 3-hydroxy-7-oxo-1-azabicyclo[3.2.0]hept-2-ene ring system of the following formula (IIB), and accordingly, it is to be understood that both of these ring systems are substantially the same.

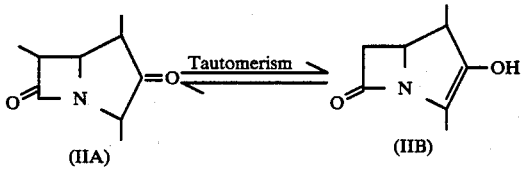

(IIA)  (IIB)

The compound (II') or salts thereof can be used with or without isolation for the subsequent reaction with the compound (III) or salts thereof.

Suitable salts of the compound (III) may be the same as those for the compound (I) and silver salt.

The reaction of the compound (II) or its reactive derivative or salts thereof with the compound (III) or salts thereof can be carried out in the presence of an organic or inorganic base such as those given in the explanation of the acylation reaction as stated above.

This reaction can be carried out in a conventional solvent which does not adversely influence the reaction such as those given in the explanation of the acylation reaction.

The reaction temperature is not critical and the reaction is usually carried out under from cooling to warming.

(2) Process 2

The compound (I-b) or salts thereof can be prepared by subjecting the compound (I-a) or salts thereof to removal reaction of the carboxy-protective group on $R_a^1$.

Suitable salts of the compounds (I-a) and (I-b) may be the same as those for the compound (I).

The present reaction is usually carried out by a conventional method such as hydrolysis, reduction, and the like.

(i) Hydrolysis

Hydrolysis is preferably carried out in the presence of a base or an acid. Suitable base may include an alkali-metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(lower)alkylsilyl, the hydrolysis can be carried out in the presence of tri(lower)alkylammonium halide (e.g. tributylammonium fluoride, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium(0), bis(dibenzylideneacetone)palladium(0), di[1,2-bis(diphenyl phosphino)ethane]palladium(0), tetrakis(triphenyl phosphite)palladium(0), tetrakis(triethyl phosphite)palladium(0), and the like.

The reaction can preferably be carried out in the presence of a scavenger of allyl group generated in situ, such as amine (e.g. morpholine, N-methylaniline, etc.), an activated methylene compound (e.g. dimedone, benzoylacetate, 2-methyl-3-oxovaleric acid, etc.), a cyanohydrin compound (e.g. α-tetrahydropyranyloxybenzyl cyanide, etc.), lower alkanoic acid or a salt thereof (e.g. formic acid, acetic acid, ammonium formate, sodium acetate, sodium 2-ethylhexanoate, etc.), N-hydroxysuccinimide, and the like.

This reaction can be carried out in the presence of a base such as lower alkylamine (e.g. butylamine, triethylamine, etc.), pyridine, and the like.

When palladium-ligand complex is used in this reaction, the reaction can preferably be carried out in the presence of the corresponding ligand (e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

The removal reaction can be selected according to the kind of carboxy-protective group to be removed.

In this reaction, in case that $R^4$ of the starting compound (I-a) is an intermolecular salt, then the object compound (I-b) can also be obtained as its intramolecular salt.

The present process includes within the scope thereof a case that the hydroxy- and/or imino- and/or amino-protective group(s) on $R^2$ and/or $R^4$, and/or imino-protective group of $R^5$ are removed at the same time during the reaction.

(3) Process 3

The compound (I-d) or salts thereof can be prepared by subjecting the compound (I-c) or salts thereof to removal reaction of the imino-protective group on $R_a^5$.

Suitable salts of the compounds (I-c) and (I-d) may be the same as those for the compound (I).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or imino- and/or amino-protective group(s) on $R^1$ and/or $R^4$ and/or hydroxy-protective group of $R^2$ are removed at the same time during the reaction.

(4) Process 4

The compound (I-f) or salts thereof can be prepared by subjecting the compound (I-e) or salts thereof to removal reaction of the hydroxy-protective group on $R_a^2$.

Suitable salts of the compounds (I-e) and (I-f) may be the same as those for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the hydroxy-protective group is tri(lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy- and/or hydroxy- and/or imino- and/or amino-protective group(s) on $R^1$ and/or $R^2$ and/or $R^4$ are removed at the same time during the reaction.

(5) Process 5

The compound (I-h) or salts thereof can be prepared by subjecting the compound (I-g) or salts thereof to removal reaction of the amino-protective group on $R_a^4$.

Suitable salts of the compound (I-h) may be the same as those for the compound (I).

Suitable salts of the compound (I-g) may be salts with bases such as those given for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy- and/or imino-protective group(s) on $R^1$ and/or $R^2$ and/or $R_a^4$, and/or the imino-protective group of $R^5$ are removed at the same time during the reaction.

(6) Process 6

The compound (I-j) or salts thereof can be prepared by reacting the compound (I-i) or salts thereof with the compound (IV).

Suitable salts of the compounds (I-i) and (I-j) may be the same as those for the compound (I).

This reaction is usually carried out in a conventional solvent which does not adversely influence the reaction such as water, dioxane, tetrahydrofuran, acetone, etc., or a mixture thereof.

The reaction temperature is not critical, and the reaction is usually carried out under from cooling to warming.

(7) Process 7

The compound (I-l) or salts thereof can be prepared by subjecting the compound (I-k) or salts thereof to removal reaction of the imino-protective group on $R_c^4$.

Suitable salts of the compounds (I-k) and (I-l) may be the same as those for the compound (I).

The reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy- and/or amino-protective group(s) on $R^1$ and/or $R^2$ and/or $R_c^4$, and/or the imino-protective group of $R^5$ are removed at the same time during the reaction.

(8) Process 8

The compound (I-n) or salts thereof can be prepared by reacting the compound (I-m) or salts thereof with the compound (IV).

Suitable salts of the compounds (I-m) and (I-n) may be the same as those for the compound (I-a).

This reaction is usually carried out in a conventional solvent which does not adversely influence the reaction such as water, dioxane, tetrahydrofuran, acetone, etc., or a mixture thereof.

The reaction temperature is not critical, and the reaction is usually carried out under from cooling to warming.

The object compounds (I), (I-b), (I-d), (I-f), (I-h), (I-j), (I-l) and (I-n) obtained according to the Processes 1 to 8, can be isolated and purified on a conventional manner, for example, extraction, precipitation, fractional crystallization, recrystallization, chromatography, and the like.

Method A for preparing the new starting compound (III) or salts thereof is explained in detail in the following.

Method A

The compound (III) or salts thereof can be prepared by subjecting the compound (III-a) or salts thereof to removal reaction of the mercapto-protective group.

Suitable salts of the compound (III-a) may be the same as those for the compound (III).

This removal reaction can be carried out by a conventional method as described below, which can be selected according to the kind of mercapto-protective group to be removed.

In case that the protective groups may be ar(lower)alkyl group, it can generally be removed by treating, for example, with a silver compound (e.g. silver nitrate, silver carbonate, etc.), or reacting with a mercapto compound (e.g. 2-mercaptoethanol, etc.) in the presence of an acid (e.g. trifluoroacetic acid, etc.).

The reaction with the silver compound as stated above is preferably carried out in the presence of an organic base (e.g. pyridine, etc.).

The resultant silver salt of compound (III) can be transformed into its alkalimetal salt, if necessary, by reacting with alkali metal halide (e.g. sodium iodide, potassium iodide, etc.).

Further, in case that the protective groups may be acyl group, it can generally be removed by solvolysis such as hydrolysis using an acid or base, alcoholysis using a base, and the like.

Suitable acid or base used in these reactions may be the same such as those given in the explanation of hydrolysis of the Process 2.

The reaction is usually carried out in a conventional solvent which does not adversely influence the reaction such as water, alcohol (e.g. methanol, ethanol, etc.), pyridine, N,N-dimethylformamide, etc., or a mixture thereof, and further in case that the base or acid to be used is in liquid, it can also be used as a solvent.

The alcoholysis is usually carried out in a conventional alcohol such as methanol, ethanol, and the like.

The reaction temperature is not critical and the reaction is usually carried out under from cooling to warming.

The object compound (I) and pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents.

In the present invention, the object compound (I) possessing more potent antimicrobial activity can be represented by the following formula:

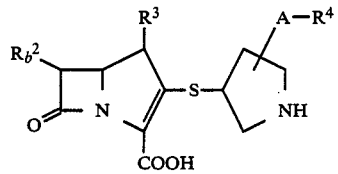

in which $R_b^2$, $R^3$, $R^4$ and A are each as defined above, and pharmaceutically acceptable salts thereof.

Particularly, the compound (I) possessing the most potent antimicrobial activity can be represented by the following formula:

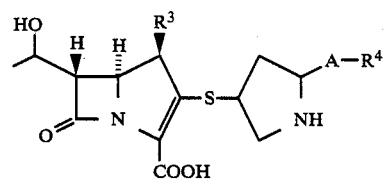

in which $R^3$, $R^4$ and A are each as defined above, and pharmaceutically acceptable salts thereof.

Now in order to show the utility of the object compound (I), the test data on antimicrobial activity of the representative compound of the compound (I) of this invention is shown in the following.

in vitro Antimicrobial Activity

Test Method in vitro Antimicrobial Activity was determined by the two-fold agar-plate dilution method as described blow.

One loopful of an overnight culture of a test strain in Trypticase-soy broth ($10^6$ viable cells per ml) was streaked on heart infusion agar (HI-agar) containing graded concentrations of the test compound, and the minimal inhibitory concentration (MIC) was expressed in terms of µg/ml after incubation at 37° C. for 20 hours.

Test Compound

The compound of Example 2.

Test Result

| Test Strain | MIC (µg/ml) |
|---|---|
| P. aeruginosa 26 | 0.39 |

For therapeutic administration, the object compound (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, a kind of diseases, a kind of the compound (I) to be applied, etc. In general, amount between 1 mg and about 4,000 mg or even more per day may be administered to a patient. An average single dose of about 1 mg, 10 mg, 50 mg, 100 mg, 250 mg, 500 mg, 1000 mg, 2000 mg, of the object compound (I) of the present invention may be used in treating diseases infected by pathogenic microorganisms.

The following Preparations and Examples are given for the purpose of illustrating this invention in more detail

PREPARATION 1

To a solution of (2S,4S)-4-acetylthio-2-hydroxymethyl-1-(4-nitrobenzyloxycarbonyl)pyrrolidine (15 g) in a mixture of methanol (150 ml) and tetrahydrofuran (150 ml) was added a 28% solution of sodium methoxide in methanol (8.95 ml) under ice-cooling and the mixture was stirred at the same temperature for 10 minutes. To the mixture was added triphenylmethyl chloride (12.39 g) on ice bath, followed by stirring at the same temperature for 1 hour. The precipitates were filtered off and the filtrate was evaporated in vacuo to give a residue. The residue was dissolved in ethyl acetate (200 ml), washed with water, dried over magnesium sulfate, and concentrated under reduced pressure to give a syrup. The syrup was chromatographed on silica gel (200 g) eluting with a mixture of dichloromethane and acetone (9:1 V/V). The fractions containing the desired compound were collected and evaporated in vacuo to give (2S,4S)-2-hydroxymethyl-1-(4-nitrobenzyloxycarbonyl)-4-(triphenylmethylthio)pyrrolidine (22.24 g).

NMR (CDCl$_3$, δ): 1.25–1.75 (2H, m), 5.15 (2H, s), 7.10–7.65 (17H, m), 8.28 (2H, d, J=9Hz)

PREPARATION 2

To a solution of (2S,4S)-2-hydroxymethyl-1-(4-nitrobenzyloxycarbonyl)-4-(triphenylmethylthio)pyrrolidine (10.7 g) in dichloromethane (100 ml) were added methanesulfonyl chloride (1.44 ml) and triethylamine (3.06 ml) under ice-cooling, and the mixture was stirred at the same temperature for 1 hour. The reaction mixture was washed with saturated aqueous sodium chloride, dried over magnesium sulfate and evaporated in vacuo to give a residue The residue was chromatographed on silica gel (150 g) eluting with a mixture of dichloromethane and acetone (40:1 V/V). The fractions containing the desired compound were collected and evaporated in vacuo to give (2S,4S)-2-(methanesulfonyloxy)methyl-1-(4-nitrobenzyloxycarbonyl)-4-(triphenylmethylthio)pyrrolidine (10.39 g).

NMR (CDCl$_3$, δ): 2.60–2.90 (2H, m), 2.92 (3H, s), 5.10–5.35 (2H, s), 7.15–7.60 (17H, m), 8.22 (2H, d, J=9 Hz)

PREPARATION 3-(1)

To a solution of (2S,4S)-2-(methanesulfonyloxy)methyl-1-(4-nitrobenzyloxycarbonyl)-4-(triphenylmethylthio)pyrrolidine (5.0 g) in dimethylformamide (90 ml) was added piperazine (2.0 g) and the mixture was stirred at 80°–90° C. for 5 hours. The reaction mixture was poured into ice-water (300 ml) and extracted twice with ethyl acetate (200 ml). The extract was washed with saturated aqueous sodium chloride, dried over magnesium sulfate and evaporated in vacuo. The resulting residue was chromatographed on silica gel (150 g) eluting with a mixture of chloroform and methanol (9:1 V/V). The fractions containing the desired compound were collected and evaporated in vacuo to give (2S,4S)-1-(4-nitrobenzyloxycarbonyl)-2-(piperazin-1-yl)methyl-4-(triphenylmethylthio)pyrrolidine (2.52 g).

NMR (CDCl$_3$, δ): 1.83 (2H, s), 2.10–2.63 (7H, m), 2.65–3.03 (7H, m), 3.66–3.98 (1H, m), 5.06–5.55 (2H, m), 7.05–7.66 (17H, m), 8.25 (2H, d, J=9 Hz)

PREPARATION 3-(2)

To a solution of (2S,4S)-2-(methanesulfonyloxy)methyl-1-(4-nitrobenzyloxycarbonyl)-4-(triphenylmethylthio)pyrrolidine (3.0 g) in dimethylformamide (30 ml) was added (2S)-2-carbamoylpyrrolidine (10.76 g) and the mixture was stirred at 100°–110° C. for 5 hours. The reaction mixture was poured into ice-water (100 ml). The resulting precipitates were collected by filtration and washed with water (100 ml). The precipitates were dissolved in ethyl acetate (80 ml) and the solution was washed with aqueous sodium chloride, dried over anhydrous magnesium sulfate and evaporated in vacuo to give a residue. The residue was chromatographed on silica gel (100 g) eluting with a mixture of dichloromethane and acetone (9:1 V/V). The fractions containing the desired compound were collected and evaporated in vacuo to give (2S,4S)-2-[(2S)-2-carbamoylpyrrolidin-1-yl]methyl-1-(4-nitrobenzyloxycarbonyl)-4-(triphenylmethylthio)pyrrolidine (0.78 g).

NMR (CDCl$_3$, δ): 5.06–5.33 (2H, m), 5.39–5.65 (1H, m), 7.05–7.67 (17H, m), 8.28 (2H, d, J=9 Hz)

PREPARATION 3-(3)

(2S,4S)-2-[(3S)-3-(t-Butoxycarbonylamino)pyrrolidin-1-yl]methyl-1-(4-nitrobenzyloxycarbonyl)-4-(triphenylmethylthio)pyrrolidine was obtained in 31.2% yield in substantially the same manner as that of Preparation 3-(1).

NMR (CDCl$_3$, δ): 1.45 (9H, s), 5.11 (2H, s), 7.18–7.60 (17H, m), 8.24 (2H, d, J=8 Hz)

PREPARATION 3-(4)

(2S,4S)-1-(4-Nitrobenzyloxycarbonyl)-2-(pyrrolidin-1-yl)-methyl-4-(triphenylmethylthio)pyrrolidine was obtained in 78.2% yield in substantially the same manner as that of Preparation 3-(1).

PREPARATION 3-(5)

(2S,4S)-2-[(4-Hydroxypiperizin-1-yl)methyl]-1-(4-nitrobenzyloxycarbonyl)-4-(triphenylmethylthio)pyrrolidine was obtained in 43.9% yield in substantially the same manner as that of Preparation 3-(1).

IR (Nujol): 1710–1690, 1605, 1520 cm$^{-1}$

NMR (CDCl$_3$, δ) 1.70–2.35 (2H, m), 2.60–3.15 (2H, m), 3.53–4.06 (3H, m), 5.15 (2H, s), 7.00–7.68 (17H, m), 8.28 (2H, d, J=9 Hz)

PREPARATION 3-(6)

(2S,4S)-2-[(3-Methylpiperazin-1-yl)methyl]-1-(4-nitrobenzyloxycarbonyl)-4-(triphenylmethylthio)pyrrolidine was obtained in 90.1% yield in substantially the same manner as that of Preparation 3-(1).

NMR (CDCl$_3$, δ): 1.02 (3H, d, J=6 Hz), 3.50–4.00 (2H, m), 5.10 (2H, s), 7.07–7.67 (17H, m), 8.25 (2H, d, J=9 Hz)

PREPARATION 3-7)

To a solution of (2S,4S)-2-(methanesulfonyloxy)methyl-1-(4-nitrobenzyloxycarbonyl)-4-(triphenylmethylthio)pyrrolidine (10.37 g) in dimethylformamide (100 ml) was added N-methylpiperazine (5.45 ml) and the mixture was stirred at 80°–90° C. for 5 hours. The reaction mixture was poured into ice-water (300 ml) and extracted twice with ethyl acetate (200 ml). The extract was washed with saturated aqueous sodium chloride, dried over magnesium sulfate and evaporated in vacuo. The resulting residue was chromatographed on silica gel (150 g) eluting with a mixture of chloroform and methanol (9:1 V/V). The fraction containing the desired compound were collected and evaporated in vacuo to give (2S,4S) 2-(4-methylpiperazin-1-yl)-1-(4-nitrobenzyloxy carbonyl)-4-(triphenylmethylthio)pyrrolidine (6.87 g).

NMR (CDCl$_3$, δ): 1.60–1.98 (1H, m), 2.22 (3H, s), 3.52–4.06 (1, m), 5.00–6.53 (2H, m), 6.95–7.60 (17H, m), 8.16 (2H, d, J=8 Hz)

PREPARATION 4

A solution of (2S,4S)-2-[(3S)-3-t-butoxycarbonylaminopyrrolidin-1-yl]methyl-1-(4-nitrobenzyloxycarbonyl)-4-(triphenylmethylthio)pyrrolidine (2.14 g) in a mixture of trifluoroacetic acid (10 ml) and anisole (1 ml) was stirred on ice-bath for 1 hour. The reaction mixture was evaporated in vacuo to give a residue. The residue was dissolved in ethyl acetate (100 ml) and the solution was washed with saturated aqueous sodium hydrogen carbonate (50 ml) and saturated aqueous sodium chloride, dried over magnesium sulfate, and evaporated in vacuo to give a residue of (2S,4S)-2-[(3S)-3-aminopyrrolidin-1-yl]methyl-1-(4-nitrobenzyloxycarbonyl)-4-(triphenylmethylthio)pyrrolidine. To a solution of the residue in a mixture of ethyl acetate (40 ml) and water (20 ml) was dropwise added a solution of 4-nitrobenzyloxycarbonyl chloride (1.06 g) in tetrahydrofuran (10 ml) under ice-cooling, keeping the pH between 8 and 9 with 1N aqueous sodium hydroxide solution. The mixture was stirred at the same temperature for 1 hour. To the reaction mixture was added ethyl acetate (50 ml). The solution was washed with saturated aqueous sodium chloride, dried over magnesium sulfate and evaporated in vacuo to give a residue. The residue was chromatographed on silica gel (100 g) eluting with a mixture of dichloromethane and acetone (9:1 V/V). The fractions containing the desired compound were collected and evaporated in vacuo to give (2S,4S)-1-(4-nitrobenzyloxycarbonyl)-2-[(3S)-3-(4-nitrobenzyloxycarbonylamino)pyrrolidin-1-yl]methyl-4-(triphenylmethylthio)pyrrolidine (1.89 g).

IR (Nujol): 1710–1690, 1600, 1520, 1345 cm$^{-1}$

NMR (CDCl$_3$, δ): 1.45–1.96 (4H, m), 2.00–3.03 (10H, m), 3.55–3.90 (1H, m), 4.00–4.40 (1H, m), 5.06–5.38 (4H, m), 7.10–7.65 (19H, m), 8.24 (4H, d, J=8 Hz)

PREPARATION 5

To a solution of (2S,4S)-2-[(4-hydroxypiperizin-1-yl)methyl]-1-(4-nitrobenzyloxycarbonyl)-4-(triphenylmethylthio)pyrrolidine (5.4 g) and triethylamine (1.54 ml) in dichloromethane (60 ml) was added methanesulfonyl chloride (0.72 ml) under ice-cooling and the mixture was stirred under the same condition for 1 hour. The reaction mixture was washed successively with aqueous sodium hydrogen carbonate and aqueous sodium chloride, dried over magnesium sulfate, and evaporated in vacuo to give (2S,4S)-2-[(4-methanesulfonyloxypiperizin-1-yl)methyl]-1-(4-nitrobenzyloxycarbonyl)-4-(triphenylmethylthio)pyrrolidine (6.06 g).

NMR (CDCl$_3$, δ): 3.00 (3H, s), 5.10–5.30 (2H, m), 7.13–7.66 (17H, m), 8.27 (2H, d, J=9 Hz)

PREPARATION 6

A solution of (2S,4S)-2-[(4-methanesulfonyloxypiperizin-1-yl)methyl]-1-(4-nitrobenzyloxycarbonyl)-4-(triphenylmethylthio)pyrrolidine (4.38 g) and sodium azide (1.19 g) in N,N-dimethylformamide (40 ml) was stirred at 90°–100° C. for 2 hours. The reaction mixture was poured into ice-water (300 ml) and extracted 3 times with saturated aqueous sodium chloride, dried over magnesium sulfate, and evaporated in vacuo. The resulting residue was chromatographed on silica gel (150 g) eluting with a mixture of dichloromethane and acetone (10:1 V/V). The fractions containing the desired compound were collected and evaporated in vacuo to give (2S,4S)-2-[(4-azidopiperizin-1-yl)methyl]-1-(4-nitrobenzyloxycarbonyl)-4-(triphenylmethylthio)pyrrolidine (2.51 g).

IR (Neat): 2110, 1700, 1525 cm$^{-1}$

NMR (CDCl$_3$, δ): 5.05–5.30 (2H, m), 7.20–7.65 (17H, m), 8.28 (2H, d, J=8 Hz)

PREPARATION 7

To a solution of (2S,4S) 2-[(4-azidopiperizin-1-yl)methyl]-1-(4-nitrobenzyloxycarbonyl)-4-(triphenylmethylthio)pyrrolidine (3.76 g) in pyridine (12 ml) was added triphenylphosphine (2.38 g) and the mixture was stirred at ambient temperature for 1 hour. To the reaction mixture was added concentrated ammonia (0.76 ml) and the mixture was allowed to stand overnight at ambient temperature. The reaction mixture was concentrated under reduced pressure and the residue was dissolved in ethyl acetate (100 ml). The solution was washed with saturated aqueous sodium chloride, dried over magnesium sulfate and evaporated in vacuo to give a residue. The residue was chromatographed on silica gel (100 g) eluting with a mixture of chloroform and methanol (10:1 V/V). The fractions containing the desired compound were collected and evaporated in vacuo to give (2S,4S)-2-[(4-aminopiperizin-1-yl)methyl]-1-(4-nitrobenzyloxycarbonyl)-4-(triphenylmethylthio)pyrrolidine (2.66 g).

NMR (CDCl$_3$, δ): 3.60–4.06 (2H, m), 5.03–5.28 (2H, m), 7.06–7.63 (17H, m), 8.25 (2H, d, J=9 Hz)

PREPARATION 8-(1)

To a solution of (2S,4S)-1-(4-nitrobenzyloxycarbonyl)-2-(piperazin-1-yl)methyl-4-(triphenylmethylthio)pyrrolidine (2.51 g) and triethylamine (0.73 ml) in dichloromethane (25 ml) was added 4-nitrobenzyloxycarbonyl chloride (0.91 g) under ice-cooling and the mixture was stirred at the same temperature for 1 hour. The reaction mixture was washed with saturated aqueous sodium chloride, dried over magnesium sulfate and evaporated in vacuo to give a residue. The residue was chromatographed on silica gel (100 g) eluting with a mixture of dichloromethane and acetone (20:1 V/V). The fractions containing the desired compound were collected and evaporated in vacuo to give (2S,4S)-1-(4-nitrobenzyloxycarbonyl)-2-[4-(4-nitrobenzyloxycarbonyl)piperazin-1-yl]methyl-4-(triphenylmethylthio)pyrrolidine (2.77 g).

IR (Nujol): 1690, 1605, 1520, 1345, 1240 cm$^{-1}$
NMR (CDCl$_3$, δ): 5.05–5.35 (4H, m), 7.10–7.60 (19H, m), 8.26 (4H, d, J=4 Hz)

PREPARATION 8-(2)

(2S ,4S) 2-[{4-(4-Nitrobenzyloxycarbonylamino)-piperizin-1-yl}methyl]-1-(4-nitrobenzyloxycarbonyl)-4-(triphenylmethylthio)pyrrolidine was obtained in 95.8% yield in substantially the same manner as that of Preparation 8-(1).

NMR (CDCl$_3$, δ): 1.20–1.64 (2H, m), 4.66–4.83 (1H, m), 5.06–5.40 (4H, m), 7.10–7.68 (19H, m), 8.22 (4H, d, J=9 Hz)

PREPARATION 8-(3)

(2S ,4S) 2-[3-Methyl-4-(4-nitrobenzyloxycarbonyl)-piperazin-1-yl]methyl-1-(4-nitrobenzyloxycarbonyl)-4-(triphenylmethylthio)pyrrolidine was obtained in 75.5% yield in substantially the same manner as that of Preparation 8-(1).

NMR (CDCl$_3$, δ): 1.10–1.43 (3H, m), 5.08 (2H, s), 5.21 (2H, s), 7.00–7.66 (17H, m), 8.14 (4H, d, J=9 Hz)

PREPARATION 9-(1)

To a solution of (2S,4S)-1- (4-nitrobenzyloxycarbonyl)-2-[4-(4-nitrobenzyloxycarbonyl)piperazin-1-yl]methyl-4-(triphenylmethylthio)pyrrolidine (2.76 g) in trifluoroacetic acid (15 ml) was added 2-mercaptoethanol (0.31 ml) under ice-cooling and the mixture was stirred at ambient temperature for 10 minutes. The reaction mixture was concentrated under reduced pressure to give a residue. The residue was dissolved in toluene (20 ml) and the solution was evaporated in vacuo to give a syrup. The syrup was dissolved in ethyl acetate (60 ml) and washed successively with saturated aqueous sodium hydrogen carbonate (30 ml) and saturated aqueous sodium chloride, dried over magnesium sulfate, and concentrated under reduced pressure to give a residue. The residue was chromatographed on silica gel (100 g) eluting with a mixture of dichloromethane and acetone (9:1 V/V). The fractions containing the desired compound were collected and evaporated in vacuo to give (2S,4S)-4-mercapto-1-(4-nitrobenzyloxycarbonyl)-2-[4-(4-nitrobenzyloxycarbonyl)piperazin-1-yl]methylpyrrolidine (0.93 g).

IR (Neat) 1710–1690, 1610, 1520, 1350, 1245 cm$^{-1}$
NMR (CDCl$_3$, δ): 1.60–2.08 (2H, m), 2.30–3.00 5.24 (4H, s), 7.50 (4H, d, J=8 Hz), 8.25 (4H, d, J=8 Hz)

PREPARATION 9-(2)

To a solution of (2S,4S)-2-[(2S)-2-carbamoylpyrrolidin-1-yl]methyl-1-(4-nitrobenzyloxycarbonyl)-4-(triphenylmethylthio)pyrrolidine (1.76 g) in trifluoroacetic acid (10 ml) was added 2-mercaptoethanol (0.38 ml) under ice-cooling and the mixture was stirred at ambient temperature for 15 minutes. The reaction mixture was concentrated under reduced pressure to give a residue The residue was dissolved in toluene (10 ml) and the solution was evaporated in vacuo. The resulting residue was dissolved in ethyl acetate (50 ml), washed successively with saturated aqueous sodium hydrogen carbonate (20 ml) and saturated aqueous sodium chloride, dried over anhydrous magnesium sulfate, and evaporated in vacuo to give a residue. The residue was chromatographed on silica gel (100 g) eluting with a mixture of dichloromethane and acetone (9:1 V/V). The fractions containing the desired compound were collected and evaporated in vacuo to give (2S,4S)-2-[(2S)-2-carbamoylpyrrolidin-1-yl]methyl-4-mercapto-1-(4-nitrobenzyloxycarbonyl)pyrrolidine (0.58 g).

IR (Neat): 1690–1680, 1610, 1525, 1430, 1410, 1350 cm$^{-1}$
NMR (CDCl$_3$, δ): 1.43–1.96 (4H, m), 3.80–4.22 (2H, m), 5.16 (2H, s), 5.36–5.56 (1H, m), 7.50 (2H, d, J=9 Hz), 8.22 (2H, d, J=9 Hz)

PREPARATION 9-(3)

(2S,4S )-4-Mercapto-1-(4-nitrobenzyloxycarbonyl-2-[(3S)-3-(4-nitrobenzyloxycarbonylamino)pyrrolidin-1-yl]methylpyrrolidine was obtained in 55.9% yield in substantially the same manner as that of Preparation 9-(1).

NMR (CDCl$_3$, δ): 5.23 (4H, s), 7.57 (4H, d, J=9 Hz), 8.28 (4H, d, J=9 Hz)

PREPARATION 9-(4)

(2S,4S)-4-Mercapto-1-(4-nitrobenzyloxycarbonyl)-2-(pyrrolidin-1-yl)methylpyrrolidine was obtained in 67.7% yield in substantially the same manner as that of Preparation 9-(1).

NMR (CDCl$_3$, δ): 1.80–2.35 (6H, m), 5.23 (2H, s), 7.53 (2H, d, J=8 Hz), 8.26 (2H, d, J=8 Hz)
Mass: 365 (M+)

PREPARATION 9-(5)

(2S,4S)-4-Mercapto-2-[{4-(4-nitrobenzyloxycarbonylamino)piperizin-1-yl}methyl]-1-(4-nitrobenzyloxycarbonyl)pyrrolidine was obtained in 31.6% yield in substantially the same manner as that of Preparation 9-(1).

NMR (CDCl$_3$, δ): 4.60–4.90 (1, m), 5.13–5.28 (4H, m), 7.52 (4H, d, J=9 Hz), 8.25 (4H, d, J=9 Hz)

PREPARATION 9-(6)

(2S,4S)-4-Mercapto-2-[3-methyl-4-(4-nitrobenzyloxycarbonyl)piperazin-1-yl]methyl-1-(4-nitrobenzyloxycarbonyl)pyrrolidine was obtained in 50.9% yield in substantially the same manner as that of Preparation 9-(1).

IR (Neat): 1710–1690, 1610, 1525, 1220 cm$^{-1}$

NMR (CDCl$_3$, δ): 1.28 (2H, d, J=6 Hz), 1.70–1.86 (1, m), 5.24 (4H, s), 7.49 (4H, d, J=9 Hz), 8.25 (4H, d, J=9 Hz)

PREPARATION 9-(7)

To a solution of (2S,4S)-2-(4-methylpiperazin-1-yl)methyl-1-(4-nitrobenzyloxycarbonyl)-4-(triphenylmethylthio)pyrrolidine (6.85 g) in trifluoroacetic acid (35 ml) was added 2-mercaptoethanol (1.13 ml) under ice-cooling and the mixture was stirred at ambient temperature for 15 minutes. The reaction mixture was concentrated in vacuo. The resulting residue was dissolved in toluene (40 ml) and the solution was evaporated in vacuo to give a syrup. The syrup was dissolved in ethyl acetate (100 ml) and washed successively with saturated aqueous sodium hydrogen carbonate and saturated aqueous sodium chloride, dried over magnesium sulfate, and evaporated in vacuo to give a residue. The residue was chromatographed on silica gel (100 g) eluting with a mixture of dichloromethane and acetone (10:1 V/V). The fractions containing the desired compound were collected and evaporated in vacuo to give (2S,4S)-4-mercapto-2-(4-methylpiperazin-1-yl)methyl-1-(4-nitrobenzyloxycarbonyl)pyrrolidine (2.14 g).

NMR (CDCl$_3$, δ), 1.46–2.10 (2H, m), 2.28–2.66 (2H, m), 2.72 (3H, s), 3.80–4.20 (2H, m), 5.16 (2H, s), 7.45 (2H, d, J=8 Hz), 8.13 (2H, d, J=8 Hz)

PREPARATION 10

To a solution of (2S,4R)-2-aminomethyl-4-t-butyldimethylsilyloxy-1-(4-nitrobenzyloxycarbonyl)pyrrolidine (5 g) and triethylamine (1.87 ml) in N,N-dimethylformamide (50 ml) was dropwise added ethyl bromoacetate (1.49 ml) at ambient temperature with stirring. The mixture was stirred at 40° C. for 30 minutes and then allowed to stand at ambient temperature for 6 hours. The reaction mixture was poured into saturated aqueous sodium chloride (100 ml) and extracted twice with ethyl acetate (100 ml). The extract was washed with saturated aqueous sodium chloride, dried over magnesium sulfate and evaporated in vacuo. The resulting residue was subjected to a column chromatography on silica gel (100 g) eluting with a mixture of dichloromethane and acetone (20:1 V/V). The fractions containing the desired compound were collected and evaporated in vacuo to give (2S,4R)-4-t-butyldimethylsilyloxy-2-[(ethoxycarbonylmethyl)aminomethyl]-1-(4-nitrobenzyloxycarbonyl)pyrrolidine (3.52 g).

IR (Neat): 1740, 1710, 1610, 1530, 1350, 1260 cm$^{-1}$

NMR (CDCl$_3$, δ): 0.06 (6H, s), 0.83 (9H, s), 1.24 (3H, t, J=7 Hz), 1.88–2.20 (2H, m), 5.24 (2H, s), 7.40–7.65 (2H, m), 8.23 (2H, d, J=8 Hz)

PREPARATION 11

To a solution of (2S,4R)-4-t-butyldimethylsilyloxy-2-[(ethoxycarbonylmethyl)aminomethyl]-1-(4-nitrobenzyloxycarbonyl)pyrrolidine (6.55 g) in a mixture of tetrahydrofuran (80 ml) and water (40 ml) were added concentrated hydrochloric acid (1.05 ml) and a solution of potassium cyanate (1.61 g) in water (10 ml) and the mixture was stirred at 50°–60° C. for 1 hour. To a reaction mixture was added ethyl acetate (100 ml). The organic layer was separated, washed with saturated aqueous sodium chloride, dried over anhydrous magnesium sulfate and evaporated in vacuo. The resulting residue was chromatographed on silica gel (150 g) eluting with a mixture of dichloromethane and acetone (9:1 V/V). The fractions containing the desired compound were collected and evaporated in vacuo to give (2S,4R)-4-t-butyldimethylsilyloxy-2-(N-carbamoyl-N-ethoxycarbonylmethyl)aminomethyl-1-(4-nitrobenzyloxycarbonyl)pyrrolidine (5.24 g).

NMR (CDCl$_3$, δ): 0.06 (6H, s), 0.85 (9H, s), 1.23 (3H, t, J=7 Hz), 1.70–2.30 (2H, m), 2.75–3.25 (1H, m), 3.30–3.60 (2H, m), 3.65–4.50 (6H, m), 5.25 (2H, s), 5.52 (1, broad s), 7.45 (2H, d, J=8 Hz), 8.25 (2H, d, J=8 Hz)

PREPARATION 12

A solution of (2S,4R)-4-t-butyldimethylsilyloxy-2-(N-carbamoyl-N-ethoxycarbonylmethyl)aminomethyl-1-(4-nitrobenzyloxycarbonyl)pyrrolidine (5.22 g) in a mixture of aqueous 1N sodium hydroxide solution (15 ml) and tetrahydrofuran (50 ml) was stirred at 35°–40° C. for 30 minutes. To the reaction mixture was added ethyl acetate (50 ml) and the organic layer was separated, washed with saturated aqueous sodium chloride, dried over magnesium sulfate, and evaporated in vacuo. The resulting residue was chromatographed on silica gel (100 g) eluting with a mixture of dichloromethane and acetone (9:1 V/V). The fractions containing the desired compound were collected and evaporated in vacuo to give (2S,4R)-4-t-butyldimethylsilyloxy-2-(2,4-dioxoimidazolidin-1-yl)methyl-1-(4-nitrobenzyloxycarbonyl)pyrrolidine (4.78 g).

IR (Nujol): 1765, 1735, 1675, 1610, 1525, 1350, 1140 cm$^{-1}$

NMR (CDCl$_3$, δ): 0.06 (6H, s), 0.84 (9H, s), 1.70–2.10 (2H, m), 3.28–4.50 (8H, m), 5.22 (2H, s), 7.52 (2H, d, J=8 Hz), 8.24 (2H, d, J=8 Hz), 8.35–8.70 (1H, m)

PREPARATION 13

A solution of (2S,4R)-4-t-butyldimethylsilyloxy-2-(2,4-dioxoimidazolidin-1-yl)methyl-1-(4-nitrobenzyloxycarbonyl)pyrrolidine (4.78 g) in a mixture of methanol (100 ml) and concentrated hydrochloric acid (1.62 ml) was stirred at ambient temperature for 1 hour. The reaction mixture was evaporated in vacuo. The resulting residue was dissolved in toluene (30 ml) and the solution was concentrated under reduced pressure to give a residue. The residue was chromatographed on silica gel (60 g) eluting with a mixture of dichloromethane and acetone (2:1 V/V). The fractions containing the desired compound were collected and evaporated in vacuo to give (2S,4R)-2-(2,4-dioxoimidazolidin-1-yl)methyl-4-hydroxy-1-(4-nitrobenzyloxycarbonyl)pyrrolidine (3.27 g).

IR (Nujol) 1720, 1530, 1090 cm$^{-1}$

NMR (CDCl$_3$, δ): 1.95–2.30 (2H, m), 5.26 (2H, s), 7.55 (2H, d, J=8 Hz), 8.27 (2H, d, J=8 Hz)

EI Mass: 378 (M+)

PREPARATION 14

To a suspension of sodium borohydride (0.42 g) in tetrahydrofuran (20 ml) was dropwise added boron trifluoride etherate (5.25 ml) under ice-cooling and the mixture was stirred at the same temperature for 10 minutes. To this solution was added a solution of (2S,4R)-2-(2,4-dioxoimidazolidin-1-yl)methyl-4-hydroxy-1-(4-nitrobenzyloxycarbonyl)pyrrolidine (2.1 g) in tetrahydrofuran (10 ml) under ice-cooling and the mixture was stirred at ambient temperature for 3 hours. To the reaction mixture was dropwise added methanol (5 ml) and the mixture was filtered off. The filtrate was evaporated in vacuo. The resulting residue was dissolved in methanol (30 ml) and 1.7 !1 hydrogen chloride-methanol solution (6 ml) and the solution was allowed to stand overnight at ambient temperature. The reaction mixture was evaporated in vacuo and dissolved in ethyl acetate (60 ml). The solution was washed successively with saturated aqueous sodium hydrogen carbonate and saturated aqueous sodium chloride, dried over magnesium sulfate, and evaporated in vacuo to give precipitates. The precipitates were washed with ethyl acetate (20 ml) and air-dried to give (2S,4R)-4-hydroxy-1-(4-nitrobenzyloxycarbonyl)-2-(2-oxoimidazolidin-1-yl)methyl pyrrolidine (1.39 g).

IR (Nujol): 1695, 1660, 1605, 1525, 1500, 1350 cm$^{-1}$

NMR (DMSO-d$_6$, $\delta$): 1.75–2.15 (2H, m), 3.00–3.60 (8H, m), 3.90–4.45 (2H, m), 4.96 (1, d, J=3 Hz), 5.25 (2H, s), 6.31 (1, s), 7.70 (2H, broad d, J=7 Hz), 8.29 (2H, d, J=8 Hz)

PREPARATION 15-(1)

To a solution of (2S,4R)-4-hydroxy-1-(4-nitrobenzyloxycarbonyl)-2-(2-oxoimidazolidin-1-yl)methyl pyrrolidine (1.60 g), pyridine (0.43 ml) and N,N-dimethylaminopyridine (0.54 g) in dichloromethane (20 ml) was added methanesulfonyl chloride (0.37 ml) under ice-cooling and the mixture was stirred under the same condition for 1 hour and then allowed to stand at ambient temperature for 3 hours. The reaction mixture was washed successively with 1N hydrochloric acid, aqueous sodium hydrogen carbonate and aqueous sodium chloride, dried over magnesium sulfate, and evaporated in vacuo. The resulting residue was chromatographed on silica gel (100 g) eluting with a mixture of chloroform and methanol (9:1 V/V). The fractions containing the desired compound were collected and evaporated in vacuo to give (2S,4R)-4-methanesulfonyloxy-1-(4-nitrobenzyloxycarbonyl)-2-(2-oxoimidazolidin-1-yl)methylpyrrolidine (1.90 g).

IR (Neat): 1720–1690, 1610, 1525, 1495, 1350, 1275 cm$^{-1}$

NMR (CDCl$_3$, $\delta$): 1.75–2.06 (1H, m), 2.27–2.56 (2H, m), 3.03 (3H, s), 3.16–4.47 (9H, m), 4.80–5.20 (1H, m), 5.30 (2H, s), 7.56 (2H, d, J=8 Hz), 8.24 (2H, d, J=8 Hz)

PREPARATION 15-(2)

(2S,4R)-2-(3-Methylsulfonyl-2-oxoimidazolidin-1-yl)methyl-4-methanesulfonyloxy-1-(4-nitrobenzyloxycarbonyl)pyrrolidine was obtained in 96.7% yield in substantially the same manner as that of Preparation 15-(1) except for using triethylamine in place of pyridine.

NMR (CDCl$_3$, $\delta$): 2.00–2.60 (2H, m), 3.03 (3H, s) 3.26 (3H, s), 5.26 (2H, s), 7.56 (2H, broad d, J=8 Hz), 8.28 (2H, d, J=8 Hz)

PREPARATION 15-(3)

(2S,4R)-2-(2,4-dioxoimidazolidin-1-yl)methyl-4-methanesulfonyloxy-1-(4-nitrobenzyloxycarbonyl)pyrrolidine was obtained in 37.6% yield in substantially the same manner as that of Preparation 15-(1).

IR (Nujol): 1720–1690, 1610, 1530–1520 cm$^{-1}$

NMR (CDCl$_3$, $\delta$): 2.10–2.70 (1H, m), 3.06 (3H, s), 3.35–4.50 (8H, m), 5.29 (3H, broad s), 7.56 (2H, d, J=8 Hz), 8.10–8.30 (1H, m), 8.28 (2H, d, J=8 Hz)

PREPARATION 16-(1)

To a solution of (2S,4R)-4-methanesulfonyloxy-1-(4-nitrobenzyloxycarbonyl)-2-(2-oxoimidazolidin-1-yl)methylpyrrolidine (1.84 g) in dimethylformamide (40 ml) was added potassium thioacetate (0.95 g) and the mixture was stirred at 70°–80° C. for 2 hours. The reaction mixture was poured into ice-water (200 ml) and extracted 3 times with ethyl acetate (100 ml). The extract was washed with saturated aqueous sodium chloride, dried over anhydrous magnesium sulfate and evaporated in vacuo. The resulting residue was chromatographed on silica gel (100 g) eluting with a mixture of chloroform and methanol (9:1 V/V). The fractions containing the desired compound were collected and evaporated in vacuo to give (2S,4S)-4-acetylthio-1-(4-nitrobenzyloxycarbonyl)-2-(2-oxoimidazolidin-1-yl)methylpyrrolidine (1.23 g).

NMR (CDCl$_3$, $\delta$): 1.50–1.80 (2H, m), 2.33 (3H, s), 5.25 (2H, s), 7.57 (2H, d, J=8 Hz), 8.28 (2H, d, J=8 Hz)

PREPARATION 16-(2)

(2S,4S)-4-Acetylthio-2-(3-methylsulfonyl-2-oxoimidazolidin-1-yl)methyl-1-(4-nitrobenzyloxycarbonyl)pyrrolidine was obtained in 56.9% yield in substantially the same manner as that of Preparation 16-(1).

IR (Nujol): 1730, 1710–1700, 1610, 1525, 1350 cm$^{-1}$

NMR (CDCl$_3$, $\delta$): 1.65–2.05 (1, m), 2.20 (3H, s), 3.27 (3H, s), 3.25–4.35 (11, m), 5.25 (2H, s), 7.56 (2H, d, J=8Hz), 8.26 (2H, d, J=8Hz)

PREPARATION 16-(3)

(2S,4S)-4-Acetylthio-2-(2,4-dioxoimidazolidin-1-yl)methyl-1-(4-nitrobenzyloxycarbonyl)pyrrolidine was obtained in 87.4% yield in substantially the same manner as that of Preparation 16-(1).

IR (Nujol): 1765, 1720, 1690, 1650, 1610, 1525, 1350 cm$^{-1}$

NMR (CDCl$_3$, $\delta$): 1.60–2.10 (1, m), 5.20 (2H, s), 7.54 (2H, d, J=8 Hz), 8.25 (2H, d, J=8 Hz)

PREPARATION 17-(1)

To a solution of (2S,4S)-4-acetylthio-1-(4-nitrobenzyloxycarbonyl)-2-(2-oxoimidazolidin-1-yl)methylpyrrolidine (1.22 g) in methanol (20 ml) was added 28% sodium methoxide in methanol solution (0.61 ml) on ice-bath under atmospheric pressure of nitrogen and the mixture was stirred at the same condition for 30 minutes. To a reaction mixture was added acetic acid (0.17 ml) and evaporated in vacuo. The resulting residue was dissolved in ethyl acetate (50 ml) and the solution was washed twice with saturated aqueous sodium chloride, dried over magnesium sulfate, and evaporated in vacuo. The resulting residue was chromatographed on silica gel (150 g) eluting with a mixture of chloroform and methanol (9:1 V/V). The fractions containing the desired compound were collected and evaporated in vacuo to give (2S,4S)-4-mercapto-1-(4-nitrobenzyloxycarbonyl)-2-(2-oxoimidazolidin-1-yl)methylpyrrolidine (0.76 g).

IR (Neat): 1710–1690, 1610, 1525, 1500, 1350, 1280 cm$^{-1}$

NMR (CDCl$_3$, $\delta$): 1.60–2.05 (2H, m), 2.33–3.10 (2H, m), 3.10–3.80 (7H, m), 3.85–4.33 (2H, m), 4.85–5.16 (1, m), 5.24 (2H, s), 7.56 (2H, d, J=8 Hz), 8.26 (2H, d, J=8 Hz)

EI Mass: 347 (M+-33)

PREPARATION 17-(2)

(2S,4S)-4-Mercapto-2-(3-methylsulfonyl-2-oxoimidazolidin-1-yl)methyl-1-(4-nitrobenzyloxycarbonyl)pyrrolidine was obtained in 66.4% yield in substantially the same manner as that of Preparation 17-(1).

IR (Neat): 1720–1690, 1610, 1530–1520 cm$^{-1}$
NMR (CDCl$_3$, δ): 2.35–2.75 (1, m), 3.10–4.30 (13H, m), 5.24 (2H, s), 7.56 (2H, d, J=8 Hz), 8.26 (2H, d, J=8 Hz)

PREPARATION 17-(3)

(2S,4S)-2-(2,4-Dioxoimidazolidin-1-yl)methyl-4-mercapto-1-(4-nitrobenzyloxycarbonyl)pyrrolidine was obtained in 58.4% yield in substantially the same manner as that of Preparation 17-(1).

IR (Nujol): 1765, 1720–1680, 1605, 1520 cm$^{-1}$
NMR (CDCl$_3$, δ): 3.00–4.35 (8H, m), 5.52 (2H, s), 7.48 (2H, d, J=8 Hz), 8.00–8.20 (1, m), 8.23 (2H, d, J=8 Hz)

PREPARATION 18

To a mixture of N,N-dimethylformamide (0.6 ml) and tetrahydrofuran (1.2 ml) was added dropwise phosphorus oxychloride (0.58 ml) at −5° C. and the mixture was stirred at 5° C. for 5 minutes. To the mixture was added a solution of (2S,4R)-4-methanesulfonyloxy-1-(4-nitrobenzyloxycarbonyl)proline (2.0 g) in tetrahydrofuran (20 ml) under ice-cooling. The solution was stirred at the same temperature for 30 minutes. To a solution were added ethylene urea (2.22 g) and concentrated sulfuric acid (0.035 ml), and the mixture was stirred at 45°–50° C. for 3 hours. Ethyl acetate (100 ml) and water (40 ml) was poured into the reaction mixture. The organic layer was washed with saturated aqueous sodium chloride, dried over anhydrous magnesium sulfate, and evaporated in vacuo to give a residue. The residue was chromatographed on silica gel (100 g) eluting with a mixture of chloroform and methanol (9:1, V/V). The fractions containing the desired compound were collected and evaporated in vacuo to give (2S,4R)-4-methanesulfonyloxy-1-(4-nitrobenzyloxycarbonyl)-2-(2-oxoimidazolidin-1-yl)carbonylpyrrolidine (1.98 g).

IR (Neat): 1710–1680, 1605, 1520–1510 cm$^{-1}$
NMR (CDCl$_3$, δ): 2.06–2.46 (1H, m), 2.58–3.05 (1H, m), 3.05 (3H, s), 3.26–4.25 (6H, m), 4.95–5.44 (3H, m), 5.46–5.90 (2H, m), 7.43 (2H, d, J=8 Hz), 7.50 (2H, d, J=8 Hz), 8.22 (4H, d, J=8 Hz)

PREPARATION 19

To a solution of sodium borohydride (0.32 g) in tetrahydrofuran (20 ml) was added dropwise boron trifluoride etherate (6.0 ml) under ice-cooling and the mixture was stirred at the same temperature for 10 minutes. To the mixture was added a solution of (2S,4R)-4-methanesulfonyloxy-1(4-nitrobenzyloxycarbonyl)-2-(2-oxoimidazolidin-1-yl)carbonylpyrrolidine (2.0 g) in tetrahydrofuran (10 ml) and the mixture was stirred at ambient temperature for 3 hours. To a reaction mixture was added dropwise methanol (30 ml) under ice-cooling and the solution was evaporated in vacuo. The resulting residue was dissolved in methanol (30 ml) and concentrated hydrochloric acid (0.5 ml) and stirred overnight at ambient temperature. The reaction mixture was evaporated in vacuo to give a residue. The residue was dissolved in a mixture of ethyl acetate (60 ml) and tetrahydrofuran (30 ml) and the solution was washed with saturated aqueous sodium hydrogen carbonate and saturated aqueous sodium chloride successively, dried over anhydrous magnesium sulfate and evaporated in vacuo to give a residue. The residue was chromatographed on silica gel (100 g) eluting with a mixture of chloroform and methanol (19:1 V/V). The fractions containing the desired compound were collected and evaporated in vacuo to give (2S,4R)-4-methanesulfonyloxy-1-(4-nitrobenzyloxycarbonyl)-2-(2-oxoimidazolidin-1-yl)methylpyrrolidine (0.81 g).

NMR (CDCl$_3$, δ): 2.16–2.47 (2H, m), 3.00 (3H, s), 3.10–3.73 (6H, m), 3.80–4.40 (2H, m), 4.67–4.90 (1H, m), 5.10–5.30 (3H, broad s), 7.48 (2H, d, J=8 Hz), 8.18 (2H, d, J=8 Hz)

PREPARATION 20

To a solution of (2S,4R)-4-methanesulfonyloxy-1-(4-nitrobenzyloxycarbonyl)-2-(2-oxoimidazolidin-1-yl)methylpyrrolidine (0.80 g) in N,N-dimethylformamide (10 ml) was added sodium hydroxide (78 mg) under ice-cooling and the mixture was stirred at the same temperature for 20 minutes. To a solution was added iodomethane (0.34 ml) and the mixture was stirred at 30° C.-50° C. for 1 hour. The reaction mixture was poured into ice-water (30 ml) and extracted twice with ethyl acetate (30 ml). The extract was washed with saturated aqueous sodium chloride, dried over anhydrous magnesium sulfate and evaporated in vacuo. The resulting residue was chromatographed on silica gel (100 g) eluting with a mixture of chloroform and methanol (19:1,V/V). The fractions containing the desired compound were collected and evaporated in vacuo to give (2S,4R)-4-methanesulfonyloxy-2-(3-methyl-2-oxoimidazolidin-1-yl)methyl-1-(4-nitrobenzyloxycarbonyl)pyrrolidine (0.78 g).

NMR (CDCl$_3$, δ): 2.18–2.48 (2H, m), 2.74 (3H, s), 2.98 (3H, s), 5.27 (2H, s), 7.48 (2H, d, J=8 Hz), 8.18 (2H, d, J=8 Hz)

PREPARATION 21

(2S,4R)-4-Methanesulfonyloxy-2-(3-methyl-2-oxoimidazolidin-1-yl)carbonyl-1-(4-nitrobenzyloxycarbonyl)pyrrolidine (0.71 g) was obtained by reacting (2S,4R)-4-methanesulfonyloxy-1-(4-nitrobenzyloxycarbonyl)-2-(2-oxoimidazolidin-1-yl)carbonylpyrrolidine (1.96 g) with sodium hydride (62% in oil suspension) (0.18 g) and iodomethane (0.40 ml) in substantially the same manner as that of Preparation 20.

PREPARATION 22

To a solution of (2S,4R)-4-methanesulfonyloxy-2-(3-methyl-2-oxoimidazolidin-1-yl)carbonyl-1-(4-nitrobenzyloxycarbonyl)pyrrolidine (0.70 g) in tetrahydrofuran (3.5 ml) was added 1.0M solution of borane-tetrahydrofuran complex in tetrahydrofuran (20.9 ml) and the mixture was stirred at ambient temperature for 1 hour and at 35°–40° C. for 2.5 hours. Methanol (20 ml) was added dropwise to the reaction mixture on ice-bath and the mixture was evaporated in vacuo. The resulting residue was dissolved in a mixture of methanol (20 ml) and 1.7M solution of hydrogen chloride in methanol (1 ml) and the mixture was allowed to stand overnight. The reaction mixture was evaporated in vacuo to give a residue. The residue was dissolved in ethyl acetate (60 ml) and the solution was washed with saturated aqueous sodium hydrogen carbonate and aqueous sodium chloride, dried over anhydrous magnesium sulfate and evaporated in vacuo. The resulting residue was chromatographed on silica gel (30 g) eluting with a mixture of chloroform and methanol (9:1, V/V). The fractions containing the desired compound were collected and evaporated in vacuo to give (2S,4R)-4-methanesulfonyloxy-2-(3-methyl-2-oxoimidazolidin-1-yl)methyl-1-(4-nitrobenzyloxycarbonyl)pyrrolidine (0.33 g).

PREPARATION 23

To a solution of sodium hydride (0.35 g) in N,N-dimethylformamide (30 ml) was added dropwise thioacetic S-acid (0.74 ml) with stirring under ice-cooling. The mixture was stirred at the same temperature for 30 minutes. A solution of (2S,4R)-4-methanesulfonyloxy-2-(3-methyl-2-oxoimidazolidin-1-yl)methyl-1-(4-nitrobenzyloxycarbonyl)pyrrolidine (3.17 g) in N,N-dimethylformamide (7 ml) was added to the mixture obtained above with stirring at the same temperature. The mixture was stirred at 80°–90° C. for 2 hours. The reaction mixture was poured into ice-water (100 ml) and extracted twice with ethyl acetate (100 ml). The extract was washed with saturated aqueous sodium chloride, dried over anhydrous magnesium sulfate and evaporated in vacuo. The resulting residue was chromatographed on silica gel (100 g) eluting with a mixture of chloroform and methanol (19:1, V/V). The fractions containing the desired compound were collected and evaporated in vacuo to give (2S,4S)-4-acetylthio-2-(3-methyl-2-oxoimidazolidin-1-yl)methyl-1(4-nitrobenzyloxycarbonyl)pyrrolidine (1.74 g).

IR (Neat): 1710–1670, 1610, 1520 cm$^{-1}$

NMR (CDCl$_3$, $\delta$): 2.28 (3H, s), 2.77 (3H, s), 5.18 (2H, s), 7.46 (2H, d, J=8 Hz), 8.16 (2H, d, J=8 Hz)

PREPARATION 24

To a solution of (2S,4S)-4-acetylthio-2-(3-methyl-2-oxoimidazolidin-1-yl)methyl-1-(4-nitrobenzyloxycarbonyl)pyrrolidine (1.72 g) in methanol (40 ml) was added 28% sodium methoxide in methanol solution (0.83 ml) and the mixture was stirred under ice-cooling for 30 minutes. Acetic acid (0.25 ml) was added to the reaction mixture at the same temperature. The mixture was evaporated in vacuo to give a residue. The residue was dissolved in a mixture of ethyl acetate (80 ml) and tetrahydrofuran (30 ml) and the solution was washed with saturated aqueous sodium chloride, dried over anhydrous magnesium sulfate and evaporated in vacuo. The resulting residue was chromatographed on silica gel (100 g) eluting with a mixture of chloroform and methanol (19:1, V/V). The fractions containing the desired compound were collected and evaporated in vacuo to give (2S,4S)-4-mercapto-2-(3-methyl-2-oxoimidazolidin-1-yl)methyl-1-(4-nitrobenzyloxycarbonyl)pyrrolidine (1.23 g).

IR (Neat): 1710–1670, 1605, 1525–1495 cm$^{-1}$

NMR (CDCl$_3$, $\delta$): 1.64–1.97 (2H, m), 2.28–2.68 (1, m), 1.74 (3H, s), 3.03–3.70 (8H, m), 3.80–4.25 (2H, m), 5.16 (2H, s), 7.49 (2H, d, J=9 Hz), 8.17 (2H, d, J=9 Hz)

PREPARATION 25

To a solution of (2S,4S)-2-(methanesulfonyloxy)methyl-1-(4-nitrobenzyloxycarbonyl)-4-(triphenylmethylthio)pyrrolidine (8.76 g) in dimethylformamide (80 ml) were added (2S)-2-(hydroxymethyl)pyrrolidine (8.72 g) and triethylamine (3.86 ml) and the mixture was stirred at 100° C. for 5 hours. The reaction mixture was poured into ice-water (300 ml) and extracted twice with ethyl acetate (200 ml). The extract was washed with saturated aqueous sodium chloride, dried over magnesium sulfate and evaporated in vacuo. The resulting residue was chromatographed on silica gel (150 g) eluting with a mixture of dichloromethane and acetone (2:1, V/V). The fractions containing the desired compound were collected and evaporated in vacuo to give (2S,4S)-2-[(2S)-2-(hydroxymethyl)pyrrolidin-1-yl]methyl-1-(4-nitrobenzyloxycarbonyl)-4-(triphenylmethylthio)pyrrolidine (5.75 g).

NMR (DCl$_3$, $\delta$): 5.00–5.28 (2H, m), 7.05–7.65 (17H, m), 8.22 (2H, d, J=8 Hz)

PREPARATION 26

To a solution of (2S,4S)-2-(methanesulfonyloxy)methyl-1-(4-nitrobenzyloxycarbonyl)-4-(triphenylmethylthio)pyrrolidine (7.1 g) in dimethylformamide (70 ml) was added sodium azide (1.09 g) and ammonium chloride (0.90 g) and the mixture was stirred at 80°–90° C. for 3 hours. The reaction mixture was poured into ice-water (200 ml) and extracted twice with ethyl acetate (200 ml). The extract was washed with saturated aqueous sodium chloride, dried over magnesium sulfate and evaporated in vacuo. The resulting residue was chromatographed on silica gel (200 g) eluting with n-hexane and ethyl acetate (2:1, V/V). The fractions containing the desired compound were collected and evaporated in vacuo to give (2S,4S)-2-azidomethyl-1-(4-nitrobenzyloxycarbonyl)-4-(triphenylmethylthio)pyrrolidine (5.20 g).

IR (Neat): 2120, 1710–1700, 1610, 1525 cm$^{-1}$

NMR (CDCl$_3$, $\delta$): 3.58–3.93 (2H, m), 5.12 (2H, s), 7.06–7.60 (17H, m), 8.25 (2H, d, J=8 Hz)

PREPARATION 27

A solution of (2S,4S)-2-azidomethyl-1-(4-nitrobenzyloxycarbonyl)-4-(triphenylmethylthio)pyrrolidine (5.18 g) and triphenylphosphine (3.75 g) in pyridine (15 ml) was stirred at ambient temperature for 1 hour. To a reaction mixture was added concentrated ammonia water (1.2 ml) with stirring at ambient temperature and the mixture was allowed to stand overnight at the same temperature. The solution was evaporated in vacuo to give a residue. The residue was chromatographed on silica gel (100 g) eluting with a mixture of chloroform and methanol (9:1, V/V). The fractions containing the desired compound were collected and evaporated in vacuo to give (2S,4S)-2-aminomethyl-1-(4-nitrobenzyloxycarbonyl)-4-(triphenyl15, methylthio)pyrrolidine (6.13 g).

NMR (CDCl$_3$, $\delta$): 3.50–3.83 (1, m), 5.12 (2H, s), 8.25 (2H, d, J=8 Hz)

PREPARATION 28

To a solution of (2S,4S)-2-aminomethyl-1-(4-nitrobenzyloxycarbonyl)-4-(triphenylmethylthio)pyrrolidine (7.78 g) in a mixture of tetrahydrofuran (120 ml) and water (40 ml) was added dropwise chloroacetyl chloride (1.23 ml) with stirring under ice-cooling, keeping the pH 8–10 with triethylamine. The mixture was stirred at the same temperature for 1 hour. The reaction mixture was evaporated in vacuo to remove the organic layer. The resulting residue was extracted twice with ethyl acetate (100 ml). The extract was washed with saturated aqueous sodium chloride, dried over anhydrous magnesium sulfate and evaporated in vacuo to give (2S,4S)-2-(chloroacetylamino)methyl-1-(4- nitrobenzyloxy-carbonyl)-4-(triphenylmethylthio)pyrrolidine (7.35 g).

PREPARATION 29

A solution of (2S,4S)-2-(chloroacetylamino)methyl-1-(4-nitrobenzyloxycarbonyl)-4-(triphenylmethylthio)-pyrrolidine (1.0 g), potassium cyanate (1.3 g) and tetra-n-butylammonium iodide (0.2 g) in acetonitrile (50 ml) was stirred at 60°–80° C. for 8 hours To a reaction mixture was added ethyl acetate (150 ml) and the organic layer was separated, washed with saturated aqueous sodium chloride, dried over anhydrous magnesium sulfate, and evaporated in vacuo. The resulting residue was chromatographed on silica gel (50 g) eluting with a mixture of chloroform and acetone (9:1, V/V). The fractions containing the desired compound were collected and evaporated in vacuo to give (2S,4S)-2-(2,5-dioxoimidazolidin-1-yl)methyl-1-(4-nitrobenzyloxycarbonyl)-4-(triphenylmethylthio)pyrrolidine (0.82 g).

IR (Nujol): 1775, 1710–1700, 1600, 1520 cm$^{-1}$
NMR (CDCl$_3$, δ): 1.25–1.77 (1H, m), 1.90–2.40 (1H, m), 2.50–3.25 (3H, m), 3.35–3.93 (4H, m), 3.94–4.33 (1H, m), 5.06 (2H, broad s), 5.43–5.80 (1H, m), 7.00–7.68 (17H, m), 8.18 (2H, d, J=8 Hz)

PREPARATION 30-(1)

To a solution of (2S,4S)-2-[(2S)-2-(hydroxymethyl)-pyrrolidin-1-yl]methyl-1-(4-nitrobenzyloxycarbonyl)-4-(triphenylmethylthio)pyrrolidine (5.74 g) in trifluoroacetic acid (30 ml) was added 2-mercaptoethanol (0.95 ml) under ice-cooling and the mixture was stirred at ambient temperature for 15 minutes. The reaction mixture was evaporated in vacuo. The resulting residue was dissolved in toluene (30 ml) and the solution was evaporated in vacuo to give a residue. The residue was dissolved in ethyl acetate (100 ml) and the solution was washed in turn with saturated aqueous sodium hydrogen carbonate and aqueous sodium chloride, dried over magnesium sulfate and evaporated in vacuo. The resulting residue was chromatographed on silica gel (100 g) eluting with a mixture of chloroform and methanol (9:1,V/V). The fractions containing the desired compound were collected and evaporated in vacuo to give (2S,4S)-2-[(2S)-2-(hydroxymethyl)pyrrolidin-1-yl]methyl-4-mercapto-1-(4-nitrobenzyloxycarbonyl)-pyrrolidine (1.77 g).

IR (Nujol): 1710–1660, 1610, 1545 cm$^{-1}$
NMR (CDCl$_3$, δ): 1.68–2.35 (5H, m), 2.58–3.02 (2H, m), 3.27–4.37 (12H, m), 5.26 (2H, s), 7.55 (2H, d, J=9 Hz), 8.27 (4H, d, J=9 Hz)

PREPARATION 30-(2)

(2S,4S)-2-(2,5-Dioxoimidazolidin-1-yl)methyl-4-mercapto-1-(4-nitrobenzyloxycarbonyl)pyrrolidine was obtained in 13.6% yield in substantially the same manner as that of Preparation 30-(1).

IR (Neat): 1760, 1710–1685, 1605, 1525 cm$^{-1}$
NMR (CDCl$_3$, δ): 3.05–3.46 (2H, m), 5.10–5.38 (2H, m), 5.70–6.00 (1H, m), 7.40–7.70 (2H, m), 8.20 (2H, d, J=9 Hz)
FB Mass: 395 (M$^+$+1)

PREPARATION 31-(1)

(2S,4S)-2-(3-Oxopiperazin-1-yl)methyl-1-(4-nitrobenzyloxycarbonyl)-4-(triphenylmethylthio)pyrrolidine (3.50 g) was obtained by reacting (2S,4S)-2-(methanesulfonyloxy)methyl-1-(4-nitrobenzyloxycarbonyl)-4-(triphenylmethylthio)pyrrolidine (5.5 g) with 2-oxopiperazine (1.76 g) in substantially the same manner as that of Preparation 3-(1).

IR (Neat): 1700, 1605, 1525, 1265 cm$^{-1}$
NMR (CDCl$_3$, δ): 5.07–5.33 (2H, m), 7.10–7.68 (17H, m), 8.28 (2H, d, J=8 Hz)

PREPARATION 31-(2)

(2S,4S)-2-(Morpholinomethyl)-1-(4-nitrobenzyloxycarbonyl)-4-(triphenylmethylthio)pyrrolidine (2.49 g) was obtained by reacting (2S,4S)-2-(methanesulfonyloxy)methyl-1-(4-nitrobenzyloxycarbonyl)-4-(triphenylmethylthio)pyrrolidine (5.0 g) with morpholine (2.07 ml) in substantially the same manner as that of Preparation 3-(1).

PREPARATION 32

A mixture of (2S,4S)-2-(methanesulfonyloxy)methyl-1-(4-nitrobenzyloxycarbonyl)-4-(triphenylmethylthio)-pyrrolidine (2.28 g) and piperazine (0.93 g) in dimethylformamide (40 ml) was stirred at 80°–90° C. for 5 hours. The reaction mixture was poured into ice-water (150 ml). The precipitates were collected by filtration, washed with water and dissolved in ethyl acetate (100 ml). The solution was washed twice with saturated aqueous sodium chloride (30 ml), dried over anhydrous magnesium sulfate and evaporated in vacuo to give a residue. The residue was dissolved in a mixture of tetrahydrofuran (20 ml) and water (10 ml). To the solution were added concentrated hydrochloric acid (0.60 ml) and potassium cyanate (0.44 g) and the mixture was stirred at 50° C. for 30 minutes. Ethyl acetate was added to the reaction mixture with stirring. The organic layer was separated and washed twice with saturated aqueous sodium chloride, dried over anhydrous magnesium sulfate, and evaporated in vacuo. The resulting residue was chromatographed on silica gel (100 g) eluting with a mixture of dichloromethane and acetone (2:1, V/V and then 1:2, V/V). The fractions containing the desired compound were collected and evaporated in vacuo to give (2S,4S)-2-(4-carbamoylpiperazin-1-yl)methyl-1-(4-nitrobenzyloxycarbonyl)-4(triphenylmethylthio)pyrrolidine (1.30 g).

IR (Nujol) 1710–1700, 1690, 1670–1650, 1590, 1520 cm$^{-1}$
NMR (CDCl$_3$, δ): 4.40–4.58 (2H, m), 5.11 (2H, s), 7.15–7.65 (17H, m), 8.25 (2H, d, J=8Hz)

PREPARATION 33-(1)

(2S,4S)-2-(3-Oxopiperazin-1-yl)methyl-4-mercapto-1-(4-nitrobenzyloxycarbonyl)pyrrolidine was obtained in 27.4% yield in substantially the same manner as that of Preparation 30-(1).

PREPARATION 33-(2)

(2S,4S)-4-Mercapto-2-(morpholinomethyl)-1-(4-nitrobenzyloxycarbonyl)pyrrolidine was obtained in 66.4% yield in substantially the same manner as that of Preparation 30-1).
mp: 93°–94° C.
NMR (CDCl$_3$, δ): 1.66–2.05 (2H, m), 2.30–2.85 (6H, m), 3.00–3.50 (2H, m), 3.55–3.75 (4H, m), 3.83–4.26 (2H, m), 5.19 (2H, s), 7.52 (2H, d, J=8 Hz), 8.25 (2H, d, J=8 Hz)
EI Mass: 381 (M$^+$)

PREPARATION 33-(3)

(2S,4S)-2-(4-Carbamoylpiperazin-1-yl)methyl-4-mercapto-1-(4-nitrobenzyloxycarbonyl)pyrrolidine was obtained in 42.9% yield in substantially the same manner as that of Preparation 30-(1).

NMR (CDCl₃, δ): 1.66–2.13 (2H, m), 2.33–2.86 (7H, m), 3.05–3.55 (6H, m), 3.80–4.28 (2H, m), 4.55 (2H, broad s), 5.22 (2H, s), 7.53 (2H, d, J=8 Hz), 8.25 (2H, d, J=8 Hz)

PREPARATION 34

A mixture of 2-(2-aminoethylamino)ethanol (25 g) and dimethyl carbonate (75 ml) was refluxed for 4 hours. The reaction mixture was evaporated in vacuo to give a residue. The residue was chromatographed on silica gel (500 g) eluting with a mixture of chloroform, methanol and concentrated ammonia water (4:1:0.1, V/V). The fractions containing the desired compound were collected and evaporated in vacuo to give a residue (24.03 g). To the residue was added 1,8-diazabicyclo[5.4.0]undec-7-ene (2.23 ml) and the mixture was stirred at 150° C. for 3 hours. The reaction mixture was cooled and chromatographed on silica gel (200 g) eluting with a mixture of chloroform, methanol and conc. ammonia water (9:1:0.1, V/V). The fractions containing the desired compound were collected and evaporated in vacuo to give 3-(2-hydroxyethyl)-2-oxoimidazolidine (13.53 g).

NMR (CDCl₃, δ): 3.20–4.00 (9H, m), 5.23–5.52 (1H, m)

PREPARATION 35

To a mixture of N,N-dimethylformamide (0.6 ml) and tetrahydrofuran (1.2 ml) was added dropwise phosphorus oxychloride (0.58 ml) at −5° C. and the mixture was stirred at 5° C. for 5 minutes. To the mixture was added a solution of (2S,4R)-4-methanesulfonyloxy-1-(4-nitrobenzyloxycarbonyl)proline (2.0 g) in tetrahydrofuran (20 ml) under ice-cooling. The solution was stirred at the same temperature for 30 minutes. To this solution were added 3-(2-hydroxyethyl)-2-oxoimidazolidine (1.0 g) and conc. sulfuric acid (0.035 ml) and the mixture was stirred at 45°–50° C. for 2 hours. Ethyl acetate (50 ml) and water (30 ml) was added to the reaction mixture. The organic layer was washed with saturated aqueous sodium chloride, dried over anhydrous magnesium sulfate and evaporated in vacuo to give a residue. The residue was chromatographed on silica gel (50 g) eluting with a mixture of chloroform and methanol (19:1, V/V). The fractions containing the desired compound were collected and evaporated in vacuo to give (2S,4R)-2-[3-(2-hydroxyethyl)-2-oxoimidazolidin-1-yl]carbonyl-4-methanesulfonyloxy-1-(4-nitrobenzyloxycarbonyl)pyrrolidine (0.19 g).

IR (Neat): 1725–1670, 1605, 1530–1510 cm⁻¹

NMR (CDCl₃, δ): 1.50–1.90 (1H, m), 2.07–2.43 (2H,m), 2.61–3.00 (1H, m), 3.05 (3H, s), 3.30–4.03 (10H, m), 5.07–5.47 (2H, m), 5.60–5.95 (1H, m), 7.52 (1H, d, J=8 Hz), 8.18 (2H, d, J=8 Hz)

FB Mass: 501 (M+)

PREPARATION 36

To a suspension of sodium borohydride (0.71 g) in tetrahydrofuran (25 ml) was added dropwise boron trifluoride etherate (11.8 ml) under ice-cooling and stirred at the same temperature for 10 minutes. To the mixture was added a solution of (2S,4R)-2-[3-(2-hydroxyethyl)-2-oxoimidazolidin-1-yl]carbonyl-4-methanesulfonyloxy1-(4-nitrobenzyloxycarbonyl)pyrrolidine (4.73 g) in tetrahydrofuran (50 ml) and the mixture was stirred at ambient temperature overnight. To the reaction mixture was added dropwise methanol (60 ml) under ice-cooling and evaporated in vacuo. The resulting residue was dissolved in methanol (30 ml) and conc. hydrochloric acid (1 ml) and stirred at ambient temperature for 3 hours. The reaction mixture was evaporated in vacuo to give a residue. The residue was dissolved in ethyl acetate (100 ml) and the solution was washed with saturated aqueous sodium hydrogen carbonate and aqueous sodium chloride successively, dried over anhydrous magnesium sulfate and evaporated in vacuo. The resulting residue was chromatographed on silica gel (100 g) eluting with a mixture of chloroform and methanol (19:1, V/V). The fractions containing the desired compound were collected and evaporated in vacuo to give (2S,4R)-2-[3-(2-hydroxyethyl)-2-oxoimidazolidin-1-yl]methyl-4-methanesulfonyloxy-1-(4-nitrobenzyloxycarbonyl)pyrrolidine (2.70 g).

NMR (CDCl₃, δ): 2.06–2.50 (2H, m), 3.02 (3H, s), 3.10–4.46 (13H, m), 5.03–5.35 (3H, br s), 7.50 (2H, d, J=8 Hz), 8.12 (2H, d, J=8 Hz)

PREPARATION 37

To a solution of (2S,4R)-2-aminomethyl-4-(t-butyldimethylsilyloxy)-1-(4-nitrobenzyloxycarbonyl)pyrrolidine (15 g) in a mixture of tetrahydrofuran (100 ml) and water (50 ml) was added dropwise 2-chloropropionylchloride (4.27 ml) with stirring under ice-cooling, keeping the pH 9–10 with 4N sodium hydroxide. The mixture was stirred at the same temperature for 1 hour. The reaction mixture was evaporated in vacuo to remove the organic layer. The resulting residue was extracted twice with ethyl acetate (100 ml). The extract was washed with saturated aqueous sodium chloride, dried over anhydrous magnesium sulfate and evaporated in vacuo to give (2S,4R)-4-(t-butyldimethylsilyloxy)-2-(2-chloropropionyl)aminomethyl-1-(4-nitrobenzyloxycarbonyl)pyrrolidine (18.36 g).

PREPARATION 38

A solution of (2S,4R)-4-(t-butyldimethylsilyloxy)-2-(2-chloropropionyl)aminomethyl-1-(4-nitrobenzyloxycarbonyl)pyrrolidine (18.4 g), potassium cyanate (14.9 g) and tetrabutylammonium iodide (13.6 g) in N,N-dimethylformamide (180 ml) was stirred at 100°–110° C. for 3 hours. The reaction mixture was poured into water (300 ml) and extracted twice with ethyl acetate (200 ml). The extract was washed with saturated aqueous sodium chloride, dried over anhydrous magnesium sulfate and evaporated in vacuo. The resulting residue was dissolved in a mixture of methanol (150 ml) and concentrated hydrochloric acid (6.1 ml). The solution was stirred at ambient temperature for 2 hours and evaporated in vacuo. The resulting residue was chromatographed on silica gel (250 g) eluting with a mixture of chloroform and methanol (19:1, V/V). The fractions containing the desired compound were collected and evaporated in vacuo to give (2S,4R)-4-hydroxy-2-(4-methyl-2,5-dioxoimidazolidin-1-yl)methyl-1-(4-nitrobenzyloxycarbonyl)pyrrolidine (8.16 g).

NMR (CDCl₃, δ): 1.36 (3H, d, J=7 Hz), 1.73–2.30 (3H, m), 2.53–2.88 (1H, m), 3.30–4.20 (5H, m), 4.22–4.68 (2H, m), 5.06–5.45 (2H, m), 5.98–6.35 (1, m), 7.46 (1H, d, J=8 Hz), 7.59 (1H, d, J=8 Hz), 8.19 (4H, d, J=8 Hz)

PREPARATION 39

To a suspension of sodium borohydride (1.81 g) in tetrahydrofuran (50 ml) was dropwise added boron trifluoride etherate (23.4 ml) under ice-cooling and the mixture was stirred at the same temperature for 15 minutes. To this solution was added a solution of (2S,4R)-4-hydroxy-2-(4-methyl-2,5-dioxoimidazolidin-1-yl)methyl-1-(4-nitrobenzyloxycarbonyl)pyrrolidine (9.37 g) in tetrahydrofuran (50 ml) under ice-cooling and the mixture was stirred at ambient temperature overnight. To the reaction mixture was dropwise added methanol (30 ml) and the mixture was filtered. The filtrate was evaporated in vacuo. The resulting residue was dissolved in methanol (100 ml) and concentrated hydrochloric acid (5 ml) and the solution was allowed to stand at ambient temperature for 3 hours. The reaction mixture was evaporated in vacuo and dissolved in ethyl acetate (300 ml). The solution was washed successively with saturated aqueous sodium hydrogen carbonate and aqueous sodium chloride, dried over magnesium sulfate and evaporated in vacuo. The resulting residue was chromatographed on silica gel (150 g) eluting with a mixture of chloroform and methanol (19:1, V/V). The fractions containing the desired compound were collected and evaporated in vacuo to give (2S,4R)-4-hydroxy-2-(4-methyl-2-oxoimidazolidin-1-yl)methyl-1-(4-nitrobenzyloxycarbonyl)pyrrolidine (4.31 g).

IR (Neat): 1705 (sh), 1690, 1605, 1525, 1495 cm$^{-1}$

NMR (CDCl$_3$, δ): 1.19 (3H, d, J=6 Hz), 1.90–2.20 (2H, m), 2.70–3.10 (1, m), 3.13–3.90 (7H, m), 4.00–4.30 (1H, m), 4.33–4.60 (1H, m), 4 73–8.00 (1H, m), 5.20 (2H, s), 7.50 (2H, d, J=8 Hz), 8.28 (2H, d, J=8 Hz)

PREPARATION 40

To a solution of (2S,4R)-4-hydroxy-2-(4-methyl-2-oxoimidazolidin-1-yl)methyl-1-(4-nitrobenzyloxycarbonyl)pyrrolidine (4.30 g) in dichloromethane (50 ml) were added successively pyridine (1.1 ml), 4-(N,N-dimethylamino)pyridine (1.39 g) and methanesulfonyl chloride (0.97 ml) under ice-cooling and the mixture was stirred at ambient temperature for 3 hours. The reaction mixture was washed successively with 1N hydrochloric acid, aqueous sodium hydrogen carbonate and sodium chloride, dried over magnesium sulfate and evaporated in vacuo. The resulting residue was chromatographed on silica gel (100 g) eluting with a mixture of chloroform and methanol (19:1, V/V). The fractions containing the desired compound were collected and evaporated in vacuo to give (2S,4R)-4-methanesulfonyloxy-2-(4-methyl-2-oxoimidazolidin-1-yl)methyl-1-(4-nitrobenzyloxycarbonyl)pyrrolidine (4.76 g).

IR (Neat): 1710–1680, 1610, 1525, 1495, 1270, 1175 cm$^{-1}$

NMR (CDCl$_3$, δ): 1.19 (3H, d, J=6 Hz), 2.20–2.46 (2H, m), 2.70–3.00 (1H, m), 3.03 (3H, s), 3 15–4.43 (7H, m), 5.06–5.50 (4H, br.s), 7.51 (2H, d, J=8 Hz), 8.17 (2H, d, J=8 Hz)

PREPARATION 41-(1)

(2S,4S)-4-Acetylthio-2-[3-(2-hydroxyethyl)-2-oxoimidazolidin-1-yl]methyl-1-(4-nitrobenzyloxycarbonyl)pyrrolidine was obtained in 71.0% yield in substantially the same manner as that of Preparation 23.

NMR (CDCl$_3$, δ): 1.55–2.18 (2H, m), 2.32 (3H, s), 2.32–4.30 (15H, m), 5.20 (2H, s), 7.50 (2H, d, J=8 Hz), 8.18 (2H, d, J=8 Hz)

PREPARATION 41-(2)

(2S,4S)-4-Acetylthio-2-(4-methyl-2-oxoimidazolidin-1-yl)methyl-1-(4-nitrobenzyloxycarbonyl)pyrrolidine was obtained in 81.0% yield in substantially the same manner as that of Preparation 23.

NMR (CDCl$_3$, δ): 1.17 (3H, d, J=6 Hz), 1.65–2.10 (2H, m), 2.30–2.66 (1H, m), 2.90–4.26 (8H, m), 4.58 (1H, br s), 5.18 (2H, s), 7.48 (2H, d, J=8 Hz), 8.18 (2H, d, J=8 Hz)

PREPARATION 42-(1)

(2S,4S)-2-[3-(2-Hydroxyethyl)-2-oxoimidazolidin-1-yl]methyl-4-mercapto-1-(4-nitrobenzyloxycarbonyl)pyrrolidine was obtained in 89.1% yield in substantially the same manner as that of Preparation 24.

1710–1650, 1605 cm$^{-1}$

NMR (CDCl$_3$, δ): 1.60–2.16 (3H, m), 2.26–2.76 (1, m), 2.95–3.62 (8H, m), 3.72 (2H, t, J=5 Hz), 3.88–4.25 (2H, m), 5.18 (2H, s), 7.49 (2H, d, J=8 Hz), 8.18 (2H, d, J=8 Hz)

EI Mass: 425 (M$^+$+1), 424 (M$^{30}$)

PREPARATION 42-(2)

(2S,4S)-4-Mercapto-2-(4-methyl-2-oxoimidazolidin-1-yl)methyl-1-(4-nitrobenzyloxycarbonyl)pyrrolidine was obtained in 92.8% yield in substantially the same manner as that of Preparation 24.

IR (Neat): 1710, 1690, 1605, 1520, 1490, 1345, 1270 cm$^{-1}$

NMR (CDCl$_3$, δ): 1.20 (3H, d, J=6 Hz), 1.66–2.13 (2H, m), 2.31–2.72 (1H, m), 2.76–4.30 (9H, m), 5.20 (3H, br s), 7.50 (2H, d, J=8 Hz), 8.18 (2H, d, J=8 Hz)

EI Mass. 394 (M$^+$), 361 (M$^+\neq^{-33}$)

PREPARATION 43

To a solution of (2S,4R)-4-methanesulfonyloxy-1-(4-nitrobenzylocycarbonyl)-2-(2-oxoimidazolidin-1-yl)methylpyrrolidine (5.60 g) and 4-(N,N-dimethylamino)-pyridine (1.36 g) in dichloromethane (60 ml) was dropwise added acetyl chloride (1.48 ml) under ice-cooling and the mixture was stirred at the same temperature overnight. The reaction mixture was washed successively with 1N hydrochloric acid, aqueous sodium hydrogen carbonate and aqueous sodium chloride, dried over magnesium sulfate and evaporated in vacuo. The resulting residue was chromatographed on silica gel (100 g) eluting with a mixture of chloroform and methanol (19:1, V/V). The fractions containing the desired compound were collected and evaporated in vacuo to give (2S,4R)-2-(3-acetyl-2-oxoimidazolidin-1-yl)methyl-4-methanesulfonyloxy-1-(4-nitrobenzyloxycarbonyl)pyrrolidine (1.13 g).

NMR (CDCl$_3$, δ): 1.66–1.95 (1, m), 2.13 (3H, s), 2.13–2.65 (2H, m), 3.00 (3H, s), 3.20–4.46 (9H, m), 5.20 (2H, s), 7.46 (2H, d, J=8 Hz), 8.16 (2H, d, J=8 Hz)

PREPARATION 44

To a suspension of sodium borohydride (0.16 g) in tetrahydrofuran (11 ml) was dropwise added boron trifluoride etherate (2.83 ml) under ice-cooling and the mixture was stirred at the same temperature for 15 minutes. To this solution was added a solution of (2S,4R)-2-(3-acetyl-2-oxoimidazolidin-1-yl)methyl-4-methanesulfonyloxy-1-(4-nitrobenzyloxycarbonyl)pyrrolidine (1.12 g) in tetrahydrofuran (2.83 ml) under ice-cooling and the mixture was stirred at ambient temperature overnight. To the reaction mixture was added dropwise methanol (30 ml) and the mixture was filtered. The filtrate was evaporated in vacuo. The resulting residue was dissolved in methanol (30 ml) and conc. hydrochloric acid (0.5 ml) and the solution was allowed to stand at ambient temperature overnight. The reaction mixture was evaporated in vacuo and dissolved in ethyl acetate (50 ml). The solution was washed successively with saturated aqueous sodium hydrogen carbonate and aqueous sodium chloride, dried over magnesium sulfate and evaporated in vacuo. The resulting residue was chromatographed on silica gel (100 g) eluting with a mixture of chloroform and methanol (19:1, V/V). The fractions containing the desired compound were collected and evaporated in vacuo to give (2S,4R)-2-(3-ethyl-2-oxoimidazolidin-1-yl)methyl-4-methanesulfonyloxy-1-(4-nitrobenzyloxycarbonyl)pyrrolidine (1.04 g).

NMR (CDCl$_3$, δ): 1.06 (3H, t, J=6 Hz), 2.20–2.55 (2H, m), 2.99 (3H, s), 3.05–4.40 (1H, m), 5.05–5.40 (3H, m), 7.48 (2H, d, J=8 Hz), 8.18 (2H, d, J=8 Hz)

PREPARATION 45

(2S,4S)-4-Acetylthio-2-(3-ethyl-2-oxoimidazolidin-1-yl)methyl-1-(4-nitrobenzyloxycarbonyl)pyrrolidine was obtained in 93.0% yield in substantially the same manner as that of Preparation 23.

NMR (CDCl$_3$, δ): 1.08 (3H, t, J=7 Hz), 1.76–2.19 (2H, m), 2.30 (3H, s), 2.30–2.70 (1H, m), 3.07–3.68 (8H, m), 3.70–4.28 (3H, m), 5.20 (2H, s), 7.50 (2H, d, J=9 Hz), 8.18 (2H, d, J=9 Hz)

PREPARATION 46

(2S,4S)-2-(3-Ethyl-2-oxoimidazolidin-1-yl)methyl-4-mercapto-1-(4-nitrobenzyloxycarbonyl)pyrrolidine was obtained in 85.4% yield in substantially the same manner as that of Preparation 24.

IR (Neat): 1710, 1790, 1610, 1525, 1495 cm$^{-1}$

PREPARATION 47

A mixture of (2S,4R)-4-methanesulfonyloxy-1-(4-nitrobenzyloxycarbonyl)-2-(2-oxoimidazolidin-1-yl)carbonylpyrrolidine (30 g), 10% palladium on carbon (10 g), methanol (300 ml) and tetrahydrofuran (150 ml) was stirred for 5 hours under atmospheric pressure of hydrogen at ambient temperature. After the catalyst was filtered off, the filtrate was evaporated in vacuo to give a residue. The residue was chromatographed on silica gel (250 g) eluting with a mixture of chloroform and methanol (9:1 V/V). The fractions containing the desired compound were collected and evaporated in vacuo to give (2S,4R)-4-methanesulfonyloxy-2-(2-oxoimidazolidin-1-yl)carbonylpyrrolidine (14.92 g).

mp: 115°–118° C.

IR (Nujol): 1740, 1725, 1660, 1380 cm$^{-1}$

NMR (CDCl$_3$, δ): 2.23–2.37 (1, m), 2.47–2.59 (1, m), 2.80 (1H, br s), 3.05 (3H, s), 3.28–3.31 (2H, m), 3.47–3.58 (3H, m), 3.85–4.02 (2H, m), 4.96–5.05 (1H, m), 5.21–5.29 (1H, m), 6.07 (1H, s)

FD Mass: 277 (M+)

PREPARATION 48

To a solution of (2S,4R)-4-methanesulfonyloxy-2-(2-oxoimidazolidin-1-yl)carbonylpyrrolidine (14.9 g) in a mixture of methanol (150 ml) and tetrahydrofuran (150 ml) were added triethylamine (32.5 ml) and methyl iodide (11.4 ml) and the mixture was stirred at 40° C. for 2 hours. The reaction mixture was evaporated in vacuo. The resulting residue was chromatographed on silica gel (600 g) eluting with a mixture of chloroform and methanol (9:1 V/V). The fractions containing the desired compound were collected and evaporated in vacuo to give a residue. The residue was washed with dichloromethane (100 ml). The resulting precipitates were collected and dried in vacuo to give (2S,4R)-4-methanesulfonyloxy-1-methyl-2-(2-oxoimidazolidin-1-yl)carbonylpyrrolidine (2.30 g).

NMR (CDCl$_3$H, δ): 2.09–2.36 (1, m), 2.43 (3H, s), 2.55–2.79 (2H, m), 3.03 (3H, s), 3.49–3.64 (3H, m), 3.93–4.02 (2H, m), 4.60 (1H, t, J=7.5 Hz), 5.18–5.30 (1H, m), 5.65 (1H, br s)

PREPARATION 49

To a solution of sodium borohydride (0.60 g) in tetrahydrofuran (25 ml) was added dropwise boron trifluoride ether complex (5.8 ml) under ice-cooling and the mixture was stirred at the same temperature for 15 minutes. To the mixture was added a solution of (2S,4R)-4-methanesulfonyloxy-1-methyl-2-(2-oxoimidazolidin-1-yl)carbonylpyrrolidine (2.3 g) in tetrahydrofuran (15 ml) and the mixture was stirred at the same temperature for 5 hours. To the reaction mixture was added dropwise methanol (15 ml) under ice-cooling. The mixture was filtered off and the filtrate was evaporated in vacuo. The resulting residue was dissolved in a mixture of methanol (50 ml) and conc. hydrochloric acid (2 ml) and the solution was stirred at ambient temperature overnight. The reaction mixture was evaporated in vacuo to give a residue. The residue was dissolved in ethyl acetate (50 ml) and the solution was washed with saturated aqueous sodium hydrogen carbonate and aqueous sodium chloride successively, dried over anhydrous magnesium sulfate and evaporated in vacuo. The resulting residue was chromatographed on silica gel (100 g) eluting with a mixture of chloroform and methanol (9:1 V/V). The fractions containing the desired compound were collected and evaporated in vacuo to give (2S,4R)-4-methanesulfonyloxy-1-methyl-2-(2-oxoimidazolidin-1-yl)methylpyrrolidine (1.89 g).

NMR (CDCl$_3$, δ): 2.09–2.17 (2H, m), 2.40 (3H, s), 2.48–2.56 (1H, m), 2.62–2.74 (1H, m), 3.00 (3H, s), 2.97–3.08 (1H, m), 3.38–3.70 (6H, m), 4.73 (1H, br s), 5.03–5.15 (1H, m)

PREPARATION 50

A solution of (2S,4R)-4-methanesulfonyloxy-1-methyl-2-(2-oxoimidazolidin-1-yl)methylpyrrolidine (2.50 g) and tetra-n-butylammonium thioacetate (4.16 g) in acetonitrile (70 ml) was stirred at 50°–60° C. for 4 hours. The reaction mixture was evaporated in vacuo to give a residue. The residue was chromatographed on silica gel (200 g) eluting with a mixture of chloroform and methanol (20:1 V/V). The fractions containing the desired compound were collected and evaporated in vacuo to give (2S,4S)-4-acetylthio-1-methyl-2-(2-oxoimidazolidin-1-yl)methylpyrrolidine (1.84 g).

IR (Neat): 1690–1680, 1495, 1270 cm$^{-1}$

NMR (CDCl$_3$, δ): 2.29 (3H, s), 2.35 (3H, s), 3.82–3.91 (1H, m), 4.61 (1H, br s)

PREPARATION 51

To a solution of (2S,4S)-4-acetylthio-1-methyl-2-(2-oxoimidazolidin-1-yl)methylpyrrolidine (1.83 g) in methanol (20 ml) was added 28% sodium methoxide in methanol solution (1.50 ml) at $-10° \sim -5°$ C. and the mixture was stirred at the same temperature for 30 minutes. To the reaction mixture was added acetic acid (0.45 ml) at the same temperature and the mixture was evaporated in vacuo. The resulting residue was chromatographed on silica gel (100 g) eluting with a mixture of chloroform and methanol (9:1 V/V). The fractions containing the desired compound were collected and evaporated in vacuo to give (2S,4S)-4-mercapto-1-methyl-2-(2-oxoimidazolidin-1-yl)methylpyrrolidine (0.60 g).

NMR (CDCl$_3$, δ): 1.67–1.79 (2H, m), 2.38 (3H, s), 2.39–2.58 (3H, m), 2.69 (1H, dd, J=10 Hz, J=7 Hz), 2.97–3.10 (2H, m), 3.20–3.59 (6H, m), 3.66–3.86 (1H, m)

EXAMPLE 1

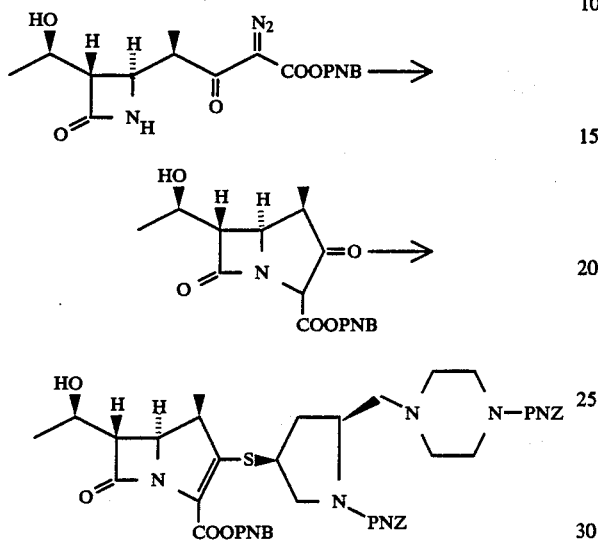

(PNB: 4-nitrobenzyl, PNZ: 4-nitrobenzyloxycarbonyl)

To a solution of 4-nitrobenzyl (4R)-2diazo-4-[(2R,3S)-3-{(1R)-1-hydroxyethyl}-4-oxoazetidin-2-yl]3-oxopentanoate (0.80g) in 1,2-dichloroethane (16 ml) was added rhodium(II) acetate (2 mg) under refluxing. After refluxing for 30 minutes, the reaction mixture was cooled and evaporated in vacuo to give a residue. The residue was dissolved in anhydrous acetonitrile (10 ml) and then evaporated. This operation was repeated once again and the residue was dried in vacuo to give 4-nitrobenzyl (4R,5R,6S)-6-[(1R)-1-hydroxyethyl]-4-methyl-3,7-dioxo-1-azabicyclo[3.2.0]heptane-2-carboxylate. The residue containing the compound obtained above was dissolved in anhydrous acetonitrile (16 ml) and cooled to 0° C. under an atmosphere of nitrogen. To this solution were added diphenyl phosphorochloridate (0.45 ml) and N,N-diisopropyl-N-ethylamine (0.46 ml) successively, and the solution was stirred at 0° C. for 40 minutes To the resulting solution were added dropwise a solution of (2S,4S)-4-mercapto-1-(4-nitrobenzyloxycarbonyl)-2-[4-(4-nitrobenzyloxycarbonyl)piperazin-1-yl]methylpyrrolidine (1.50 g) in acetonitrile (4 ml) and N,N-diisopropyl-N-ethylamine (0.46 ml) with stirring at 5° C., and the stirring was continued at the same temperature for 2 hours. To the reaction mixture was added ethyl acetate (30 ml) and water (10 ml) with stirring, and the organic layer was separated. This layer was washed with saturated aqueous sodium chloride solution (30 ml×3), dried over magnesium sulfate and evaporated. The residue was chromatographed on silica gel (80 g) eluting with a mixture of dichloromethane and acetone (2:1 v/v). The fractions containing the desired compound were collected and evaporated in vacuo to give 4-nitrobenzyl (4R,5S,6S)-6-[(1R)-1-hydroxyethyl]-4-methyl-3-[(2S,4S)-1-(4-nitrobenzyloxycarbonyl)-2-{4-(4-nitrobenzyloxycarbonyl)piperazin-1-yl}methylpyrrolidin-4-yl]thio-7-oxo-1-azabicyclo[3.2.0]hept-2-ene-2-carboxylate (1.20 g).

IR (Nujol): 1765, 1705–1685, 1605, 1520, 1345, 1240 cm$^{-1}$

NMR (CDCl$_3$, δ): 1.26 (3H, d, J=6 Hz), 1.32 (3H, d, J=7 Hz), 5.06–5.62 (6H, m), 7.49 (4H, d, J=8 Hz), 7.63 (2H, d, J=9 Hz), 8.28 (6H, d, J=8 Hz)

EXAMPLE 2

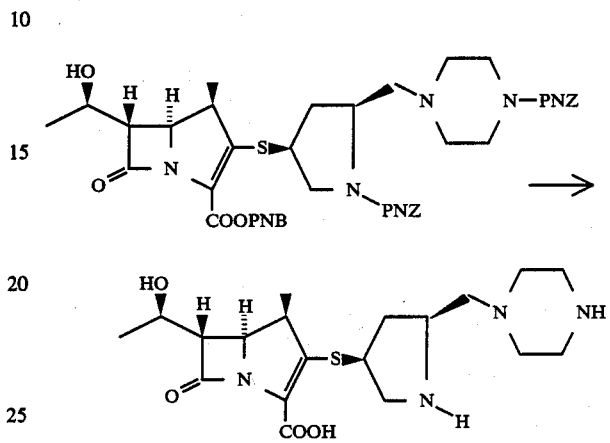

A mixture of 4-nitrobenzyl (4R,5S,6S)-6-[(1R)-1-hydroxyethyl]-4-methyl-3-[(2S,4S)-1-(4-nitrobenzyloxycarbonyl)-2-{4-(4-nitrobenzyloxycarbonyl)piperazin-1-yl}methylpyrrolidin-4-yl]thio-7-oxo-1-azabicyclo[3.2.0]hept-2-ene-2-carboxylate (1.20 g), 20 % palladium hydroxide on carbon (0.6 g), 0.2M sodium acetate-acetic acid buffer (pH=5.8, 50 ml) and tetrahydrofuran (50 ml) was stirred for 5 hours under atmospheric pressure of hydrogen at ambient temperature. After the catalyst was filtered off, the filtrate was evaporated under reduced pressure to remove the organic solvent. The residue was chromatographed on nonionic adsorption resin, "Diaion HP-20" (trademark, made by Mitsubishi Chemical Industries) (30 ml) eluting in turn with water (80 ml) and 5% aqueous acetone (90 ml). The fractions containing the desired compound were collected and lyophilized to give (4R,5S,6S)-6-[(1R)-1-hydroxyethyl]-4-methyl-7-oxo-3-[(2S,4S)-2-(piperazin-1-yl)methylpyrrolidin-4-yl]thio-1-azabicyclo[3.2.0-]hept-2-ene-2-carboxylic acid (0.23 g).

mp: >181° C. (dec.)

IR (Nujol): 1755–1735, 1580–1540 cm$^{-1}$

NMR (D$_2$O, δ): 1.23 (3H, d, J=8 Hz), 1.29 (3H, d, J=6 Hz), 1.50–1.90(2H, m), 2.50–3.06 (6H, m), 3.10–4.40 (12H, m)

SI Mass: 411 (M+)

The following compounds were obtained in substantially the same manner as that of Example 1.

EXAMPLE 3

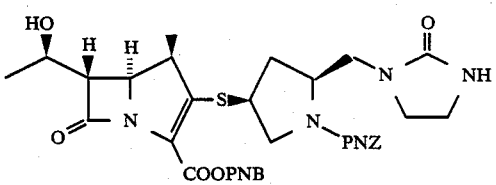

4-Nitrobenzyl (4R,5S,6S)-6-[(1R)-1-hydroxyethyl]-4-methyl-3-[(2S,4S)-1-(4-nitrobenzyloxycarbonyl)-2-(2- oxoimidazolidin-1-yl)methylpyrrolidin 4-yl]thio-7-oxo-1-azabicyclo[3.2.0]hept-2-ene-2-carboxylate IR (Nujol): 1770, 1690, 1605, 1520, 1350, 1275 cm$^{-1}$ NMR (CDCl$_3$, δ): 1.30 (3H, d, J=6 Hz), 1.33 (3H, d, J=6 Hz), 3.06–4.93 (14H, m), 5.12–5.73 (4H, m), 7.60 (2H, d, J=8 Hz), 7.67 (2H, d, J=8 Hz), 8.26 (4H, d, J=8 Hz)

EXAMPLE 4

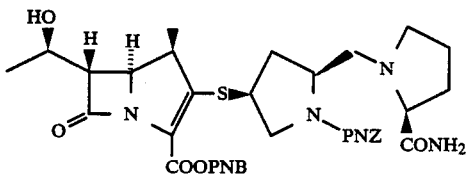

4-Nitrobenzyl (4R,5S,6S)-3-[(2S,4S)-2-{(2S)-2-carbamoylpyrrolidin-1-yl}methyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate IR (Nujol): 1770–1760, 1710–1670, 1520 cm$^{-1}$ NMR (CDCl$_3$, δ): 1.29 (3H, d, J=7 Hz), 1.36 (3H, d, J=6 Hz), 1.70–2.10 (4H, m), 5.10–5.70 (4H, m), 7.60 (2H, d, J=9 Hz), 7.69 (2H, d, J=9 Hz), 8.27 (4H, d, J=9 Hz)

The following compounds were obtained in substantially the same manner as that of Example 2.

EXAMPLE 5

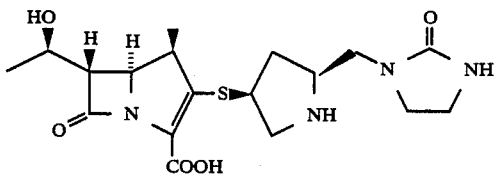

(4R,5S,6S)-6-[(1R)-1-Hydroxyethyl]-4-methyl-7-oxo-3-[(2S,4S)-2-(2-oxoimidazolidin-1-yl)methylpyrrolidin-4-yl]thio-1-azabicyclo[3.2.0]hept-2-ene-2-carboxylic mp: >184° C. (dec.)

IR (Nujol): 1760, 1690–1680, 1590, 1280 cm$^{-1}$

NMR (D$_2$O, δ): 1.21 (3H, d, J=7 Hz), 1.28 (3H, d, J=6 Hz), 1.50–2.15 (2H, m), 2.50–2.93 (1H, m), 3.20–4.35 (13H, m)

SI Mass: 411 (M$^+$+1)

EXAMPLE 6

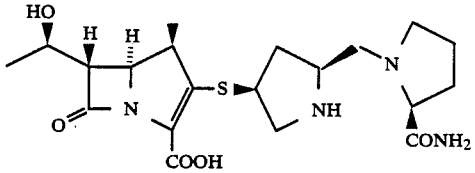

(4S,5S,6S)-3-[(2S,4S)-2-{(2S)-2-Carbamoylpyrrolidin-1-yl}pyrrolidin-4-yl]thio-6-[(1R)-1-hydroxyethyl]-4-methyl-7-oxo-1-azabicyclo[3.2.0]hept-2-ene-2-carboxylic acid IR (Nujol): 1755–1740, 1665–1650, 1590–1580 cm$^{-1}$ NMR (D$_2$O, δ): 1.17 (3H, d, J=7 Hz), 1.25 (3H, d, J=6 Hz), 1.50–2.05 (4H, m), 4.10–4.40 (2H, m)

SI Mass: 439 (M$^+$)

EXAMPLE 7

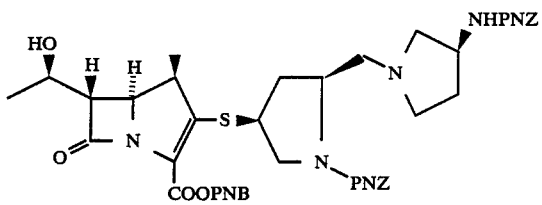

4-Nitrobenzyl (4R,5S,6S)-6-[(1R)-1-hydroxyethyl]-3-[(2S,4S)-1-(4-nitrobenzyloxycarbonyl)-2-{(3S)-3-(4-nitrobenzyloxycarbonylamino)pyrrolidin-1-yl}methylpyrrolidin-4-yl]thio-4-methyl-7-oxo-1-azabicyclo[3.2.0]hept-2-ene-2-carboxylate was obtained in 57.5% yield in substantially the same manner as that of Example 1.

IR (Nujol): 1760, 1710–1700, 1605, 1520, 1345 cm$^{-1}$

NMR (CDCl$_3$, δ): 1.31 (3H, d, J=7 Hz), 1.40 (3H, d, J=7 Hz), 5.05–5.60 (6H, m), 7.58 (4H, d, J=9 Hz), 7.70 (2H, d, J=9 Hz), 8.28 (6H, d, J=9 Hz)

EXAMPLE 8

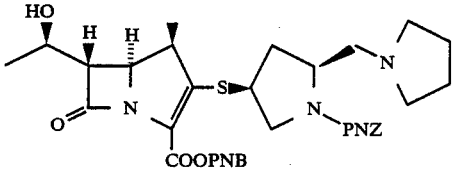

4-Nitrobenzyl (4R,5S,6S)-6-[(1R)-1-hydroxyethyl]-3-[(2S,4S)-1-(4-nitrobenzyloxycarbonyl)-2-(pyrrolidin-1-yl)methylpyrrolidin-4-yl]thio-4-methyl-7-oxo-1-azabicyclo[3.2.0]hept-2-ene-2-carboxylate was obtained in 33.5% yield in substantially the same manner as that of Example 1.

IR (Neat): 1770, 1705, 1610, 1525, 1350 cm$^{-1}$

NMR (CDCl$_3$, δ): 1.26 (3H, d, J=7 Hz), 1.36 (3H, d, J=7 Hz), 1.55–1.85 (4H, m), 3.05–3.75 (4H, m), 3.86–4.38 (4H, m), 5.10–5.53 (4H, m), 7.54 (2H, d, J=9 Hz), 7.67 (2H, d, J=9 Hz), 8.26 (4H, d, J=8 Hz)

EXAMPLE 9

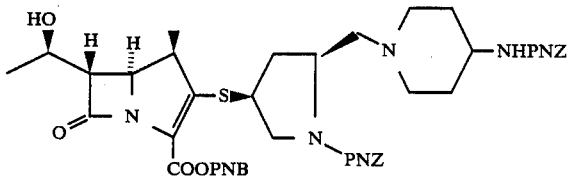

4-Nitrobenzyl (4R,5S,6S)-6-[(1R)-1-hydroxyethyl]-3-(2S,4S)-2-{4-(4-nitrobenzyloxycarbonylamino)piperidin-1-yl}methyl-1-(4-nitrobenzyloxycarbonyl)pyrrolidin-4-yl]thio-4-methyl-7-oxo-1-azabicyclo[3.2.0]hept-2-ene-2-carboxylate was obtained in 55.3% yield in substantially the same manner as that of Example 1.

IR (Nujol): 1765, 1710–1690, 1610 cm$^{-1}$

NMR (CDCl$_3$, δ): 1.25 (3H, d, J=6 Hz), 1.33 (3H, d, J=6 Hz), 5.03–5.49 (4H, m), 7.50 (2H, d, J=8 Hz), 7.66 (2H, d, J=9 Hz), 8.22 (4H, d, J=9 Hz)

EXAMPLE 10

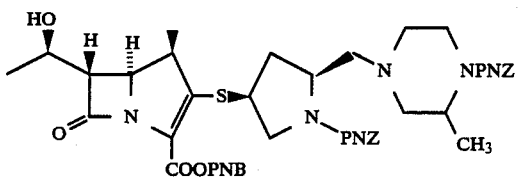

4-Nitrobenzyl (4R,5S,6S)-6-[(1R)-1-hydroxyethyl]-3-[(2S,4S)-2-{3-methyl-4-(4-nitrobenzyloxycarbonyl)piperazin-1-yl}methyl-1-(4-nitrobenzyloxycarbonyl)pyrrolidin-4-yl]thio-4-methyl-7-oxo-1-azabicyclo[3.2.0]hept-2-ene-2-carboxylate was obtained in 64.6% yield in substantially the same manner to that of Example 1.

IR (Nujol): 1765, 1710, 1790, 1605, 1515 cm$^{-1}$

NMR (CDCl$_3$, δ): 1.30 (6H, m), 1.37 (3H, d, J=6 Hz), 5.10–5.65 (4H, m), 7.55 (2H, d, J=8 Hz), 7.70 (2H, d, J=8 Hz), 8.28 (4H, d, J=8 Hz)

EXAMPLE 11

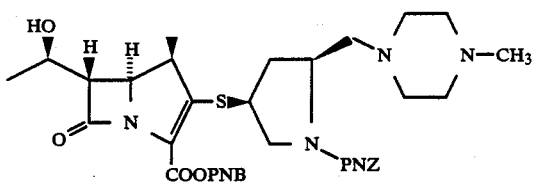

To a solution of 4-nitrobenzyl (4R)-2-diazo-4-[(2R,3S)-3-{(1R)-1-hydroxyethyl}-4-oxoazetidin-2-yl]-3-oxopentanoate (1.50 g) in 1,2-dichloroethane (30 ml) was added rhodium(II) acetate (5 mg) under refluxing. After refluxing for 30 minutes, the reaction mixture was cooled and evaporated in vacuo to give a residue. The residue was dissolved in anhydrous acetonitrile (10 ml) and then evaporated. This operation was repeated once again and the residue was dried in vacuo to give 4-nitrobenzyl (4R,5R,6S)-6-[(1R)-1-hydroxyethyl]-4-methyl-3,7-dioxo-1-azabicyclo[3.2.0]heptane-2-carboxylate.

The compound obtained was dissolved in anhydrous acetonitrile (30 ml) and cooled to 0° C. under an atmosphere of nitrogen. To this solution were added diphenyl phosphorochloridate (0.84 ml) and N,N-diisopropyl-N-ethylamine (0.74 ml) successively and the solution was stirred at 0° C. for 40 minutes. To the resulting solution were added dropwise a solution of (2S,4S)-4-mercapto-2-(4-methylpiperazin-1-yl)methyl-1-(4-nitrobenzyloxycarbonyl)pyrrolidine (1.97 g) in acetonitrile (10 ml) and N,N-diisopropyl-N-ethylamine (0.87 ml) with stirring at 5° C., and the stirring was continued at the same temperature for 2 hours. To the reaction mixture was added ethyl acetate (50 ml) and water (20 ml) with stirring, and the organic layer was separated. This layer was washed with saturated aqueous sodium chloride solution (40 ml×3), dried over magnesium sulfate and evaporated. The residue was chromatographed on silica gel (100 g) eluting with a mixture of chloroform and methanol (9:1 V/V). The fractions containing the desired compound were collected and evaporated in vacuo to give 4-nitrobenzyl (4R,5S,6S)-6-[(1R)-1-hydroxyethyl]-3-[(2S,4S)-2-(4-methylpiperazin-1-yl)methyl-1-(4-nitrobenzyloxycarbonyl)pyrrolidin-4-yl]thio-4-methyl-7-oxo-1-azabicyclo[3.2.0]hept-2-ene-2-carboxylate (2.38 g).

IR (Nujol): 1760–1750, 1690, 1525 cm$^{-1}$

NMR (CDCl$_3$, δ): 1.26 (3H, d, J=6 Hz), 1.33 (3H, d, J=6 Hz), 1.80–2.18 (2H, m), 2.27 (3H, s), 5.10–5.63 (4H, m), 7.48 (2H, d, J=8 Hz), 7.62 (2H, d, J=8 Hz), 8.16 (4H, d, J=8 Hz)

EXAMPLE 12

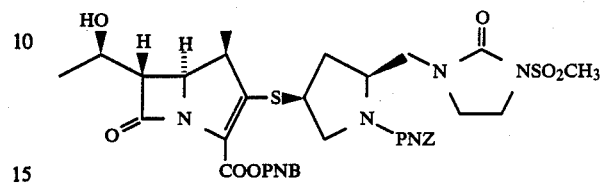

4-Nitrobenzyl (4R,5S,6S)-6-[(1R)-1-hydroxyethyl]-3-[(2S,4S)-2-(3-methylsulfonyl-2-oxoimidazolidin-1-yl)methyl-1-(4-nitrobenzyloxycarbonyl)pyrrolidin-4-yl]thio-4-methyl-7-oxo-1-azabicyclo[3.2.0]hept-2-ene-2-carboxylate was obtained in 49.5% yield in substantially the same manner as that of Example 1.

IR (Nujol): 1765, 1710–1700, 1605, 1520, 1350 cm$^{-1}$

NMR (CDCl$_3$, δ): 1.27 (3H, d, J=8 Hz), 1.36 (3H, d, J=6 Hz), 1.60–2.05 (3H, m), 2.36–2.86 (1H, m), 3.20–4.40 (18H, m), 5.12–5.67 (4H, m), 7.56 (2H, d, J=9 Hz), 7.69 (2H, d, J=9 Hz), 8.26 (4H, d, J=9 Hz)

EXAMPLE 13

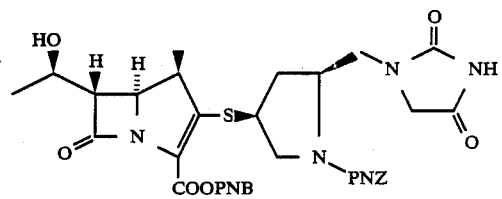

4-Nitrobenzyl (4R,5S,6S)-3-[(2S,4S)-2-(2,4-dioxoimidazolidin-1-yl)methyl-1-(4-nitrobenzyloxycarbonyl)-pyrrolidin-4-yl]thio-6-[(1R)-1-hydroxyethyl]-4-methyl-7-oxo-1-azabicyclo[3.2.0]hept-2-ene-2-carboxylate was obtained in 50% yield in substantially the same manner as that of Example 1.

NMR (CDCl$_3$+DMSO-d$_6$, δ): 1.28 (3H, d, J=7 Hz), 1.32 (3H, d, J=7 Hz), 3.15–4.45 (11H, m), 5.15–5.65 (4H, m), 7.58 (2H, d, J=8 Hz), 7.68 (2H, d, J=8 Hz), 8.26 (4H, d)

EXAMPLE 14

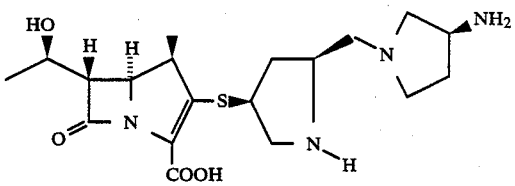

(4R,5S,6S)-3-[(2S,4S)-2-}(3S)-3-Aminopyrrolidin-1-yl}methylpyrrolidin-4-yl]thio-6-[(1R)-1-hydroxyethyl]-4-methyl-7-oxo-1-azabicyclo[3.2.0]hept-2-ene-2-carboxylic acid was obtained in 54.1% yield by catalytic reduction in substantially the same manner as that of Example 2.

mp: >187° C. (dec.)

IR (Nujol): 1755–1740, 1580–1560 cm$^{-1}$

NMR (D₂O, δ): 1.20 (3H, d, J=7 Hz), 1.27 (3H, d, J=6 Hz), 1.46-2.06 (2H, m), 2.27-4.35 (17H, m)

SI Mass: 411 (M+)

EXAMPLE 15

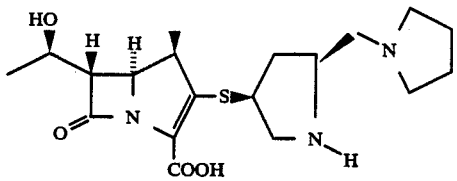

(4R,5S,6S)-6-[(1R)-1-Hydroxyethyl]-3-[(2S,4S)-2-(pyrrolidin-1-yl)methylpyrrolidin 4-yl]thio-4-methyl-7-oxo-1-azabicyclo[3.2.0]hept-2-ene-2-carboxylic acid was obtained in 59.7% yield by catalytic reduction in substantially the same manner as that of Example 2.

mp: >193° C. (dec.)

IR (Nujol): 1750, 1590, 1150 cm⁻¹

NMR (D₂O, δ): 1.20 (3H, d, J=8 Hz), 1.27 (3H, d, J=8 Hz), 1.83-2.26 (4H, m), 2.42-3.10 (3H, m)

SI Mass: 396 (M+)

EXAMPLE 16

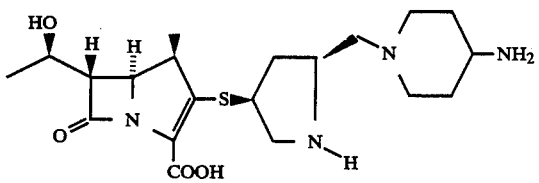

(4R,5S,6S)-3-[(2S,4S)2-{4-Aminopiperidin-1-yl}methylpyrrolidin 4-yl]thio-6-[(1R)-1-hydroxyethyl]-4-methyl-7-oxo-1-azabicyclo[3.2.0]hept-2-ene-2-carboxylic acid was obtained in 26.7% yield by catalytic reduction in substantially the same manner as that of Example 2.

mp: >195° C. (dec.)

IR (Nujol): 1755-1740, 1590-1560 cm⁻¹

NMR (D₂O, δ): 1.21 (3H, d, J=7 Hz), 1.27 (3H, d, J=7 Hz), 1.46-1.86 (2H, m), 1.92-2.43 (4H, m)

SIMS: 425 (M+)

EXAMPLE 17

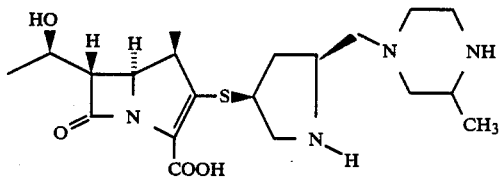

(4R,5S,6S)-6-[(1R)-1-Hydroxyethyl]-3-[(2S,4S)-2-{3-methylpiperazin-1-yl}methylpyrrolidin-4-yl]thio-4-methyl-7-oxo-1-azabicyclo[3.2.0]hept-2-ene-2-carboxylic acid was obtained in 28.9% yield by catalytic reduction in substantially the same manner as that of Example 2.

mp: >196° C. (dec.)

IR (Nrjol): 1755, 1585-1560 cm⁻¹

NMR (D₂O, δ): 1.18 (3H, d, J=8 Hz), 1.25 (6H, d, J=8 Hz), 4.13-4.35 (2H, m)

SI Mass: 425 (M+)

EXAMPLE 18

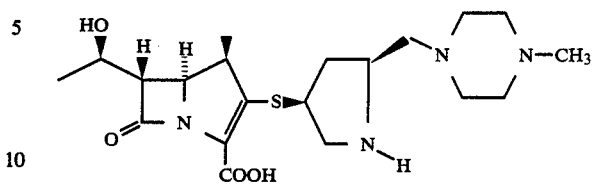

A mixture of 4-nitrobenzyl (4R,5S,6S)-6-[-(1R)-1-hydroxyethyl]-3-[(2S,4S)-2-(4-methylpiperazin-1-yl)methyl-1-(4-nitrotenzyloxycarbonyl)pyrrolidin-4-yl]thio-4-methyl-7-oxo-1-azabicyclo[3.2.0]hept-2-ene-2-carboxylate (1.40 g), 20% palladium hydroxide on carbon (0.7 g), 0.2M sodium acetate-acetic acid buffer (pH=5.8, 50 ml) and tetrahydrofuran (50 ml) was stirred for 5 hours under atmospheric pressure of hydrogen at ambient temperature. After the catalyst was filtered off, the filtrate was evaporated in vacuo to remove the organic solvent. The aqueous layer was washed twice with ethyl acetate (20 ml) and evaporated in vacuo to remove the organic solvent. The residue was chromatographed on nonionic adsorption resin, "Diaion HP-20" (trademark, made by Mitsubishi Chemical Industries) (50 ml) eluting in turn with water (100 ml) and 10% aqueous acetone (200 ml). The fractions containing the desired compound were collected and hydrophilized to give (4R,5S,6S)-6-[(1R)-1-hydroxyethyl]-3-[(2S,4S)-2-(4-methylpiperazin-1-yl)methylpyrrolidin-4-yl]thio-4-methyl-7-oxo-1-azabicyclo[3.2.0-]hept-2-ene-2-carboxylic acid (0.40 g).

mp: >145° C. (dec.)

IR (Nujol): 1760-1735, 1600-1580 cm⁻¹

NMR (D₂O, δ): 1.23 (3H, d, J=8 Hz), 1.28 (3H, d, J=8 Hz), 1.45-1.85 (1H, m), 2.30-2.66 (3H, m), 2.88 (3H, s)

FB Mass: 425 (M+)

EXAMPLE 19

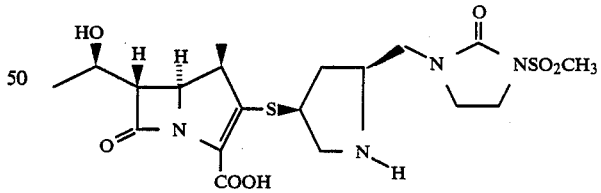

(4R,5S,6S)-6-[(1R)-1-Hydroxyethyl]-3-[(2S,4S)-2-(3--methylsulfonyl-2-oxoimidazolidin-1-yl)methylpyrrolidin-4-yl]thio-4-methyl-7-oxo-1-azabicyclo[3.2.0]hept-2-ene-2-carboxylic acid was obtained in 67.8% yield by catalytic reduction in substantially the same manner as that of Example 2.

mp: >183° C. (dec.)

IR (Nujol): 1755, 1720, 1680, 1350, 1165 cm⁻¹

NMR (D₂O, δ): 1.21 (3H, d, J=7 Hz), 1.28 (3H, d, J=6 Hz), 1.50-2.00 (1H, m), 2.55-3.00 (1H, m), 3.31 (3H, s), 3.36-4.33 (14H, m)

SI Mass: 489 (M+), 488 (M+ −1), 487 (M+ −2)

EXAMPLE 20

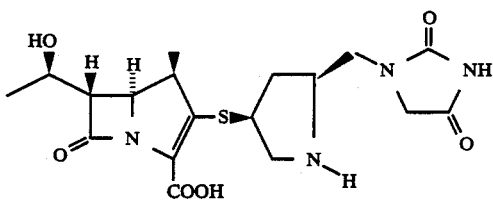

(4R,5S,6S)-3-[(2S,4S)-2-(2,4-Dioxoimidazolidin-1-yl)methylpyrrolidin-4-yl]thio-6-[(1R)-1-hydroxyethyl]-4-methyl-7-oxo-1-azabicyclo[3.2.0]hept-2-ene-2-carboxylic acid was obtained in 56.9% yield by catalytic reduction in substantially the same manner as that of Example 2.

mp: >191° C. (dec.)
IR (Nrjol): 1760–1750, 1720, 1590–1580 cm$^{-1}$
NMR (D$_2$O, δ): 1.22 (3H, d, J=9 Hz), 1.29 (3H, d, J=9 Hz), 1.45–2.00 (2H, m), 2.50–3.05 (1H, m), 3.20–4.45 (11H, m)
Mass: 425 (M$^+$+1)

EXAMPLE 21

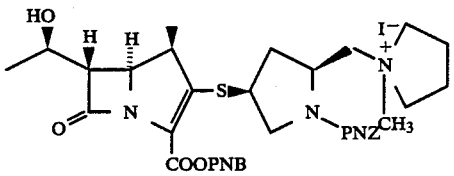

To a solution of 4-nitrobenzyl (4R,5S,6S)-6-[(1R)-1-hydroxyethyl]-3-[(2S,4S)-1-(4-nitrobenzyloxycarbonyl)-2-(pyrrolidin-1-yl)methylpyrrolidin-4-yl]thio-4-methyl-7-oxo-1-azabicyclo[3.2.0]hept-2-ene-2-carboxylate (0.35 g) in acetone (3.5 ml) was added methyl iodide (0.15 ml) at ambient temperature. The mixture was stirred for hours. The reaction mixture was evaporated in vacuo to give 4-nitrobenzyl (4R,5S,6S)-6-[(1R)-1-hydroxyethyl]-3-[(2S,4S)-2-(1-methyl-1-pyrrolidinio)methyl-1-(4-nitrobenzyloxycarbonyl)pyrrolidin-4-yl]thio-4-methyl-7-oxo-1-azabicyclo[3.2.0]hept-2-ene-2-carboxylate iodide (0.35 g).

EXAMPLE 22

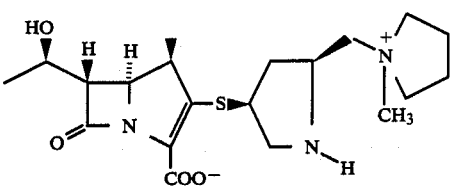

(4R,5S,6S)-6-[(1R)-1-Hydroxyethyl]-3-[(2S,4S)-2-(1-methyl-1-pyrrolidinio)methylpyrrolidin-4-yl]thio-4-methyl-7-oxo-1-azabicyclo[3.2.0]hept-2-ene-2-carboxylate was obtained in 78.1% yield by catalytic reduction in substantially the same manner as that of Example 2.

mp: >178° C. (dec.)
IR (Nujol): 1750, 1590, 1140 cm$^{-1}$
NMR (E$_2$O, δ): 1.20 (3H, d, J=8 Hz), 1.28 (3H, d, J=6 Hz), 1.40–1.90 (1H, m), 2.00–2.40 (4H, m), 2.56–3.00 (2H, m), 3.12 (3H, s)
SI Mass: 410 (M$^+$)

EXAMPLE 23

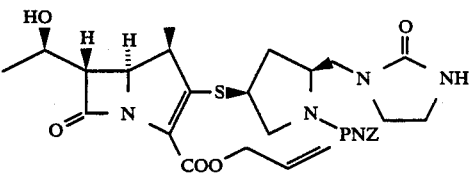

Allyl (4R,5S,6S)-6-[(1R)-1-hydroxyethyl]-4-methyl-3-[(2S,4S)-1-(4-nitrobenzyloxycarbonyl)-2-(2-oxoimidazolidin-1-yl)methylpyrrolidin-4-yl]thio-7-oxo-1-azabicyclo[3.2.0]hept-2-ene-2-carboxylate was obtained in 38.0% yield in substantially the same manner as that of Example 1.

This compound was immediately used as the starting compound of Example 46.

The compounds listed in Table 1 were obtained in substantially the same manner as that of Example 1.

TABLE 1

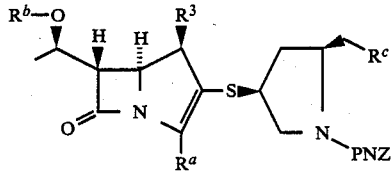

| Example No. | R$^a$ | R$^b$ | R$^3$ | R$^c$ | data |
|---|---|---|---|---|---|
| 24 | COOPNB | H | CH$_3$ | —N⟨⟩N—CONH$_2$ | IR(Neat: 1765, 1710–1690, 1620, 1580, 1525 cm$^{-1}$ NMR(CDCl$_3$, δ): 1.27(3H, d, J=7Hz), 1.35(3H, d, J=7Hz), 7.52(2H, d, J=8Hz), 7.67(2H, d, J=8Hz), 8.25(4H, d, J=8Hz) |
| 25 | " | " | " | —N⟨⟩NH 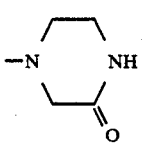 | IR(Neat): 1775–1765, 1700, 1605, 1525, cm$^{-1}$ |

TABLE 1-continued

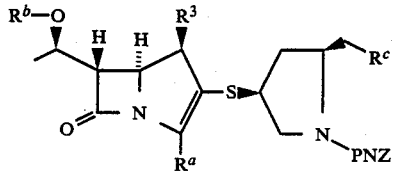

| Example No. | $R^a$ | $R^b$ | $R^3$ | $R^c$ | data |
|---|---|---|---|---|---|
| 26 | " | " | " | 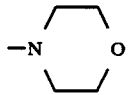 | IR(Nujol): 1765, 1700, 1605, 1520, 1350 cm$^{-1}$<br>NMR(CDCl$_3$, δ): 1.28(3H, d, J=7Hz), 1.36(3H, d, J=7Hz), 1.52-2.05(2H, m), 2.25-2.83(7H, m), 3.18-3.50(3H, m), 3.53-3.86(5H, m), 3.90-4.45(4H, m), 5.12-5.68(4H, m), 7.57(2H, d, J=8Hz), 7.58(2H, d, J=8Hz), 8.26(4H, d, J=8Hz) |
| 27 | " | " | " | 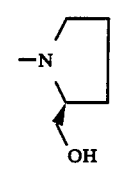 | IR(Nujol): 1765, 1710-1685, 1610, 1520 cm$^{-1}$<br>NMR(CDCl$_3$, δ): 1.30(3H, d, J=6Hz), 1.38(3H, d, J=6Hz), 5.20-5.52(4H, m), 7.56(2H, d, J=9Hz), 7.69(2H, d, J=9Hz), 8.28(4H, d, J=9Hz) |
| 28 | COOPNB | H | CH$_3$ | 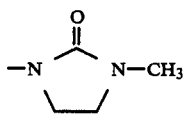 | IR(Nujol): 1760, 1710-1670, 1600, 1520 cm$^{-1}$<br>NMR(CDCl$_3$, δ): 1.28(3H, d, J=7Hz), 1.36(3H, d, J=7Hz), 1.80-2.15 (1H, m), 2.30-2.70(1H, m), 2.77 (3H, s), 3.10-3.75(10H, m), 3.90-4.36(4H, m), 5.12-5.60(4H, m), 7.52(2H, d, J=9Hz), 7.62(2H, d, J=9Hz), 8.20(4H, d, J=9Hz) |
| 29 | 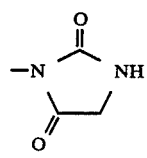 | " | " | 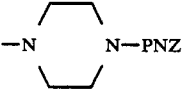 | IR(Nujol): 1770-1750, 1710-1690, 1605, 1525, cm$^{-1}$<br>NMR(CDCl$_3$, δ): 1.25(3H, d, J=7Hz), 1.33(3H, d, J=7Hz), 2.38-2.80(1H, m), 5.45-5.73(1H, m), 5.80-6.23 (1H, m), 7.50-7.65(2H, m), 8.18(2H, d, J=8Hz) |
| 30 | COOPNB | PNZ | H | —N⟨⟩N—PNZ | IR(Nujol): 1780-1770, 1710, 1790, 1605, 1515 cm$^{-1}$ |

The following compound was obtained in substantially the same manner as that of Example 1.

EXAMPLE 31

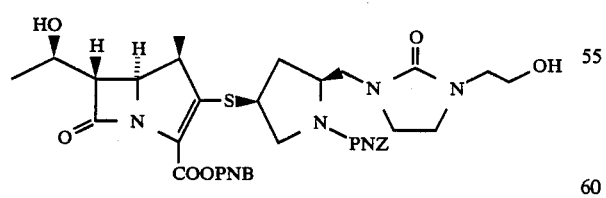

IR (Neat): 1770-1760, 1710-1680, 1610, 1525 cm$^{-1}$
NMR (CDCl$_3$, δ): 1.26 (3H, d, J=6 Hz), 1.33 (3H, d, J=7 Hz), 1.72-2.08 (2H, m), 2.28-2.75 (2H, m), 3.07-4.43 (18H, m), 5.06-5.60 (4H, m), 7.49 (2H, d, J=8 Hz), 7.60 (2H, d, J=8 Hz), 8.18 (4H, d, J=8 Hz)

The compounds listed in Table 2 were obtained in substantially the same manner as that of Example 21.

TABLE 2

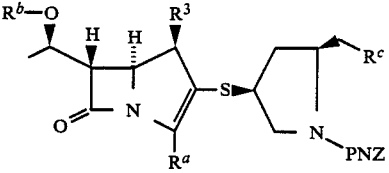

| Example No. | $R^a$ | $R^b$ | $R^3$ | $R^c$ |
|---|---|---|---|---|
| 32 | COOPNB | H | CH$_3$ | 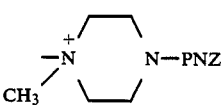 |

TABLE 2-continued

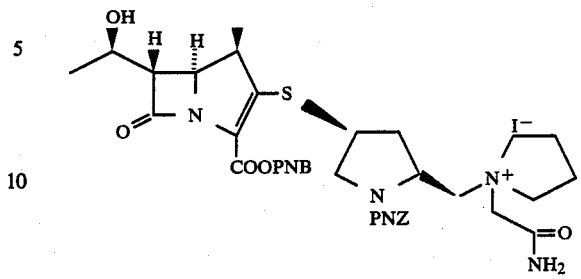

| Example No. | $R^a$ | $R^b$ | $R^3$ | $R^c$ |
|---|---|---|---|---|
| 33 | " | PNZ | H | ![piperazine with N-methyl and N-PNZ] |

These compounds were immediately used as the starting compounds of Examples 41 and 42, respectively.

EXAMPLE 34

To a solution of 4-nitrobenzyl (4R,5S,6S)-6-[(1R)-1-hydroxyethyl]-3-[(2S,4S)-1-(4-nitrobenzyloxycarbonyl)-2-(pyrrolidin-1 -yl)methylpyrrolidin-4-yl]thio-4-methyl-7-oxo-1-azabicyclo[3.2.0]hept-2-ene-2-carboxylate (0.77 g) in acetone (8 ml) was added iodoacetamide (0.93 g) at ambient temperature. The mixture was stirred overnight at the same temperature. The reaction mixture was evaporated in vacuo to give 4-nitrobenzyl (4R,5S,6S)-6-[(1R)-1-hydroxyethyl]-3-[(2S,4S)-2-(1-carbamoylmethylpyrrolidinio)methyl-1-(4-nitrobenzyloxycarbonyl)pyrrolidin-4-yl]thio-4-methyl-7-oxo-1-azabicyclo[3.2.0]hept-2-ene-2-carboxylate iodide (0.71 g).

IR (Nujol): 1760, 1710, 1690, 1605, 1520 cm$^{-1}$

NMR (CDCl$_3$+DMSO-d$_6$, δ): 1.25 (3H, d, J=7 Hz), 1.27 (3H, d, J=7 Hz), 1.80-2.50 (6H, m), 7.61 (2H, d, J=8 Hz), 7.82 (2H, d, J=8 Hz), 8.23 (2H, d, J=8 Hz), 8.27 (2H, d, J=8 Hz).

The compounds listed in Table 3 were obtained in substantially the same manner as that of Example 2 or 48.

TABLE 3

| Example No. | $R^a$ | $R^3$ | $R^c$ | data |
|---|---|---|---|---|
| 35 | COOH | CH$_3$ | —N⟨piperazine⟩N—CONH$_2$ | IR(Nujol): 1755-1745, 1660 cm$^{-1}$<br>NMR(D$_2$O, δ): 1.20(3H, d, J=7Hz), 1.29(3H, d, J=7Hz), 1.50-2.05 (2H, m), 2.37-2.96(6H, m), 3.20-3.58(8H, m)<br>mp: >193° C. (dec.) |
| 36 | " | " | —N⟨ring⟩NH with C=O | IR(Nujol): 1755-1735, 1590-1580 cm$^{-1}$<br>NMR(D$_2$O, δ): 1.20(3H, d, J=7Hz), 1.38(3H, d, J=7Hz), 2.80(3H, s),<br>mp: >189° C. (dec.) |
| 37 | " | " | —N⟨morpholine⟩O | IR(Nujol): 1755, 1695 cm$^{-1}$<br>NMR(D$_2$O, δ): 1.33(3H, d, J=7Hz), 1.32(3H, d, J=7Hz), 1.56-2.15 (1H, m), 2.30-3.00(4H, m)<br>SI Mass: 412(M$^+$)<br>mp: >191° C. (dec.) |

TABLE 3-continued

[Structure shown at top of table with HO, H, H, R³, S, R^c, O, N, R^a, N, H groups]

| Example No. | R^a | R³ | R^c | data |
|---|---|---|---|---|
| 38 | " | " | [pyrrolidinyl with CH₂OH group, —N with CH₂OH] | IR(Nujol): 1755, 1585 cm⁻¹<br>NMR(D₂O, δ): 1.22(3H, d, J=6Hz), 1.30(3H, d, J=6Hz), 1.75–2.35 (5H, m)<br>FB Mass: 4.26(M⁺) |
| 39 | COOH | CH₃ | [imidazolidinone: —N\_\_N—CH₃ with C=O] | IR(Nujol): 1750, 1680–1650, 1580 cm⁻¹<br>NMR(D₂O, δ): 1.20(3H, d, J=7Hz), 1.27(3H, d, J=7Hz), 1.52–2.10(1H, m), 2.75(3H, s).<br>FB Mass: 425(M⁺)<br>mp: 178° C. (dec.) |
| 40 | " | H | [piperazine: —N\_\_NH] | IR(Nujol): 1770–1740, 1650, 1640 cm⁻¹<br>NMR(D₂O, δ): 1.26(3H, d, J=7Hz), 1.50–1.80(1H, m), 2.50–3.03(8H, m), 3.05–3.50(6H, m), 3.53–4.38(6H, m) |
| 41 | COO⁻ | CH₃ | [N-methylpiperazinium: —N⁺(CH₃)\_\_NH] | IR(Nujol): 1755–1730, 1660–1640, 1590–1580 cm⁻¹<br>NMR(D₂O, δ): 1.22(3H, d, J=7Hz), 1.33 (3H, d, J=7Hz), 1.42–1.75(1H, m), 3.29(3H, s), 4.16–4.40(2H, m)<br>SI Mass: 425(M⁺)<br>mp: >194° C. (dec.) |
| 42 | COO⁻ | H | [N-methylpiperazinium: —N⁺(CH₃)\_\_NH] | IR(Nujol): 1755, 1580–1570 cm⁻¹<br>NMR(D₂O, δ): 1.26(3H, d, J=7Hz), 1.35–1.85(1H, m), 3.28(3H, s),<br>SI Mass: 411(M⁺)<br>mp: >182° C. (dec.) |
| 43 | COO⁻ | CH₃ | [pyrrolidinium with CONH₂: —N⁺\_\_CONH₂] | IR(Nujol): 1750, 1660–1645, 1585 cm⁻¹<br>NMR(D₂O, δ): 1.20(3H, d, J=7Hz), 1.27 (3H, d, 7Hz), 1.53–1.96(1H, m), 2.10–2.43(4H, m), 2.50–2.90(1H, m), 3.26–3.57(2H, m)<br>mp: 197° C. (dec.) |

The following compound was obtained in substantially the same manner as that of Example 2.

EXAMPLE 44

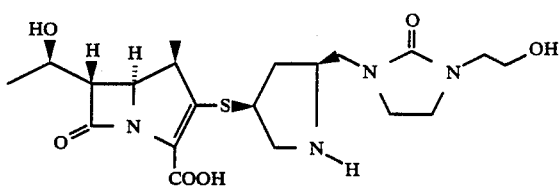

mp: >171° C. (dec.)
IR (Nujol): 1760–1740, 1670–1650 cm⁻¹
NMR (D₂O, δ): 1.22 (3H, d, J=7 Hz), 1.28 (3H, d, J=7 Hz), 1.55–1.96 (2H, m), 2.50–2.93 (1H, m), 3.20–4.33 (17H, m)
FB Mass: 455 (M⁺+1)

EXAMPLE 45

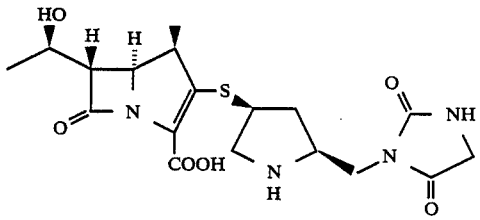

To a solution of allyl (4R,5S,6S)-6-[(1R)--1-hydroxyethyl]-3-[(2S,4S)-2-(2,5-dioxoimidazolidin-1-yl)methyl-1-(4-nitrobenzyloxycarbonyl)pyrrolidin-4-yl]thio-4-methyl-7-oxo-1-azabicyclo[3.2.0]hept-2-ene-2-carboxylate (1.44 g) in tetrahydrofuran (30 ml) were added triphenylphosphine (0.29 g), sodium 2-ethylhexanoate (0.41 g) and tetrakis(triphenylphosphine)palladium(0) (0.13 g) successively with stirring at ambient temperature After stirring at the same temperature for 1 hour, the reaction mixture was evaporated in vacuo to give a residue. A mixture of the residue, 20% palladium hydroxide on carbon (0.5 g), 0.1M phosphoric acid buffer (pH 5.8,60 ml) and tetrahydrofuran (60 ml) was stirred for 5 hours under atmospheric pressure of hydrogen at ambient temperature. After the catalyst was filtered off, the filtrate was evaporated in vacuo to remove the organic solvent. The residue was chromatographed on nonionic adsorption resin, "Diaion HP-20" (Trademark, made by Mitsubishi Chemical Industries)(30 ml) eluting in turn with water (80 ml) and 5% aqueous acetone (90 ml). The fractions containing the desired compound were collected and lyophilized to give (4R,5S,6S)-6-[(1R)-1-hydroxyethyl]-3-[(2S,4S)-2-(2,5-dioxoimidazolidin-1-yl)methylpyrrolidin-4-yl]thio-4-methyl-7-oxo-1-azabicyclo[3.2.0]hept-2-ene-2-carboxylic acid (0.40 g).

mp: >195° C. (dec.)

IR (Nujol): 1755, 1710, 1580 cm$^{-1}$

NMR (D$_2$O, δ): 1.20 (3H, d, J=7 Hz), 1.30 (3H, d, J=7 Hz), 1.53–1.98 (1H, m), 2.53–2.96 (1H, m), 3.12–4.38 (13H, m)

FB Mass: 425 (M$^+$+1)

EXAMPLE 46

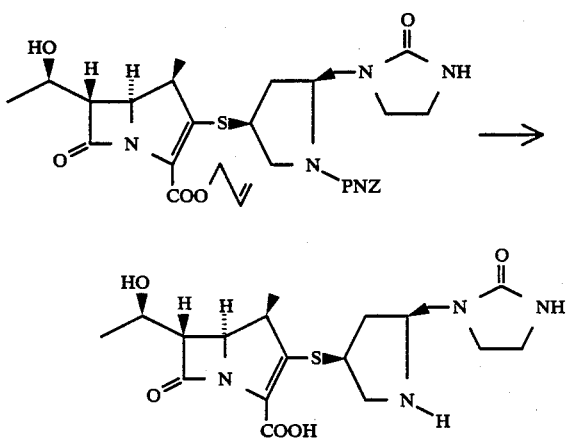

(4R,5S,6S)-6-[(1R)-1-Hydroxyethyl]-4-methyl-7-oxo-3-[(2S,4S)-2-(2-oxoimidazolidin-1-yl)methylpyrrolidin-4-yl]thio-1-azabicyclo[3.2.0]hept-2-ene-2-carboxylic acid was obtained by reacting allyl (4R,5S,6S)-6-[-(1R)-1-hydroxyethyl]-4-methyl-3-[(2S,4S)-1-(4-nitrobenzyloxycarbonyl)-2-(2-oxoimidazolidin-1-yl)methylpyrrolidin-4-yl]thio-7-oxo-1-azabicyclo[3.2.0]hept-2-ene-2-carboxylate in substantially the same manner as that of Example 48.

mp >184° C. (dec.)

IR (Nujol): 1760, 1690–1680, 1590, 1280 cm$^{-1}$

NMR (D$_2$O, δ): 1.21 (3H, d, J=7 Hz), 1.28 (3H, d, J=6 Hz), 1.50–2.15 (2H, m), 2.50–2.93 (1H, m), 3.20–4.35 (13H, m)

SI Mass: 411 (M$^+$+1)

EXAMPLE 47

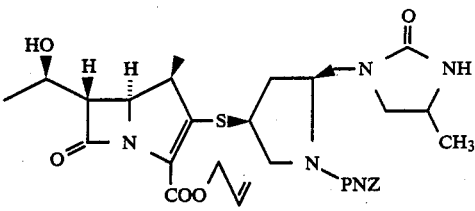

Allyl (4R,5S,6S)-6-[(1R)-1-hydroxyethyl]-4-methyl-3-[(2S,4S)-2-(4-methyl-2-oxoimidazolidin-1-yl)methyl-1-(4-nitrobenzyloxycarbonyl)pyrrolidin-4-yl]thio-7-oxo-1-azabicyclo[3.2.0]hept-2-ene-2-carboxylate was obtained in 66.7% yield in substantially the same manner as that of Example 1.

IR (Neat): 1770, 1710–1690, 1525 cm$^{-1}$

NMR (CDCl$_3$, δ): 1.03–1.46 (9H, m), 1.73–2.10 (2H, m), 2.32–2.70 (2H, m), 2.73–3.86 (8H, m), 3.90–4.36 (4H, m), 4.50–4.95 (3H, m), 5.10–5.55 (4H, m), 5.70–6.20 (1H, m), 7.55 (2H, d, J=8 Hz), 8.19 (2H, d, J=8 Hz)

EXAMPLE 48

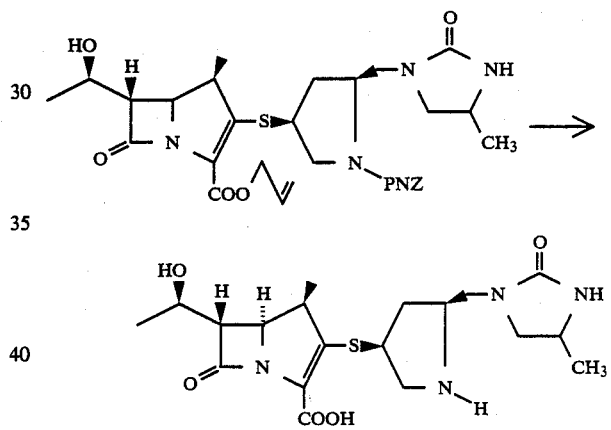

To a solution of allyl (4R,5S,6S)-6-[(1R)-1-hydroxyethyl]-4-methyl-3-{(2S,4S)-2-(4-methyl-2-oxoimidazolidin-1-yl)methyl-1-(4-nitrobenzyloxycarbonyl)pyrrolidin-4-yl]thio-7-oxo-1-azabicyclo[3.2.0-]hept-2-ene-2-carboxylate (2.45 g) in tetrahydrofuran (50 ml) were added triphenylphosphine (0.50 g), sodium 2-ethyl hexanoate (0.70 g) and tetrakis(triphenylphosphine)palladium(0) (0.22 g) successively with stirring at ambient temperature. After stirring at the same temperature for 1 hour, the reaction mixture was evaporated in vacuo to give a residue. A mixture of the residue, 20% palladium hydroxide on carbon (0.5 g), 0.1M phosphoric acid buffer (pH=6.0, 80 ml) and tetrahydrofuran (80 ml) was stirred for 5 hours under atmospheric pressure of hydrogen at ambient temperature. After the catalyst was filtered off, the filtrate was evaporated in vacuo to remove the organic solvent. The residue was chromatographed on nonionic adsorption resin, "Diaion HP-20" (trademark, made by Mitsubishi Chemical Industries) (30 ml) eluting in turn with water (90 ml) and 5% aqueous acetone (100 ml). The fractions containing the desired compound were collected and lyophilized to give (4R,5S,6S)-6-[(1R)-1-hydroxyethyl]-4--methyl-3-[(2S,4S)-2-(4-methyl-2-oxoimidazolidin-1- yl)methylpyrrolidin-4-yl]thio-7-oxo-1-azabicyclo[3.2.0-]hept-2-ene-2-carboxylic acid (0.29 g).

mp: >183° C. (dec.)

IR (Nujol): 1760–1740, 1680–1650, 1580 cm$^{-1}$

NMR (D$_2$O, δ): 1.00–1.40 (9H, m), 1.54–2.15 (1H, m), 2.50–2.95 (2H, m), 3.00–4.40 (13H, m)

FB Mass: 425 (M$^+$)

EXAMPLE 49

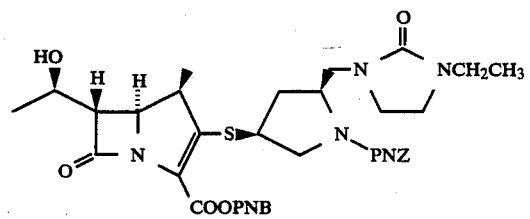

4-Nitrobenzyl (4R,5S,6S)-3-[(2S,4S)-2-(3-ethyl-2-oxoimidazolidin-1-yl)methyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate was obtained in 71.1% yield in substantially the same manner as that of Example 1.

IR (Neat): 1770, 1710–1690, 1610, 1525, 1495 cm$^{-1}$

NMR (CDCl$_3$, δ): 1.06 (3H, t, J=7 Hz), 1.26 (3H, d, J=7 Hz), 1.34 (3H, d, J=7 Hz), 1.80–2.75 (5H, m), 3.10–3.90 (10H, m), 3.88–4.42 (4H, m), 5.12–5.65 (4H, m), 7.56 (2H, d, J=9 Hz), 7.66 (2H, d, J=9 Hz), 8.25 (4H, d, J=9 Hz)

EXAMPLE 50

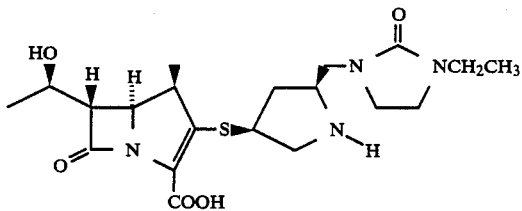

(4R,5S,6S)-3-[(2S,4S)-2-(3-Ethyl-2-oxoimidazolidin-1-yl)methylpyrrolidin-4-yl]thio-6-[(1R)-1-hydroxyethyl]-4-methyl-7-oxo-1-azabicyclo[3.2.0]hept-2-ene-2-carboxylic acid was obtained in 76.8% yield in substantially the same manner as that of Example 2.

IR (Neat): 1770, 1690, 1635, 1500 cm$^{-1}$

NMR (D$_2$O, δ): 1.08 (3H, t, J=7 Hz), 1.22 (3H, d, J=7 Hz), 1.30 (3H, d, J=6 Hz), 1.58–2.03 (1H, m), 2.53–2.94 (1H, m), 3.06–4.34 (16H, m)

FB Mass: 439 (M$^+$+1)

EXAMPLE 51

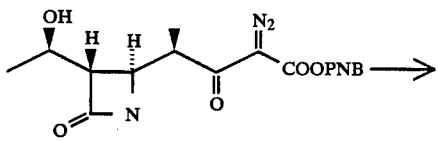

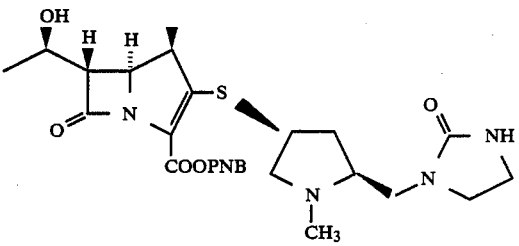

To a solution of 4-nitrobenzyl (4R)-2-diazo-4-[(2R,3S)-3-{(1R)-1-hydroxyethyl}-4-oxoazetidin-2-yl]-3-oxopentanoate (1.0 g) in dichloroethane (10 ml) was added rhodium(II) octanoate (10 mg) under refluxing. After refluxing for 30 minutes, the reaction mixture was cooled and evaporated in vacuo to give a residue. The residue was dissolved in benzene (5 ml) and then evaporated in vacuo to give 4-nitrobenzyl (4R,5R,6S)-6-[(1R)-1-hydroxyethyl]-4-methyl-3,7-dioxo-1-azabicyclo[3.2.0]heptane-2-carboxylate.

The compound obtained above was dissolved in acetonitrile (10 ml) and cooled to 0° C.–2° C. under atmosphere of nitrogen. To this solution were added diphenyl phosphorochloridate (0.56 ml) and N,N-diisopropyl-N-ethylamine (0.49 ml) successively and the mixture was stirred at the same temperature for 40 minutes. To the resulting solution were added dropwise a solution of (2S,4S)-4-mercapto-1-methyl-2-(2-oxoimidazolidin-1-yl)methyl-pyrrolidine (0.60 g) in acetonitrile (6 ml) and N,N-diisopropyl-N-ethylamine (0.49 ml) with stirring at 0°–2° C., and the mixture was stirred at the same temperature for 2 hours.

To a reaction mixture was added ethyl acetate (50 ml) and the solution was washed twice with aqueous sodium chloride, dried over anhydrous magnesium sulfate and evaporated in vacuo. The resulting residue was chromatographed on silica gel (100 g) eluting with a mixture of chloroform and methanol (19:1 V/V). The fractions containing the desired compound were collected and evaporated in vacuo to give 4-nitrobenzyl (4R,5S,6S)-6-[(1R)-1-hydroxyethyl]-3-[(2S,4S)-1-methyl-2-(2-oxoimidazolidin-1-yl)methylpyrrolidin-4-yl]thio-4-methyl-7-oxo-1-azabicyclo[3.2.0]hept-2-ene-2-carboxylate (0.49 g).

IR (Nujol): 1760, 1670, 1590, 1520, 1345 cm$^{-1}$

NMR (CDCl$_3$, δ): 1.19 (3H, d, J=7 Hz), 1.32 (3H, d, J=7 Hz), 2.25 (3H, s), 5.17 (1H, d, J=14 Hz), 5.46 (1H, d, J=14 Hz), 7.62 (2H, d, J=9 Hz), 8.18 (2H, d, J=9 Hz)

EXAMPLE 52

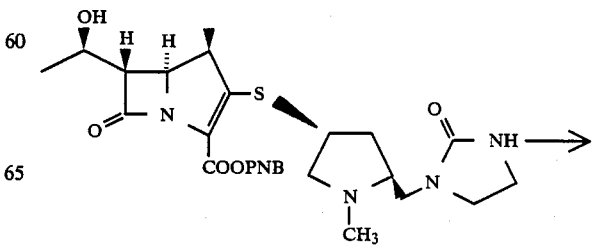

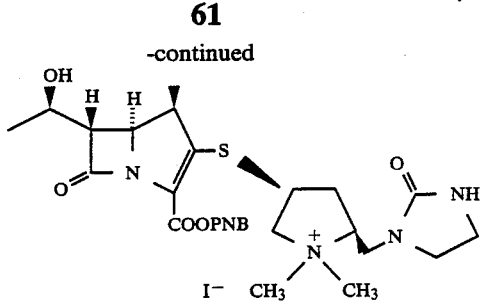

To a solution of 4-nitrobenzyl (4R,5S,6S)-6-[(1R)-1-hydroxyethyl]-3-[(2S,4S)-1-methyl-2-(2-oxoimidazolidin-1-yl)methylpyrrolidin-4-yl]thio-4-methyl-7-oxo-1-azabicyclo[3.2.0]hept-2-ene-2-carboxylate (0.47 g) in acetone (5 ml) was added methyl iodide (0.52 ml) and the mixture was stirred at ambient temperature for 7 hours. The resulting precipitates were collected, washed with acetone (10 ml) and dried in vacuo to give 4-nitrobenzyl (4R,5S,6S)-6-(1R)-1-hydroxyethyl]-3-[(2S,4S)-1,1-dimethyl-2-(2-oxoimidazolidin-1-yl)methyl-4-pyrrolidinio]thio-4-methyl-7-oxo-1-azabicyclo[3.2.0]hept-2-ene-2-carboxylate iodide (0.22 g).

NMR (DMSO-d6, δ): 1.16 (3H, d, J=6 Hz), 1.17 (3H, d, J=8 Hz), 2.75–2.93 (1H, m), 3.14 (3H, s), 3.16 (3H, s), 3.70–4.28 (6H, m), 5.12 (1H, d, J=5 Hz), 5.32 (1H, d, J=14 Hz), 5.50 (1H, d, J=14 Hz), 7.72 (2H, d, J=8.5 Hz), 8.25 (2H, d, J=8.5 Hz)

EXAMPLE 53

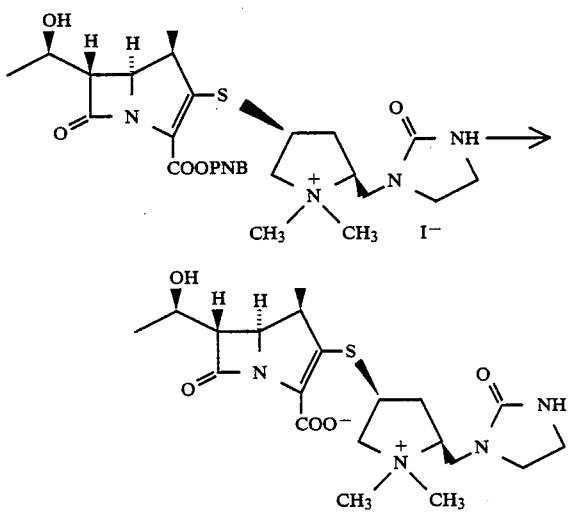

A mixture of 4-nitrobenzyl (4R,5S,6S)-6-[(1R)-1-hydroxyethyl]-3-[(2S,4S)-1,1-dimethyl-2-(2-oxoimidazolidin-1-yl)methyl-4-pyrrolidinio]thio-4-methyl-7-oxo-1-azabicyclo[3.2.0]hept-2-ene-2-carboxylate iodide (0.21 g), 20% palladium hydroxide on carbon (0.20 g), 0.1M phosphoric acid buffer (pH 5.8, 10ml) and tetrahydrofuran (10 ml) was stirred for 5 hours under atmospheric pressure of hydrogen at ambient temperature. After the catalyst was filtered off, the filtrate was evaporated in vacuo to remove the organic solvent. The resulting aqueous solution was washed twice with ethyl acetate (15 ml) and concentrated in vacuo to remove the organic solvent. The residue was chromatographed on nonionic adsorption resin, Diaion HP-20 (20 ml) eluting in turn with water (40 ml) and 5% aqueous acetone (60 ml). The fractions containing the desired compound were collected and lyophilized to give (4R,5S,6S)-6-[(1R)-1-hydroxyethyl]-3-[(2S,4S)-1,1-dimethyl-2-(2-oxoimidazolidin-1-yl)methyl-4-pyrrolidinio]thio-4-methyl-7-oxo-1-azabicyclo[3.2.0]hept-2-ene-2-carboxylate (125 mg).

IR (Nujol): 1750–1740, 1670–1640, 1590, 1500, 1280 cm$^{-1}$

NMR (D2O, δ): 1.21 (3H, d, J=8 Hz), 1.28 (3H, d, J=7 Hz), 1.40–1.80 (1H, m), 1.83–2.26 (1H, m), 2.24 (6H, s), 3.35–4.33 (13H, m)

FB Mass: 439 (M+)

PREPARATION 52-(1)

A solution of L-alanine methyl ester hydrochloride (39.2 g) and potassium cyanate (34.1 g) in tetrahydrofuran (300 ml) and water (150 ml) was stirred at 50°–60° C. for 1 hour and then stirred at 100° C. for 30 minutes. The reaction mixture was extracted with tetrahydrofuran (300 ml) and a mixture of tetrahydrofuran (20 ml) and water (100 ml). The extract was washed with aqueous sodium chloride, dried over anhydrous magnesium sulfate and evaporated in vacuo. The resulting residue was chromatographed on silica gel (200 g) eluting with a mixture of chloroform and methanol (9:1 V/V). The fractions containing the desired compound were collected and evaporated in vacuo to give (4S)-4-methyl-2,5-dioxoimidazolidine (18.6 g).

NMR (CD3OD, δ): 1.35 (3H, d, J=7 Hz), 4.08 (1H, q, J=7 Hz)

PREPARATION 52-(2)

(4R)-4-Methyl-2,5-dioxoimidazolidine was obtained quantitatively in substantially the same manner as that of Preparation 52-(1).

NMR (CD3OD, δ): 1.37 (3H, d, J=7 Hz), 4.12 (1H, q, J=7 Hz)

PREPARATION 53-(1)

To a suspension of sodium borohydride (12.3 g) in tetrahydrofuran (180 ml) was dropwise added boron trifluoride etherate (50 ml) under ice-cooling and the mixture was stirred at the same temperature for 15 minutes. To this solution was added a solution of (4S)-4-methyl-2,5-dioxoimidazolidine (18.6 g) in tetrahydrofuran (90 ml) under ice-cooling and the mixture was stirred at ambient temperature overnight. To the solution was dropwise added methanol (100 ml) and the mixture was filtered off. The filtrate was evaporated in vacuo. The resulting residue was dissolved in methanol (200 ml) and conc. hydrochloric acid (5 ml). The solution was allowed to stand at ambient temperature overnight. The reaction mixture was evaporated in vacuo and the resulting residue was chromatographed on silica gel (200 g) eluting with a mixture of chloroform and methanol (19:1 V/V). The fractions containing the desired compound were collected and evaporated in vacuo to give (4S)-4-methyl-2-oxoimidazolidine (12.21 g).

NMR (CDCl3, δ): 1.25 (3H, d, J=7 Hz), 3.06 (1H, t, J=7 Hz), 3.58 (1H, t, J=7 Hz), 3.90 (1H, q, J=7 Hz), 5.10–5.90 (2H, broad s)

PREPARATION 53-(2)

(4R)-4-Methyl-2-oxoimidazolidine (11.58 g) was obtained in 38.6% yield in substantially the same manner as that of Preparation 53-(1).

mp: 90°–92° C.

NMR (CDCl₃, δ): 1.25 (3H, d, J=7 Hz), 3.02-3.10 (1H, m), 3.55-3.64 (1H, m), 3.82-3.96 (1H, m), 5.93 (2H, m)

EI Mass: 100 (M+)

PREPARATION 54-(1)

(2S,4R)-4-Methanesulfonyloxy-2-[(4S)-4-methyl-2-oxoimidazolidin-1-yl]carbonyl-1-(4-nitrobenzyloxycarbonyl)pyrrolidine was obtained in 23.4% yield in substantially the same manner as that of Preparation 18.

NMR (CDCl₃, δ): 1.30 (3H, d, J=6 Hz), 3.04 (3H, s), 7.45 (1H, d, J=8 Hz), 7.52 (1H, d, J=8 Hz), 8.20 (2H, broad d, J=8 Hz)

PREPARATION 54-(2)

(2S,4R)-4-Methanesulfonyloxy-2-[(4R)-4-methyl-2-oxoimidazolidin-1-yl]carbonyl-1-(4-nitrobenzyloxycarbonyl)pyrrolidine was obtained in 29.7% yield in substantially the same manner as that of Preparation 18.

IR (Neat): 1725-1685, 1610, 1525, 1170 cm⁻¹

NMR (CDCl₃, δ): 1.13, 1.32 (3H, double d, J=7 Hz), 2.22-2.34 (1H, m), 2.75-2.87 (1H, m), 3.07 (3H, s), 3.83-4.09 (4H, m), 5.06-5.37 (3H, m), 5.66-5.83 (2H, m), 7.44-7.54 (2H, m), 8.17-8.25 (2H, m)

PREPARATION 55-(1)

(2S,4R)-4-Methanesulfonyloxy-2-[(4S)-4-methyl-2-oxoimidazolidin-1-yl]methyl-1-(4-nitrobenzyloxycarbonyl)pyrrolidine was obtained in 43.9% yield in substantially the same manner as that of Preparation 22.

IR (Neat): 1710-1670, 1605, 1525, 1495, 1270, 1175 cm⁻¹

NMR (CDCl₃, δ): 1.20 (3H, d, J=6 Hz), 2.21-2.49 (2H, m), 3.01 (3H, s), 4.72-5.00 (1H, m), 5.23 (2H, s), 7.50 (2H, d, J=8 Hz), 8.20 (2H, d, J=8 Hz)

PREPARATION 55-(2)

(2S,4R)-4-Methanesulfonyloxy-2-[(4R)-4-methyl-2-oxoimidazolidin-1-yl]methyl-1-(4-nitrobenzyloxycarbonyl)pyrrolidine was obtained in 43.2% yield in substantially the same manner as that of Preparation 22.

NMR (CDCl₃, δ): 1.19 (3H, d, J=6 Hz), 2.21-2.52 (2H, m), 3.02 (3H, s), 5.24 (2H, broad s), 7.53 (2H, d, J=8 Hz), 8.28 (2H, d, J=8 Hz)

PREPARATION 56-(1)

(2S,4S)-4-Acetylthio-2-[(4S)-4-methyl-2-oxoimidazolidin-1-yl]methyl-1-(4-nitrobenzyloxycarbonyl)pyrrolidine was obtained in 54.9% yield in substantially the same manner as that of Preparation 23.

NMR (CDCl₃, δ): 1.20 (3H, d, J=6 Hz), 2.33 (3H, s), 5.22 (2H, broad s), 7.53 (2H, d, J=8 Hz), 8.22 (2H, d, J=8 Hz)

PREPARATION 56-(2)

(2S,4S)-4-Acetylthio-2-[(4R)-4-methyl-2-oxoimidazolidin-1-yl]methyl-1-(4-nitrobenzyloxycarbonyl)pyrrolidine was obtained in 79.5% yield in substantially the same manner as that of Preparation 23.

NMR (CDCl₃, δ): 1.23 (3H, d, J=5 Hz), 2.34 (3H, s), 5.22 (2H, s), 7.53 (2H, d, J=8 Hz), 8.24 (2H, d, J=8 Hz)

PREPARATION 57-(1)

(2S,4S)-4-Mercapto-2-[(4S)-4-methyl-2-oxoimidazolidin-1-yl]methyl-1-(4-nitrobenzyloxycarbonyl)pyrrolidine was obtained in 76.2% yield in substantially the same manner as that of Preparation 24.

IR (Neat): 1720-1670, 1605, 1520, 1490 cm⁻¹

NMR (CDCl₃, δ): 1.21 (3H, d, J=6 Hz), 4.92 (1H, broad s), 5.23 (1H, s), 7.50 (2H, d, J=8 Hz), 8.23 (2H, d, J=8 Hz)

EI Mass: 395 (M⁺+1), 394 (M⁺), 361 (M⁺−33)

PREPARATION 57-(2)

(2S,4S)-4-Mercapto-2-[(4R)-4-methyl-2-oxoimidazolidin-1-yl]methyl-1-(4-nitrobenzyloxycarbonyl)pyrrolidine was obtained in 76.2% yield in substantially the same manner as that of Preparation 24.

IR (Neat): 1710-1675, 1610, 1520 cm⁻¹

NMR (CDCl₃, δ): 1.29 (3H, d, J=5 Hz), 1.70-2.28 (2H, m), 2.33-2.72 (1H, m), 5.22 (2H, s), 7.52 (2H, d, J=8 Hz), 8.22 (2H, d, J=8 Hz)

EXAMPLE 54-(1)

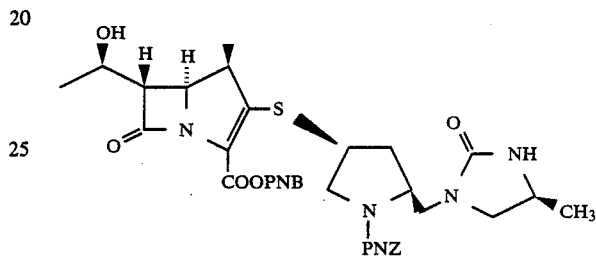

4-Nitrobenzyl (4R,5S,6S)-6-[(1R)-1-hydroxyethyl]-4-methyl-3-[(2S,4S)-2-((4S)-4-methyl-2-oxoimidazolidin-1yl}methyl-1-(4-nitrobenzyloxycarbonyl)pyrrolidin-4-yl]thio-7-oxo-1-azabicyclo[3.2.0]hept-2-ene-2-carboxylate was obtained in 63.3% yield in substantially the same manner as that of Example 1.

IR (Nujol): 1765, 1705, 1690, 1605, 1520 cm⁻¹

NMR (CDCl₃, δ): 1.20 (3H, d, J=6 Hz), 1.28 (3H, d, J=7 Hz), 1.36 (3H, d, J=7 Hz), 5.05-5.64 (4H, m), 7.53 (2H, d, J=8 Hz), 7.64 (2H, d, J=8 Hz), 8.22 (4H, d, J=8 Hz)

EXAMPLE 54-(2)

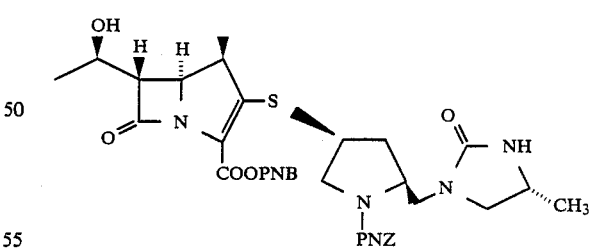

4-Nitrobenzyl (4R,5S,6S)-6-[(1R)-1-hydroxyethyl]-4-methyl-3-[(2S,4S)-2-{(4R)-4-methyl-2-oxoimidazolidin-1-yl}methyl-1-(4-nitrobenzyloxycarbonyl)pyrrolidin-4-yl]thio-7-oxo-1-azabicyclo[3.2.0]hept-2-ene-2-carboxylate was obtained in 63.4% yield in substantially the same manner as that of Example 1.

IR (Nujol): 1750, 1710, 1690-1670, 1515 cm⁻¹

NMR (CDCl₃, δ): 1.15 (3H, d, J=6 Hz), 1.27 (3H, d, J=6 Hz), 1.35 (3H, d, J=6 Hz), 5.19-5.53 (4H, m), 7.50-7.70 (4H, m), 8.21 (2H, d, J=7 Hz), 8.22 (2H, d, J=7 Hz)

EXAMPLE 55-(1)

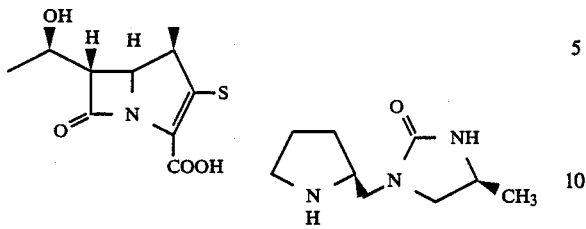

(4R,5S,6S)-6-[(1R)-1-Hydroxyethyl]-4-methyl-3-[(2S,4S)-2-{(4S)-4-methyl-2-oxoimidazolidin-1-yl}methylpyrrolidin-4-yl]thio-7-oxo-1-azabicyclo[3.2.0-]hept-2-ene-2-carboxylic acid was obtained in 53.7% yield in substantially the same manner as that of Example 2.

mp: 176°–181° C. (dec.)
IR (Nujol): 1755–1735, 1675–1650 cm$^{-1}$
NMR (D$_2$O, δ): 1.22 (6H, d, J=6 Hz), 1.28 (3H, d, J=6 Hz), 2.50–2.92 (2H, m)
FB Mass: 425 (M$^+$)

EXAMPLE 55-(2)

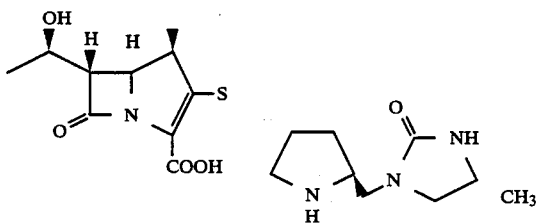

(4R,5S,6S)-6-[(1R)-1-Hydroxyethyl]-4-methyl-3-[(2S,4S)-2-{(4R)-4-methyl-2-oxoimidazolidin-1-yl}methylpyrrolidin-4-yl]thio-7-oxo-1-azabicyclo[3.2.0-]hept-2-ene-2-carboxylic acid was obtained in 67.8% yield in substantially the same manner as that of Example 2.

mp: >181° C. (dec.)
IR (Nujol): 1750, 1680–1660, 1580, 1270–1260 cm$^{-1}$
NMR (D$_2$O, δ): 1.23 (6H, d, J=6 Hz), 1.29 (3H, d, J=6 Hz), 1.52–2.02 (1H, m), 3.02–4.36 (13H, m)
FB Mass: 425 (M$^+$)

What we claim is:

1. A compound of the formula:

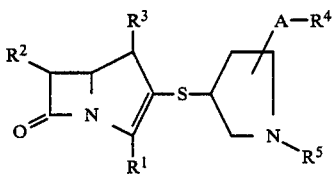

in which
$R^1$ is carboxy or protected carboxy,
$R^2$ is hydroxy(lower)alkyl or protected hydroxy(lower)alkyl,
$R^3$ is hydrogen or lower alkyl,
$R^4$ is saturated, 5 or 6-membered heteromonocyclic group containing 1 to 4 nitrogen atom(s) and optionally 1 or 2 oxygen atom(s), which may be substituted by one or more suitable substituent(s) selected from amino, protected amino, carbamoyl, lower alkyl, oxo, lower alkylsulfonyl, hydroxy(lower)alkyl, carbamoyl(lower)alkyl and imino-protective group,
$R^5$ is hydrogen, lower alkyl or imino protective group, and
A is lower alkylene, or pharmaceutically acceptable salts thereof.

2. A compound of claim 1, wherein
$R^4$ is pyrrolidinyl, imidazolidinyl, pyrazolidinyl, piperidyl, piperidino, piperazinyl, morpholinyl or morpholino, each of which may be substituted by one or two suitable substituent(s) selected from amino, acylamino, carbamoyl, lower alkyl, oxo, lower alkylsulfonyl, hydroxy(lower)alkyl, carbamoyl(lower)alkyl and acyl.

3. A compound of claim 2, wherein
$R^1$ is carboxy or esterified carboxy,
$R^2$ is hydroxy(lower)alkyl, acyloxy(lower)alkyl, (C$_6$–C$_{10}$)ar(lower)alkyloxy(lower)alkyl, tri(lower)alkylsilyloxy(lower)alkyl, tri(C$_6$–C$_{10}$)arylsilyloxy(lower)alkyl or tris[(C$_6$–C$_{10}$)ar(lower)alkyl]silyloxy(lower)alkyl,
$R^4$ is imidazolidinyl, oxoimidazolidinyl, dioxoimidazolidinyl, [(lower)alkylsulfonyl]oxoimidazolidinyl, piperazinyl, N-acylpiperazinyl, (lower)alkylpiperazinyl, N-acyl(lower)alkylpiperazinyl, pyrrolidinyl, aminopyrrolidinyl, acylaminopyrrolidinyl, carbamoylpyrrolidinyl, piperidinyl, aminopiperidinyl, acylaminopiperidinyl, hydroxy(lower)alkylpyrrolidinyl, (lower)alkylpiperazinyl, carbamoylpiperazinyl, oxopiperazinyl, morpholinyl, [(lower)alkyl]oxoimidazolidinyl or [hydroxy(lower)alkyl]oxoimidazolidinyl, and
$R^5$ is hydrogen, lower alkyl or acyl.

4. A compound of claim 3, wherein
$R^1$ is carboxy, lower alkenyloxycarbonyl or phenyl(or nitrophenyl)(lower)alkoxycarbonyl,
$R^2$ is hydroxy(lower)alkyl or [phenyl(or nitrophenyl)(lower)alkoxy]carbonyloxy(lower)alkyl,
$R^3$ is hydrogen or lower alkyl, and
$R^5$ is hydrogen, lower alkyl, lower alkenyloxy-carbonyl or phenyl(or nitrophenyl)(lower)alkoxycarbonyl.

5. A compound of claim 4, wherein
$R^1$ is carboxy, C$_2$–C$_4$ alkenyloxycarbonyl or phenyl(or nitrophenyl)(C$_1$–C$_4$)alkoxycarbonyl,
$R^2$ is hydroxy(C$_1$–C$_4$)alkyl or [phenyl(or nitrophenyl)(C$_1$–C$_4$)alkoxy]carbonyloxy(C$_1$–C$_4$)alkyl,
$R^3$ is hydrogen or C$_1$–C$_4$ alkyl,
$R^4$ is imidazolidinyl, oxoimidazolidinyl, dioxoimidazolidinyl, [(C$_1$–C$_4$)alkylsulfonyl]oxoimidazolidinyl, piperazinyl, N-phenyl(or nitrophenyl)(C$_1$–C$_4$)alkoxycarbonylpiperazinyl, (C$_1$–C$_4$)alkylpiperazinyl, N-phenyl(or nitrophenyl)(C$_1$–C$_4$)alkoxycarbonyl(C$_1$–C$_4$)alkylpiperazinyl, pyrrolidinyl, aminopyrrolidinyl, phenyl(or nitrophenyl)(C$_1$–C$_4$)alkoxycarbonylaminopyrrolidinyl, carbamoylpyrrolidinyl, piperidinyl, aminopiperidinyl, phenyl(or nitrophenyl)(C$_1$–C$_4$)alkoxycarbonylaminopiperidinyl or hydroxy(C$_1$–C$_4$)alkylpyrrolidinyl, (C$_1$–C$_4$)alkylpiperazinyl, carbamoylpiperazinyl, oxopiperazinyl, morpholinyl, [(C$_1$–C$_4$)alkyl]oxoimidazolidinyl, [hydroxy(C$_1$–C$_4$)alkyl]oxoimidazolidinyl,
$R^5$ is hydrogen, C$_1$–C$_4$ alkyl, C$_2$–C$_4$ alkenyloxycarbonyl or phenyl(or nitrophenyl)(C$_1$–C$_4$)alkoxycarbonyl, and
A is C$_1$–C$_4$ alkylene.

6. A compound of claim 5, wherein
$R^1$ is carboxy,
$R^2$ is hydroxy($C_1$–$C_4$)alkyl,
$R^3$ is $C_1$–$C_4$alkyl,
$R^4$ is imidazolidinyl, oxoimidazolidinyl, dioxoimidazolidinyl, [($C_1$–$C_4$)alkylsulfonyl]oxoimidazolidinyl, piperazinyl, ($C_1$–$C_4$)alkylpiperazinyl, pyrrolidinyl, aminopyrrolidinyl, carbamoylpyrrolidinyl, piperidinyl, aminopiperidinyl, hydroxy($C_1$–$C_4$)alkylpyrrolidinyl, ($C_1$–$C_4$)alkylpiperazinyl, carbamoylpiperazinyl, [($C_1$–$C_4$)alkyl]oxoimidazolidinyl, or oxopiperazinyl, morpholinyl, [hydroxy($C_1$–$C_4$)alkyl]oxoimidazolidinyl,
$R^5$ is hydrogen or $C_1$–$C_4$ alkyl, and
A is $C_1$–$C_4$ alkylene.

7. A compound of claim 6, wherein
$R^1$ is carboxy,
$R^2$ is 1-hydroxyethyl,
$R^3$ is methyl,
$R^4$ is imidazolidin-1-yl, 2-oxoimidazolidin-1-yl, 2,4-dioxoimidazolidin-1-yl, 2,5-dioxoimidazolidin-1-yl, 3-methylsulfonyl-2-oxoimidazolidin-1-yl, piperazin-1-yl, 3-methylpiperazin-1-yl, 4-methylpiperazin-1-yl, pyrrolidin-1-yl, 3-aminopyrrolidin-1-yl, 2-carbamoylpyrrolidin-1-yl, piperidin-1-yl, 4-aminopiperidin-1-yl, 2-hydroxymethylpyrrolidin-1-yl, 4-methylpiperazin-1-yl, 4-carbamoylpiperazin-1-yl, 3-oxopiperazin-1-yl, morpholino, 3(or 4)-methyl-2-oxoimidazolidin-1-yl, 3-ethyl-2-oxoimidazolidin-1-yl or 3-(2-hydroxyethyl)-2-oxoimidazolidin-1-yl-,
$R^5$ is hydrogen or methyl, and
A is methylene.

8. An antimicrobial pharmaceutical composition comprising, an effective amount of a compound of claim 1, in admixture with a pharmaceutically acceptable carrier or excipient.

9. A method for the treatment of infectious diseases caused by pathogenic bacteria which comprises administering an effective amount of a compound of claim 1 to a human being or animal.

* * * * *

UNITED STATES PATENT AND TRADEMARK OFFICE
CERTIFICATE OF CORRECTION

PATENT NO. : 4,925,838

DATED : May 15, 1990

INVENTOR(S) : Masayoshi MURATA, et al.

It is certified that error appears in the above-identified patent and that said Letters Patent is hereby corrected as shown below:

At column 65, line 30

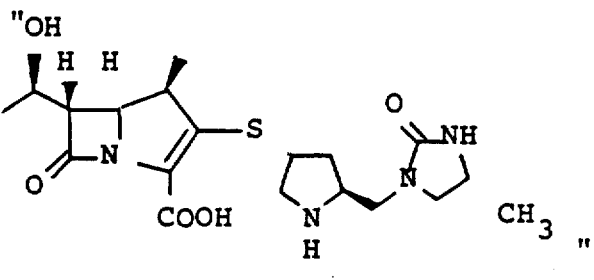

should read

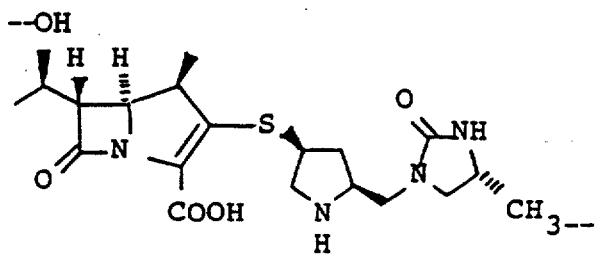

At column 66, line 61, "or" should read --,--;

line 63, "," (third occurrence) should read --or--.

UNITED STATES PATENT AND TRADEMARK OFFICE
CERTIFICATE OF CORRECTION

PATENT NO. : 4,925,838

DATED : May 15, 1990

INVENTOR(S) : Masayoshi MURATA, et al.

It is certified that error appears in the above-identified patent and that said Letters Patent is hereby corrected as shown below:

At column 67, line 12, "or" should be deleted;

line 13, "," (first occurrence) should read --or--.

Signed and Sealed this

Twenty-first Day of April, 1992

Attest:

HARRY F. MANBECK, JR.

*Attesting Officer*      *Commissioner of Patents and Trademarks*